(12) United States Patent
Abe et al.

(10) Patent No.: US 9,017,969 B2
(45) Date of Patent: Apr. 28, 2015

(54) SUGAR-CHAIN MODIFIED YEAST AND METHOD FOR PRODUCING GLYCOPROTEIN USING THE SAME

(75) Inventors: Hiroko Abe, Kagawa (JP); Kazuya Tomimoto, Kagawa (JP); Yasuko Fujita, Kagawa (JP); Tomoko Iwaki, Kagawa (JP); Yasunori Chiba, Ibaraki (JP); Yoshihiro Nakajima, Kagawa (JP); Kenichi Nakayama, Hokkaido (JP); Masatoshi Kataoka, Kagawa (JP); Shouki Yatsushiro, Kagawa (JP); Shohei Yamamura, Kagawa (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 238 days.

(21) Appl. No.: 13/409,558

(22) Filed: Mar. 1, 2012

(65) Prior Publication Data

US 2013/0171692 A1    Jul. 4, 2013

(30) Foreign Application Priority Data

Dec. 28, 2011   (JP) ................ 2011-289411

(51) Int. Cl.
| | |
|---|---|
| C12P 21/00 | (2006.01) |
| C12N 1/19 | (2006.01) |
| C12N 1/16 | (2006.01) |
| C12N 9/10 | (2006.01) |
| C12N 9/34 | (2006.01) |
| C12N 9/60 | (2006.01) |
| C07K 14/47 | (2006.01) |
| C12N 9/24 | (2006.01) |
| C12N 15/09 | (2006.01) |

(52) U.S. Cl.
CPC ........... *C12P 21/005* (2013.01); *C07K 14/4726* (2013.01); *C07K 2319/03* (2013.01); *C12N 1/16* (2013.01); *C12N 9/1051* (2013.01); *C12N 9/24* (2013.01); *C12N 9/2428* (2013.01); *C12N 9/2488* (2013.01); *C12N 9/60* (2013.01); *C12N 15/09* (2013.01); *C12Y 204/01109* (2013.01); *C12Y 204/01132* (2013.01); *C12Y 204/01255* (2013.01); *C12Y 302/01003* (2013.01); *C12Y 302/01113* (2013.01); *C12Y 304/21048* (2013.01); *C12Y 304/23025* (2013.01)

(58) Field of Classification Search
None
See application file for complete search history.

(56) References Cited

U.S. PATENT DOCUMENTS

| | | | |
|---|---|---|---|
| 5,714,377 | A | 2/1998 | Tanner et al. |
| 2007/0077560 | A1 | 4/2007 | Furusawa |
| 2008/0038778 | A1 | 2/2008 | Abe et al. |

FOREIGN PATENT DOCUMENTS

| | | |
|---|---|---|
| EP | 1211310 | 5/2002 |
| JP | 2012-152211 A | 8/2012 |

OTHER PUBLICATIONS

Abstract—Tomimoto, Kazuya, et al., "Development of O-mannose-type sugar chain-suppressed strains derived from human-type N-linked glycoprotein-producing yeast" Annual Meeting of Japan Society for Bioscience, Biotechnology, and Agrochemistry in Kyoko, 2011, Dated Mar. 5, 2011, Publisher: Japanese Society for Bioscience, Biotechnology, and Agrochemistry.
Jones, Elizabeth W., "Three Proteolytic Systems in the Yeast Saccharomyces cerevisiae", The Journal of Biological Chemistry, vol. 266, No. 13, May 5, 1991, pp. 7963-7966.
De Poureq, Karen, et al., "Engineering of Glycosylation in Yeast and other Fungi: Current State and Perspectives", Applied Microbiology and Biotechnology, vol. 87, 2010, pp. 1617-1631.
JP 2012-152211, publication date Aug. 16, 2012, English translation of abstract of priority application JP Appl. No. 2011-289411.
JP Appl. No. 2011-000268, filed Jan. 4, 2011.

*Primary Examiner* — Nancy T Vogel
(74) *Attorney, Agent, or Firm* — McCarter & English

(57) ABSTRACT

The present invention provides: genetically modified yeasts such as mutant yeasts having an ability to produce N-linked sugar chains of $Man_5GlcNAc_2$ and a decreased ability to produce O-linked sugar chains, mutant yeasts having an ability to produce N-linked sugar chains of $Man_5GlcNAc_2$ and further having an ability to produce N-linked sugar chains of $GlcNAc_1Man_5GlcNAc_2$, and mutant yeasts having an increased ability to produce and secrete proteins and an ability to produce N-linked sugar chains of $Man_5GlcNAc_2$; and a method for producing glycoproteins using them.

15 Claims, 13 Drawing Sheets
(2 of 13 Drawing Sheet(s) Filed in Color)

Lane 1 W303-1B
Lane 2 TIY20
Lane 3 YAB100
Lane 4 YFY20
Lane 5 YFY22
Lane 6 YFY24

ConA staining

SEQUENCE LISTING

```
<160> NUMBER OF SEQ ID NOS: 65

<210> SEQ ID NO 1
<211> LENGTH: 3294
<212> TYPE: DNA
<213> ORGANISM: Saccharomyces cerevisiae

<400> SEQUENCE: 1
atgagtgaaa aaagatccct tcccatggtt gatgtgaaga tcgatgacga ggatactccc      60
cagttggaaa agaaaatcaa acggcaatca atagatcatg gtgttggaag tgaacctgtt     120
tcaacaatag agattattcc gagtgattct tttcgaaaat ataatagtca aggcttcaaa     180
gcaaaggata cagatttaat gggtacgcaa ttagagtcta cttttgaaca agacgtatcg     240
caaatggaac atgatatggc cgaccaagaa gagcatgacc tgtcatcatt cgagcgtaag     300
```

```
aaacttccaa ccgattttga cccaagtttg tatgatattt ctttccaaca aattgatgcg    360
gaacagagcg tactgaatgg tatcaaagat gaaaatacat ctaccgtggt aaggtttttt    420
ggtgtcacta gtgaaggaca ctctgtactt tgtaatgtta cagggttcaa gaactatctt    480
tacgtcccag cgcccaattc ttccgacgct aacgatcagg agcaaatcaa caagtttgtg    540
cactatttaa acgaaacatt tgaccacgct attgattcga ttgaagttgt atctaaacag    600
tctatctggg gttattccgg agataccaaa ttaccattct ggaaaatata cgtcaccctat   660 ccgcatatgg tcaacaaact gcgtactgcg tttgaaagag gtcatctttc attcaactcg    720
tggttttcta acggcacgac tacttatgat aacattgcct acactttaag gttaatggta    780
gattgtggaa ttgtcggtat gtcctggata acattaccaa aaggaaagta ttcgatgatt    840
gagcctaata acagagtttc ctcttgtcag ttggaagttt caattaatta tcgtaaccta    900
atagcacatc ctgctgaggg tgattggtct catacagctc cattgcgtat catgtccttt    960
gctatcgcgt gtgctggtag gattggcgtc tttccggaac ctgaatacga tcccgtcatc   1020
caaattgcca acgttgtgag tattgctggc gctaagaaac cattcattcg taatgtgttt   1080
actctgaata catgctcacc cataacaggt tcaatgattt tttcccacgc cactgaagag   1140
gaaatgttga gcaattggcg taactttatc atcaaagttg atcctgatgt tatcattggt   1200
tataatacta caaattttga tatcccttat cttttaaacc gtgcaaaggc gctaaaggtg   1260
aatgatttcc catattttgg aaggttaaaa accgttaagc aagaaattaa agagtctgtg   1320
ttctcttcga aggcttatgg tacaagagaa accaaaaatg tcaatattga cggccgatta   1380
cagttggatc ttttgcaatt tattcagcgt gagtataaac taagatccta cacgttgaat   1440
gcagtctctg cgcactttt aggtgaacag aaggaggatg tacattatag catcatttct   1500
gatctacaaa atggcgatag tgaaacaaga agaaggttgg ccgtttactg tttgaaagac   1560
gcctacctgc ctttaaggct tatggaaaaa ctaatggcgt tagttaacta tacagaaatg   1620
gctcgtgtta caggtgtgcc attttcatat ttactagctc gtggtcaaca aattaaagtt   1680
gtttctcaac tatttcgaaa gtgcctggag attgatactg tgatacctaa catgcaatct   1740
caggcctctg atgaccaata tgagggtgcc actgttattg agcctattcg tggttattac   1800
gatgtaccga ttgcaacttt ggatttcaat tctttatatc caagtattat gatggcgcac   1860
aacctatgtt atacaacact tgtaacaaa gctactgtag agagattgaa tcttaaaatt   1920
gacgaagact acgtcataac acctaatgga gattattttg ttaccacaaa agaaggcgt   1980 ggtatattac caattattct ggatgaatta ataagtgcta gaaaacgcgc taaaaaagat   2040
ctgagagatg agaaggatcc attcaaaaga gatgttttaa atggtagaca attggctttg   2100
aagatttcag ctaactctgt ctatggtttt acaggagcga cggtgggtaa attgccatgt   2160
ttagccattt cttcatctgt tactgcttat ggtcgtacca tgattttaaa aactaaaacc   2220
gcagtccaag aaaaatattg tataaagaat ggttataagc acgatgccgt tgtggtttac   2280
ggtgacactg attccgttat ggtaaagttt ggtacaacag atttaaagga agctatggat   2340
cttggtaccg aagctgccaa atatgtctcc actctattca acatccgat taacttagaa    2400 tttgaaaaag catacttccc ttaccttttg ataaataaaa agcgttatgc aggtttattc   2460
tggactaatc ctgacaagtt tgacaagttg gaccaaaaag gccttgcttc tgtccgtcgt   2520
gattcctgtt ccttggtttc tattgttatg aataaagttt taaagaaaat tttaattgaa   2580
agaaatgtag atggtgcttt agcttttgtc agagaaacta tcaatgatat tctgcataat   2640
```

-continued

```
agagtagata tttcaaagtt gattatatca aagacgttag ccccaaatta cacaaatcca   2700
cagccgcacg ccgttttggc tgaacgtatg aagaggagag agggcgttgg tccaaatgtt   2760
ggtgatcgtg tggactatgt cattatcggt ggtaatgata aactttacaa tagagcagaa   2820
gatccattat ttgtactaga aaacaatatt caagtggatt cgcgctatta tttaactaat   2880
caattacaaa atccaatcat tagtattgtt gcacctatta ttggcgacaa acaggcgaac   2940
ggtatgttcg ttgtgaaatc cattaaaatt aacacaggct ctcaaaaagg aggcttgatg   3000
agctttatta aaaagttga ggcttgtaaa agttgtaaag gtccgttgag gaaaggtgaa   3060
ggccctcttt gttcaaactg tctagcaagg tctggagaat tatacataaa ggcattatac   3120
gatgtcagag atttagagga aaaatactca agattatgga cacaatgcca aggtgcgct   3180 ggtaacttac atagtgaagt tttgtgttca aataagaact gtgacatttt ttatatgcgg   3240
gttaaggtta aaaagagct gcaggagaaa gtagaacaat taagcaaatg gtaa          3294
```

<210> SEQ ID NO 2
<211> LENGTH: 61
<212> TYPE: PRT
<213> ORGANISM: Saccharomyces cerevisiae

<400> SEQUENCE: 2

```
Met Ser Arg Lys Leu Ser His Leu Ile Ala Thr Arg Lys Ser Lys Thr
1               5                   10                  15

Ile Val Val Thr Val Leu Leu Ile Tyr Ser Leu Leu Thr Phe His Leu
                20                  25                  30

Ser Asn Lys Arg Leu Leu Ser Gln Phe Tyr Pro Ser Lys Asp Asp Phe
            35                  40                  45

Lys Gln Thr Leu Leu Pro Thr Thr Ser His Ser Gln Asp
        50                  55                  60
```

<210> SEQ ID NO 3
<211> LENGTH: 476
<212> TYPE: PRT
<213> ORGANISM: Aspergillus saitoi

<400> SEQUENCE: 3

```
Thr Thr Gln Ser Arg Ala Asp Ala Ile Lys Ala Ala Phe Ser His Ala
1               5                   10                  15

Trp Asp Gly Tyr Leu Gln Tyr Ala Phe Pro His Asp Glu Leu His Pro
                20                  25                  30

Val Ser Asn Gly Tyr Gly Asp Ser Arg Asn Gly Trp Gly Ala Ser Ala
            35                  40                  45

Val Asp Ala Leu Ser Thr Ala Val Ile Met Arg Asn Ala Thr Ile Val
        50                  55                  60

Asn Gln Ile Leu Asp His Val Gly Lys Ile Asp Tyr Ser Lys Thr Asn
65                  70                  75                  80

Thr Thr Val Ser Leu Phe Glu Thr Thr Ile Arg Tyr Leu Gly Gly Met
                85                  90                  95

Leu Ser Gly Tyr Asp Leu Leu Lys Gly Pro Val Ser Asp Leu Val Gln
            100                 105                 110

Asn Ser Ser Lys Ile Asp Val Leu Leu Thr Gln Ser Lys Asn Leu Ala
        115                 120                 125

Asp Val Leu Lys Phe Ala Phe Asp Thr Pro Ser Gly Val Pro Tyr Asn
    130                 135                 140

Asn Leu Asn Ile Thr Ser Gly Gly Asn Asp Gly Ala Lys Thr Asn Gly
145                 150                 155                 160
```

```
Leu Ala Val Thr Gly Thr Leu Ala Leu Glu Trp Thr Arg Leu Ser Asp
                165                 170                 175

Leu Thr Gly Asp Thr Thr Tyr Ala Asp Leu Ser Gln Lys Ala Glu Ser
            180                 185                 190

Tyr Leu Leu Asn Pro Gln Pro Lys Ser Ala Glu Pro Phe Pro Gly Leu
        195                 200                 205

Val Gly Ser Asn Ile Asn Ile Ser Asn Gly Gln Phe Thr Asp Ala Gln
    210                 215                 220

Val Ser Trp Asn Gly Gly Asp Asp Ser Tyr Tyr Glu Tyr Leu Ile Lys
225                 230                 235                 240

Met Tyr Val Tyr Asp Pro Lys Arg Phe Gly Leu Tyr Lys Asp Arg Trp
                245                 250                 255

Val Ala Ala Ala Gln Ser Thr Met Gln His Leu Ala Ser His Pro Ser
            260                 265                 270

Ser Arg Pro Asp Leu Thr Phe Leu Ala Ser Tyr Asn Asn Gly Thr Leu
        275                 280                 285

Gly Leu Ser Ser Gln His Leu Thr Cys Phe Asp Gly Gly Ser Phe Leu
    290                 295                 300

Leu Gly Gly Thr Val Leu Asn Arg Thr Asp Phe Ile Asn Phe Gly Leu
305                 310                 315                 320

Asp Leu Val Ser Gly Cys His Asp Thr Tyr Asn Ser Thr Leu Thr Gly
                325                 330                 335

Ile Gly Pro Glu Ser Phe Ser Trp Asp Thr Ser Asp Ile Pro Ser Ser
            340                 345                 350

Gln Gln Ser Leu Tyr Glu Lys Ala Gly Phe Tyr Ile Thr Ser Gly Ala
        355                 360                 365

Tyr Ile Leu Arg Pro Glu Val Ile Glu Ser Phe Tyr Tyr Ala Trp Arg
    370                 375                 380

Val Thr Gly Gln Glu Thr Tyr Arg Asp Trp Ile Trp Ser Ala Phe Ser
385                 390                 395                 400

Ala Val Asn Asp Tyr Cys Arg Thr Ser Ser Gly Phe Ser Gly Leu Thr
                405                 410                 415

Asp Val Asn Ala Ala Asn Gly Gly Ser Arg Tyr Asp Asn Gln Glu Ser
            420                 425                 430

Phe Leu Phe Ala Glu Val Met Lys Tyr Ser Tyr Met Ala Phe Ala Glu
        435                 440                 445

Asp Ala Ala Trp Gln Val Gln Pro Gly Ser Gly Asn Gln Phe Val Phe
    450                 455                 460

Asn Thr Glu Ala His Pro Val Arg Val Ser Ser Thr
465                 470                 475

<210> SEQ ID NO 4
<211> LENGTH: 45
<212> TYPE: DNA
<213> ORGANISM: Artificial
<220> FEATURE:
<223> OTHER INFORMATION: primer

<400> SEQUENCE: 4
cccccgcggc cgcggaacaa caagaagttt aatgacgcgg aggcc            45

<210> SEQ ID NO 5
<211> LENGTH: 46
<212> TYPE: DNA
<213> ORGANISM: Artificial
<220> FEATURE:
```

<223> OTHER INFORMATION: primer

<400> SEQUENCE: 5
gggggggtac cgaatcgaaa atgtcattaa aatagtatat aaattg        46

<210> SEQ ID NO 6
<211> LENGTH: 15
<212> TYPE: DNA
<213> ORGANISM: Artificial
<220> FEATURE:
<223> OTHER INFORMATION: primer

<400> SEQUENCE: 6
cgaagaacct cgccg        15

<210> SEQ ID NO 7
<211> LENGTH: 47
<212> TYPE: DNA
<213> ORGANISM: Artificial
<220> FEATURE:
<223> OTHER INFORMATION: primer

<400> SEQUENCE: 7
gggcccgtcg acttatgtac tactcacccg cactggatgt gcctcgg        47

<210> SEQ ID NO 8
<211> LENGTH: 15
<212> TYPE: DNA
<213> ORGANISM: Artificial
<220> FEATURE:
<223> OTHER INFORMATION: primer

<400> SEQUENCE: 8
cgaagaacct cgccg        15

<210> SEQ ID NO 9
<211> LENGTH: 18
<212> TYPE: DNA
<213> ORGANISM: Artificial
<220> FEATURE:
<223> OTHER INFORMATION: primer

<400> SEQUENCE: 9
gtcaagtgtt gcgagctc        18

<210> SEQ ID NO 10
<211> LENGTH: 19
<212> TYPE: DNA
<213> ORGANISM: Artificial
<220> FEATURE:
<223> OTHER INFORMATION: primer

<400> SEQUENCE: 10
ggtagagggt gaacgttac        19

<210> SEQ ID NO 11
<211> LENGTH: 17
<212> TYPE: DNA
<213> ORGANISM: Artificial
<220> FEATURE:
<223> OTHER INFORMATION: primer

<400> SEQUENCE: 11
tgatcttaca cacctgc        17

```
<210> SEQ ID NO 12
<211> LENGTH: 19
<212> TYPE: DNA
<213> ORGANISM: Artificial
<220> FEATURE:
<223> OTHER INFORMATION: primer

<400> SEQUENCE: 12
gacacgtgtc gaagaagag                                                    19

<210> SEQ ID NO 13
<211> LENGTH: 17
<212> TYPE: DNA
<213> ORGANISM: Artificial
<220> FEATURE:
<223> OTHER INFORMATION: primer

<400> SEQUENCE: 13
tgatcttaca cacctgc                                                      17

<210> SEQ ID NO 14
<211> LENGTH: 19
<212> TYPE: DNA
<213> ORGANISM: Artificial
<220> FEATURE:
<223> OTHER INFORMATION: primer

<400> SEQUENCE: 14
ggtagagggt gaacgttac                                                    19

<210> SEQ ID NO 15
<211> LENGTH: 18
<212> TYPE: DNA
<213> ORGANISM: Artificial
<220> FEATURE:
<223> OTHER INFORMATION: primer

<400> SEQUENCE: 15
cgaataacac gagtacgg                                                     18

<210> SEQ ID NO 16
<211> LENGTH: 18
<212> TYPE: DNA
<213> ORGANISM: Artificial
<220> FEATURE:
<223> OTHER INFORMATION: primer

<400> SEQUENCE: 16
gatccgtttc gtgtactg                                                     18

<210> SEQ ID NO 17
<211> LENGTH: 18
<212> TYPE: DNA
<213> ORGANISM: Artificial
<220> FEATURE:
<223> OTHER INFORMATION: primer

<400> SEQUENCE: 17
cgaataacac gagtacgg                                                     18

<210> SEQ ID NO 18
<211> LENGTH: 408
<212> TYPE: PRT
<213> ORGANISM: Oryza sativa

<400> SEQUENCE: 18
```

```
Asp Arg Leu Ala Gln Ala Glu Lys Ser Glu Asn Gln Cys Thr Ser Gln
1               5                   10                  15

Leu Arg Ser Leu Ile Asp Gln Val Ser Ser Gln Gln Glu Lys Ile Val
            20                  25                  30

Ala Leu Glu Glu Met Lys Ile Arg Gln Asp Glu Glu Arg Val His Leu
        35                  40                  45

Lys Ile Leu Ile Gln Asp Leu Glu Lys Arg Ser Val Gln Thr Leu Val
    50                  55                  60

Asn Asn Asn Val Ala Pro Val Ala Ala Val Val Met Ala Cys Asn
65                  70                  75                  80

Arg Pro Asp Tyr Leu Gln Arg Thr Val Glu Ser Ile Leu Lys Tyr Gln
                85                  90                  95

Thr Ser Val Ala Ser Lys Phe Pro Leu Phe Ile Ser Gln Asp Gly Ile
            100                 105                 110

Asn Gly Glu Val Lys Lys Lys Ala Leu Ser Tyr Asn Glu Ile Thr Tyr
        115                 120                 125

Met Gln His Leu Asp Leu Glu Pro Val Arg Thr Glu Arg Pro Gly Glu
    130                 135                 140

Leu Ile Ala Tyr Tyr Lys Ile Ala Lys His Tyr Lys Trp Ala Leu Asp
145                 150                 155                 160

Glu Leu Phe Ile Lys His Asn Phe Ala Arg Val Ile Ile Leu Glu Asp
                165                 170                 175

Asp Met Glu Ile Ala Pro Asp Phe Phe Asp Tyr Phe Glu Ala Ala Ala
            180                 185                 190

Lys Leu Leu Asp Asn Asp Lys Thr Ile Met Ala Val Ser Ser Trp Asn
    195                 200                 205

Asp Asn Gly Gln Lys Gln Phe Val Tyr Asp Pro Lys Ala Leu Tyr Arg
210                 215                 220

Ser Asp Phe Phe Pro Gly Leu Gly Trp Met Leu Thr Lys Pro Thr Trp
225                 230                 235                 240

Ile Glu Leu Ser Pro Lys Trp Pro Lys Ala Tyr Trp Asp Asp Trp Val
                245                 250                 255

Arg Leu Lys Glu Val His Arg Asp Arg Gln Phe Ile Arg Pro Glu Val
            260                 265                 270

Cys Arg Thr Tyr Asn Phe Gly Glu His Gly Ser Ser Met Gly Gln Phe
    275                 280                 285

Phe Arg Gln Tyr Leu Glu Pro Ile Lys Leu Asn Asp Ala His Ile Lys
    290                 295                 300

Trp Asn Ser Glu Asp Leu Ser Tyr Leu Lys Glu Asp Lys Phe Leu Ile
305                 310                 315                 320

Gln Phe Gly Lys Asp Val Ala Ser Ala Thr Pro Leu His Gly Ser Asp
                325                 330                 335

Ala Ala Leu Lys Ala His Asn Met Asp Ala Asp Val Arg Ile Gln Tyr
            340                 345                 350

Asn Asp Gln Glu Asp Phe Glu Arg Ile Ala Arg Gln Phe Gly Ile Phe
    355                 360                 365

Glu Glu Trp Lys Asp Gly Ile Pro Arg Thr Ala Tyr Lys Gly Val Val
    370                 375                 380

Val Phe Arg Tyr Lys Ser Ser Arg Arg Ile Tyr Leu Val Gly Pro
385                 390                 395                 400

Asp Ser Leu Ser Gln Leu Arg Val
            405
```

<210> SEQ ID NO 19
<211> LENGTH: 40
<212> TYPE: PRT
<213> ORGANISM: Saccharomyces cerevisiae

<400> SEQUENCE: 19

Met Ser Leu Ser Leu Val Ser Tyr Arg Leu Arg Lys Asn Pro Trp Val
1               5                   10                  15

Asn Ile Phe Leu Pro Val Leu Ala Ile Phe Leu Ile Tyr Ile Ile Phe
            20                  25                  30

Phe Gln Arg Asp Gln Ser Leu Leu
        35                  40

<210> SEQ ID NO 20
<211> LENGTH: 76
<212> TYPE: DNA
<213> ORGANISM: Artificial
<220> FEATURE:
<223> OTHER INFORMATION: primer

<400> SEQUENCE: 20
aaaagagctc atgccatacc catacgatgt tccagattac gctatgtcac tttctcttgt    60
atcgtaccgc ctaaga                                                   76

<210> SEQ ID NO 21
<211> LENGTH: 41
<212> TYPE: DNA
<213> ORGANISM: Artificial
<220> FEATURE:
<223> OTHER INFORMATION: primer

<400> SEQUENCE: 21
aaaatctaga ctatacccta agctgactga gggaatccgg a                       41

<210> SEQ ID NO 22
<211> LENGTH: 28
<212> TYPE: DNA
<213> ORGANISM: Artificial
<220> FEATURE:
<223> OTHER INFORMATION: primer

<400> SEQUENCE: 22
aaagcatgcg cagcgagtca gtgagcga                                      28

<210> SEQ ID NO 23
<211> LENGTH: 20
<212> TYPE: DNA
<213> ORGANISM: Artificial
<220> FEATURE:
<223> OTHER INFORMATION: primer

<400> SEQUENCE: 23
tgttgggaag ggcgatcggt                                               20

<210> SEQ ID NO 24
<211> LENGTH: 3294
<212> TYPE: DNA
<213> ORGANISM: Saccharomyces cerevisiae
<220> FEATURE:
<221> NAME/KEY: CDS
<222> LOCATION: (1)..(3294)

<400> SEQUENCE: 24 atg agt gaa aaa aga tcc ctt ccc atg gtt gat gtg aag atc gat gac    48
Met Ser Glu Lys Arg Ser Leu Pro Met Val Asp Val Lys Ile Asp Asp

```
1               5                   10                  15
gag gat act ccc cag ttg gaa aag aaa atc aaa cgg caa tca ata gat      96
Glu Asp Thr Pro Gln Leu Glu Lys Lys Ile Lys Arg Gln Ser Ile Asp
             20                  25                  30 cat ggt gtt gga agt gaa cct gtt tca aca ata gag att att ccg agt     144
His Gly Val Gly Ser Glu Pro Val Ser Thr Ile Glu Ile Ile Pro Ser
         35                  40                  45 gat tct ttt cga aaa tat aat agt caa ggc ttc aaa gca aag gat aca     192
Asp Ser Phe Arg Lys Tyr Asn Ser Gln Gly Phe Lys Ala Lys Asp Thr
     50                  55                  60 gat tta atg ggt acg caa tta gag tct act ttt gaa caa gac gta tcg     240
Asp Leu Met Gly Thr Gln Leu Glu Ser Thr Phe Glu Gln Asp Val Ser
 65                  70                  75                  80 caa atg gaa cat gat atg gcc gac caa gaa gag cat gac ctg tca tca     288
Gln Met Glu His Asp Met Ala Asp Gln Glu Glu His Asp Leu Ser Ser
                 85                  90                  95 ttc gag cgt aag aaa ctt cca acc gat ttt gac cca agt ttg tat gat     336
Phe Glu Arg Lys Lys Leu Pro Thr Asp Phe Asp Pro Ser Leu Tyr Asp
             100                 105                 110 att tct ttc caa caa att gat gcg gaa cag agc gta ctg aat ggt atc     384
Ile Ser Phe Gln Gln Ile Asp Ala Glu Gln Ser Val Leu Asn Gly Ile
         115                 120                 125 aaa gat gaa aat aca tct acc gtg gta agg ttt ttt ggt gtc act agt     432
Lys Asp Glu Asn Thr Ser Thr Val Val Arg Phe Phe Gly Val Thr Ser
     130                 135                 140 gaa gga cac tct gta ctt tgt aat gtt aca ggg ttc aag aac tat ctt     480
Glu Gly His Ser Val Leu Cys Asn Val Thr Gly Phe Lys Asn Tyr Leu
145                 150                 155                 160 tac gtc cca gcg ccc aat tct tcc gac gct aac gat cag gag caa atc     528
Tyr Val Pro Ala Pro Asn Ser Ser Asp Ala Asn Asp Gln Glu Gln Ile
                 165                 170                 175 aac aag ttt gtg cac tat tta aac gaa aca ttt gac cac gct att gat     576
Asn Lys Phe Val His Tyr Leu Asn Glu Thr Phe Asp His Ala Ile Asp
             180                 185                 190 tcg att gaa gtt gta tct aaa cag tct atc tgg ggt tat tcc gga gat     624
Ser Ile Glu Val Val Ser Lys Gln Ser Ile Trp Gly Tyr Ser Gly Asp
         195                 200                 205 acc aaa tta cca ttc tgg aaa ata tac gtc acc tat ccg cat atg gtc     672
Thr Lys Leu Pro Phe Trp Lys Ile Tyr Val Thr Tyr Pro His Met Val
     210                 215                 220 aac aaa ctg cgt act gcg ttt gaa aga ggt cat ctt tca ttc aac tcg     720
Asn Lys Leu Arg Thr Ala Phe Glu Arg Gly His Leu Ser Phe Asn Ser
225                 230                 235                 240 tgg ttt tct aac ggc acg act act tat gat aac att gcc tac act tta     768
Trp Phe Ser Asn Gly Thr Thr Thr Tyr Asp Asn Ile Ala Tyr Thr Leu
                 245                 250                 255 agg tta atg gta gat tgt gga att gtc ggt atg tcc tgg ata aca tta     816
Arg Leu Met Val Asp Cys Gly Ile Val Gly Met Ser Trp Ile Thr Leu
             260                 265                 270 cca aaa gga aag tat tcg atg att gag cct aat aac aga gtt tcc tct     864
Pro Lys Gly Lys Tyr Ser Met Ile Glu Pro Asn Asn Arg Val Ser Ser
         275                 280                 285 tgt cag ttg gaa gtt tca att aat tat cgt aac cta ata gca cat cct     912
Cys Gln Leu Glu Val Ser Ile Asn Tyr Arg Asn Leu Ile Ala His Pro
     290                 295                 300 gct gag ggt gat tgg tct cat aca gct cca ttg cgt atc atg tcc ttt     960
Ala Glu Gly Asp Trp Ser His Thr Ala Pro Leu Arg Ile Met Ser Phe
305                 310                 315                 320 gct atc gcg tgt gct ggt agg att ggc gtc ttt ccg gaa cct gaa tac    1008
```

```
Ala Ile Ala Cys Ala Gly Arg Ile Gly Val Phe Pro Glu Pro Glu Tyr
                325                 330                 335 gat ccc gtc atc caa att gcc aac gtt gtg agt att gct ggc gct aag      1056
Asp Pro Val Ile Gln Ile Ala Asn Val Val Ser Ile Ala Gly Ala Lys
            340                 345                 350 aaa cca ttc att cgt aat gtg ttt act ctg aat aca tgc tca ccc ata      1104
Lys Pro Phe Ile Arg Asn Val Phe Thr Leu Asn Thr Cys Ser Pro Ile
        355                 360                 365 aca ggt tca atg att ttt tcc cac gcc act gaa gag gaa atg ttg agc      1152
Thr Gly Ser Met Ile Phe Ser His Ala Thr Glu Glu Glu Met Leu Ser
370                 375                 380 aat tgg cgt aac ttt atc atc aaa gtt gat cct gat gtt atc att ggt      1200
Asn Trp Arg Asn Phe Ile Ile Lys Val Asp Pro Asp Val Ile Ile Gly
385                 390                 395                 400 tat aat act aca aat ttt gat atc cct tat ctt tta aac cgt gca aag      1248
Tyr Asn Thr Thr Asn Phe Asp Ile Pro Tyr Leu Leu Asn Arg Ala Lys
            405                 410                 415 gcg cta aag gtg aat gat ttc cca tat ttt gga agg tta aaa acc gtt      1296
Ala Leu Lys Val Asn Asp Phe Pro Tyr Phe Gly Arg Leu Lys Thr Val
        420                 425                 430 aag caa gaa att aaa gag tct gtg ttc tct tcg aag gct tat ggt aca      1344
Lys Gln Glu Ile Lys Glu Ser Val Phe Ser Ser Lys Ala Tyr Gly Thr
    435                 440                 445 aga gaa acc aaa aat gtc aat att gac ggc cga tta cag ttg gat ctt      1392
Arg Glu Thr Lys Asn Val Asn Ile Asp Gly Arg Leu Gln Leu Asp Leu
450                 455                 460 ttg caa ttt att cag cgt gag tat aaa cta aga tcc tac acg ttg aat      1440
Leu Gln Phe Ile Gln Arg Glu Tyr Lys Leu Arg Ser Tyr Thr Leu Asn
465                 470                 475                 480 gca gtc tct gcg cac ttt tta ggt gaa cag aag gag gat gta cat tat      1488
Ala Val Ser Ala His Phe Leu Gly Glu Gln Lys Glu Asp Val His Tyr
            485                 490                 495 agc atc att tct gat cta caa aat ggc gat agt gaa aca aga aga agg      1536
Ser Ile Ile Ser Asp Leu Gln Asn Gly Asp Ser Glu Thr Arg Arg Arg
        500                 505                 510 ttg gcc gtt tac tgt ttg aaa gac gcc tac ctg cct tta agg ctt atg      1584
Leu Ala Val Tyr Cys Leu Lys Asp Ala Tyr Leu Pro Leu Arg Leu Met
    515                 520                 525 gaa aaa cta atg gcg tta gtt aac tat aca gaa atg gct cgt gtt aca      1632
Glu Lys Leu Met Ala Leu Val Asn Tyr Thr Glu Met Ala Arg Val Thr
530                 535                 540 ggt gtg cca ttt tca tat tta cta gct cgt ggt caa caa att aaa gtt      1680
Gly Val Pro Phe Ser Tyr Leu Leu Ala Arg Gly Gln Gln Ile Lys Val
545                 550                 555                 560 gtt tct caa cta ttt cga aag tgc ctg gag att gat act gtg ata cct      1728
Val Ser Gln Leu Phe Arg Lys Cys Leu Glu Ile Asp Thr Val Ile Pro
            565                 570                 575 aac atg caa tct cag gcc tct gat gac caa tat gag ggt gcc act gtt      1776
Asn Met Gln Ser Gln Ala Ser Asp Asp Gln Tyr Glu Gly Ala Thr Val
        580                 585                 590 att gag cct att cgt ggt tat tac gat gta ccg att gca act ttg gat      1824
Ile Glu Pro Ile Arg Gly Tyr Tyr Asp Val Pro Ile Ala Thr Leu Asp
    595                 600                 605 ttc aat tct atg tat cca agt att atg atg gcg cac aac cta tgt tat      1872
Phe Asn Ser Met Tyr Pro Ser Ile Met Met Ala His Asn Leu Cys Tyr
610                 615                 620 aca aca ctt tgt aac aaa gct act gta gag aga ttg aat ctt aaa att      1920
Thr Thr Leu Cys Asn Lys Ala Thr Val Glu Arg Leu Asn Leu Lys Ile
625                 630                 635                 640
```

```
gac gaa gac tac gtc ata aca cct aat gga gat tat ttt gtt acc aca    1968
Asp Glu Asp Tyr Val Ile Thr Pro Asn Gly Asp Tyr Phe Val Thr Thr
                645                 650                 655 aaa aga agg cgt ggt ata tta cca att att ctg gat gaa tta ata agt    2016
Lys Arg Arg Arg Gly Ile Leu Pro Ile Ile Leu Asp Glu Leu Ile Ser
                660                 665                 670 gct aga aaa cgc gct aaa aaa gat ctg aga gat gag aag gat cca ttc    2064
Ala Arg Lys Arg Ala Lys Lys Asp Leu Arg Asp Glu Lys Asp Pro Phe
                675                 680                 685 aaa aga gat gtt tta aat ggt aga caa ttg gct ttg aag att tca gct    2112
Lys Arg Asp Val Leu Asn Gly Arg Gln Leu Ala Leu Lys Ile Ser Ala
                690                 695                 700 aac tct gtc tat ggt ttt aca gga gcg acg gtg ggt aaa ttg cca tgt    2160
Asn Ser Val Tyr Gly Phe Thr Gly Ala Thr Val Gly Lys Leu Pro Cys
705                 710                 715                 720 tta gcc att tct tca tct gtt act gct tat ggt cgt acc atg att tta    2208
Leu Ala Ile Ser Ser Ser Val Thr Ala Tyr Gly Arg Thr Met Ile Leu
                725                 730                 735 aaa act aaa acc gca gtc caa gaa aaa tat tgt ata aag aat ggt tat    2256
Lys Thr Lys Thr Ala Val Gln Glu Lys Tyr Cys Ile Lys Asn Gly Tyr
                740                 745                 750 aag cac gat gcc gtt gtg gtt tac ggt gac act gat tcc gtt atg gta    2304
Lys His Asp Ala Val Val Val Tyr Gly Asp Thr Asp Ser Val Met Val
                755                 760                 765 aag ttt ggt aca aca gat tta aag gaa gct atg gat ctt ggt acc gaa    2352
Lys Phe Gly Thr Thr Asp Leu Lys Glu Ala Met Asp Leu Gly Thr Glu
                770                 775                 780 gct gcc aaa tat gtc tcc act cta ttc aaa cat ccg att aac tta gaa    2400
Ala Ala Lys Tyr Val Ser Thr Leu Phe Lys His Pro Ile Asn Leu Glu
785                 790                 795                 800 ttt gaa aaa gca tac ttc cct tac ctt ttg ata aat aaa aag cgt tat    2448
Phe Glu Lys Ala Tyr Phe Pro Tyr Leu Leu Ile Asn Lys Lys Arg Tyr
                805                 810                 815 gca ggt tta ttc tgg act aat cct gac aag ttt gac aag ttg gac caa    2496
Ala Gly Leu Phe Trp Thr Asn Pro Asp Lys Phe Asp Lys Leu Asp Gln
                820                 825                 830 aaa ggc ctt gct tct gtc cgt cgt gat tcc tgt tcc ttg gtt tct att    2544
Lys Gly Leu Ala Ser Val Arg Arg Asp Ser Cys Ser Leu Val Ser Ile
                835                 840                 845 gtt atg aat aaa gtt tta aag aaa att tta att gaa aga aat gta gat    2592
Val Met Asn Lys Val Leu Lys Lys Ile Leu Ile Glu Arg Asn Val Asp
850                 855                 860 ggt gct tta gct ttt gtc aga gaa act atc aat gat att ctg cat aat    2640
Gly Ala Leu Ala Phe Val Arg Glu Thr Ile Asn Asp Ile Leu His Asn
865                 870                 875                 880 aga gta gat att tca aag ttg att ata tca aag acg tta gcc cca aat    2688
Arg Val Asp Ile Ser Lys Leu Ile Ile Ser Lys Thr Leu Ala Pro Asn
                885                 890                 895 tac aca aat cca cag ccg cac gcc gtt ttg gct gaa cgt atg aag agg    2736
Tyr Thr Asn Pro Gln Pro His Ala Val Leu Ala Glu Arg Met Lys Arg
                900                 905                 910 aga gag ggc gtt ggt cca aat gtt ggt gat cgt gtg gac tat gtc att    2784
Arg Glu Gly Val Gly Pro Asn Val Gly Asp Arg Val Asp Tyr Val Ile
                915                 920                 925 atc ggt ggt aat gat aaa ctt tac aat aga gca gaa gat cca tta ttt    2832
Ile Gly Gly Asn Asp Lys Leu Tyr Asn Arg Ala Glu Asp Pro Leu Phe
                930                 935                 940 gta cta gaa aac aat att caa gtg gat tcg cgc tat tat tta act aat    2880
Val Leu Glu Asn Asn Ile Gln Val Asp Ser Arg Tyr Tyr Leu Thr Asn
945                 950                 955                 960
```

```
caa tta caa aat cca atc att agt att gtt gca cct att att ggc gac    2928
Gln Leu Gln Asn Pro Ile Ile Ser Ile Val Ala Pro Ile Ile Gly Asp
            965                 970                 975 aaa cag gcg aac ggt atg ttc gtt gtg aaa tcc att aaa att aac aca    2976
Lys Gln Ala Asn Gly Met Phe Val Val Lys Ser Ile Lys Ile Asn Thr
        980                 985                 990 ggc tct caa aaa gga ggc ttg atg agc ttt att aaa aaa gtt gag gct    3024
Gly Ser Gln Lys Gly Gly Leu Met Ser Phe Ile Lys Lys Val Glu Ala
    995                 1000                1005 tgt aaa agt tgt aaa ggt ccg ttg agg aaa ggt gaa ggc cct ctt        3069
Cys Lys Ser Cys Lys Gly Pro Leu Arg Lys Gly Glu Gly Pro Leu
1010                1015                1020 tgt tca aac tgt cta gca agg tct gga gaa tta tac ata aag gca        3114
Cys Ser Asn Cys Leu Ala Arg Ser Gly Glu Leu Tyr Ile Lys Ala
    1025                1030                1035 tta tac gat gtc aga gat tta gag gaa aaa tac tca aga tta tgg        3159
Leu Tyr Asp Val Arg Asp Leu Glu Glu Lys Tyr Ser Arg Leu Trp
1040                1045                1050 aca caa tgc caa agg tgc gct ggt aac tta cat agt gaa gtt ttg        3204
Thr Gln Cys Gln Arg Cys Ala Gly Asn Leu His Ser Glu Val Leu
    1055                1060                1065 tgt tca aat aag aac tgt gac att ttt tat atg cgg gtt aag gtt        3249
Cys Ser Asn Lys Asn Cys Asp Ile Phe Tyr Met Arg Val Lys Val
1070                1075                1080 aaa aaa gag ctg cag gag aaa gta gaa caa tta agc aaa tgg taa        3294
Lys Lys Glu Leu Gln Glu Lys Val Glu Gln Leu Ser Lys Trp
    1085                1090                1095

<210> SEQ ID NO 25
<211> LENGTH: 1097
<212> TYPE: PRT
<213> ORGANISM: Saccharomyces cerevisiae

<400> SEQUENCE: 25

Met Ser Glu Lys Arg Ser Leu Pro Met Val Asp Val Lys Ile Asp Asp
1               5                   10                  15

Glu Asp Thr Pro Gln Leu Glu Lys Lys Ile Lys Arg Gln Ser Ile Asp
            20                  25                  30

His Gly Val Gly Ser Glu Pro Val Ser Thr Ile Glu Ile Ile Pro Ser
        35                  40                  45

Asp Ser Phe Arg Lys Tyr Asn Ser Gln Gly Phe Lys Ala Lys Asp Thr
    50                  55                  60

Asp Leu Met Gly Thr Gln Leu Glu Ser Thr Phe Glu Gln Asp Val Ser
65                  70                  75                  80

Gln Met Glu His Asp Met Ala Asp Gln Glu Glu His Asp Leu Ser Ser
                85                  90                  95

Phe Glu Arg Lys Lys Leu Pro Thr Asp Phe Asp Pro Ser Leu Tyr Asp
            100                 105                 110

Ile Ser Phe Gln Gln Ile Asp Ala Glu Gln Ser Val Leu Asn Gly Ile
        115                 120                 125

Lys Asp Glu Asn Thr Ser Thr Val Val Arg Phe Phe Gly Val Thr Ser
    130                 135                 140

Glu Gly His Ser Val Leu Cys Asn Val Thr Gly Phe Lys Asn Tyr Leu
145                 150                 155                 160

Tyr Val Pro Ala Pro Asn Ser Ser Asp Ala Asn Asp Gln Glu Gln Ile
                165                 170                 175

Asn Lys Phe Val His Tyr Leu Asn Glu Thr Phe Asp His Ala Ile Asp
```

-continued

```
                180             185             190
Ser Ile Glu Val Val Ser Lys Gln Ser Ile Trp Gly Tyr Ser Gly Asp
            195                 200                 205
Thr Lys Leu Pro Phe Trp Lys Ile Tyr Val Thr Tyr Pro His Met Val
        210                 215                 220
Asn Lys Leu Arg Thr Ala Phe Glu Arg Gly His Leu Ser Phe Asn Ser
225                 230                 235                 240
Trp Phe Ser Asn Gly Thr Thr Thr Tyr Asp Asn Ile Ala Tyr Thr Leu
                245                 250                 255
Arg Leu Met Val Asp Cys Gly Ile Val Gly Met Ser Trp Ile Thr Leu
            260                 265                 270
Pro Lys Gly Lys Tyr Ser Met Ile Glu Pro Asn Asn Arg Val Ser Ser
        275                 280                 285
Cys Gln Leu Glu Val Ser Ile Asn Tyr Arg Asn Leu Ile Ala His Pro
    290                 295                 300
Ala Glu Gly Asp Trp Ser His Thr Ala Pro Leu Arg Ile Met Ser Phe
305                 310                 315                 320
Ala Ile Ala Cys Ala Gly Arg Ile Gly Val Phe Pro Glu Pro Glu Tyr
                325                 330                 335
Asp Pro Val Ile Gln Ile Ala Asn Val Val Ser Ile Ala Gly Ala Lys
            340                 345                 350
Lys Pro Phe Ile Arg Asn Val Phe Thr Leu Asn Thr Cys Ser Pro Ile
        355                 360                 365
Thr Gly Ser Met Ile Phe Ser His Ala Thr Glu Glu Met Leu Ser
    370                 375                 380
Asn Trp Arg Asn Phe Ile Ile Lys Val Asp Pro Asp Val Ile Ile Gly
385                 390                 395                 400
Tyr Asn Thr Thr Asn Phe Asp Ile Pro Tyr Leu Leu Asn Arg Ala Lys
                405                 410                 415
Ala Leu Lys Val Asn Asp Phe Pro Tyr Phe Gly Arg Leu Lys Thr Val
            420                 425                 430
Lys Gln Glu Ile Lys Glu Ser Val Phe Ser Ser Lys Ala Tyr Gly Thr
        435                 440                 445
Arg Glu Thr Lys Asn Val Asn Ile Asp Gly Arg Leu Gln Leu Asp Leu
    450                 455                 460
Leu Gln Phe Ile Gln Arg Glu Tyr Lys Leu Arg Ser Tyr Thr Leu Asn
465                 470                 475                 480
Ala Val Ser Ala His Phe Leu Gly Glu Gln Lys Glu Asp Val His Tyr
                485                 490                 495
Ser Ile Ile Ser Asp Leu Gln Asn Gly Asp Ser Glu Thr Arg Arg Arg
            500                 505                 510
Leu Ala Val Tyr Cys Leu Lys Asp Ala Tyr Leu Pro Leu Arg Leu Met
        515                 520                 525
Glu Lys Leu Met Ala Leu Val Asn Tyr Thr Glu Met Ala Arg Val Thr
    530                 535                 540
Gly Val Pro Phe Ser Tyr Leu Leu Ala Arg Gly Gln Gln Ile Lys Val
545                 550                 555                 560
Val Ser Gln Leu Phe Arg Lys Cys Leu Glu Ile Asp Thr Val Ile Pro
                565                 570                 575
Asn Met Gln Ser Gln Ala Ser Asp Asp Gln Tyr Glu Gly Ala Thr Val
            580                 585                 590
Ile Glu Pro Ile Arg Gly Tyr Tyr Asp Val Pro Ile Ala Thr Leu Asp
        595                 600                 605
```

-continued

Phe Asn Ser Met Tyr Pro Ser Ile Met Met Ala His Asn Leu Cys Tyr
    610                 615                 620
Thr Thr Leu Cys Asn Lys Ala Thr Val Glu Arg Leu Asn Leu Lys Ile
625                 630                 635                 640
Asp Glu Asp Tyr Val Ile Thr Pro Asn Gly Asp Tyr Phe Val Thr Thr
                645                 650                 655
Lys Arg Arg Arg Gly Ile Leu Pro Ile Ile Leu Asp Glu Leu Ile Ser
            660                 665                 670
Ala Arg Lys Arg Ala Lys Lys Asp Leu Arg Asp Glu Lys Asp Pro Phe
        675                 680                 685
Lys Arg Asp Val Leu Asn Gly Arg Gln Leu Ala Leu Lys Ile Ser Ala
    690                 695                 700
Asn Ser Val Tyr Gly Phe Thr Gly Ala Thr Val Gly Lys Leu Pro Cys
705                 710                 715                 720
Leu Ala Ile Ser Ser Val Thr Ala Tyr Gly Arg Thr Met Ile Leu
                725                 730                 735
Lys Thr Lys Thr Ala Val Gln Glu Lys Tyr Cys Ile Lys Asn Gly Tyr
            740                 745                 750
Lys His Asp Ala Val Val Tyr Gly Asp Thr Asp Ser Val Met Val
        755                 760                 765
Lys Phe Gly Thr Thr Asp Leu Lys Glu Ala Met Asp Leu Gly Thr Glu
    770                 775                 780
Ala Ala Lys Tyr Val Ser Thr Leu Phe Lys His Pro Ile Asn Leu Glu
785                 790                 795                 800
Phe Glu Lys Ala Tyr Phe Pro Tyr Leu Leu Ile Asn Lys Lys Arg Tyr
                805                 810                 815
Ala Gly Leu Phe Trp Thr Asn Pro Asp Lys Phe Asp Lys Leu Asp Gln
            820                 825                 830
Lys Gly Leu Ala Ser Val Arg Arg Asp Ser Cys Ser Leu Val Ser Ile
        835                 840                 845
Val Met Asn Lys Val Leu Lys Lys Ile Leu Ile Glu Arg Asn Val Asp
    850                 855                 860
Gly Ala Leu Ala Phe Val Arg Glu Thr Ile Asn Asp Ile Leu His Asn
865                 870                 875                 880
Arg Val Asp Ile Ser Lys Leu Ile Ile Ser Lys Thr Leu Ala Pro Asn
                885                 890                 895
Tyr Thr Asn Pro Gln Pro His Ala Val Leu Ala Glu Arg Met Lys Arg
            900                 905                 910
Arg Glu Gly Val Gly Pro Asn Val Gly Asp Arg Val Asp Tyr Val Ile
        915                 920                 925
Ile Gly Gly Asn Asp Lys Leu Tyr Asn Arg Ala Glu Asp Pro Leu Phe
    930                 935                 940
Val Leu Glu Asn Asn Ile Gln Val Asp Ser Arg Tyr Tyr Leu Thr Asn
945                 950                 955                 960
Gln Leu Gln Asn Pro Ile Ile Ser Ile Val Ala Pro Ile Ile Gly Asp
                965                 970                 975
Lys Gln Ala Asn Gly Met Phe Val Val Lys Ser Ile Lys Ile Asn Thr
            980                 985                 990
Gly Ser Gln Lys Gly Gly Leu Met Ser Phe Ile Lys Lys Val Glu Ala
        995                 1000                1005
Cys Lys Ser Cys Lys Gly Pro Leu Arg Lys Gly Glu Gly Pro Leu
    1010                1015                1020

| Cys | Ser | Asn | Cys | Leu | Ala | Arg | Ser | Gly | Glu | Leu | Tyr | Ile | Lys | Ala |
|---|---|---|---|---|---|---|---|---|---|---|---|---|---|---|
| | 1025 | | | | 1030 | | | | | 1035 | | | | |

| Leu | Tyr | Asp | Val | Arg | Asp | Leu | Glu | Glu | Lys | Tyr | Ser | Arg | Leu | Trp |
|---|---|---|---|---|---|---|---|---|---|---|---|---|---|---|
| 1040 | | | | | 1045 | | | | | 1050 | | | | |

| Thr | Gln | Cys | Gln | Arg | Cys | Ala | Gly | Asn | Leu | His | Ser | Glu | Val | Leu |
|---|---|---|---|---|---|---|---|---|---|---|---|---|---|---|
| | 1055 | | | | 1060 | | | | | 1065 | | | | |

| Cys | Ser | Asn | Lys | Asn | Cys | Asp | Ile | Phe | Tyr | Met | Arg | Val | Lys | Val |
|---|---|---|---|---|---|---|---|---|---|---|---|---|---|---|
| | 1070 | | | | 1075 | | | | | 1080 | | | | |

| Lys | Lys | Glu | Leu | Gln | Glu | Lys | Val | Glu | Gln | Leu | Ser | Lys | Trp |
|---|---|---|---|---|---|---|---|---|---|---|---|---|---|
| 1085 | | | | | 1090 | | | | | 1095 | | | |

<210> SEQ ID NO 26
<211> LENGTH: 23
<212> TYPE: DNA
<213> ORGANISM: Artificial
<220> FEATURE:
<223> OTHER INFORMATION: primer

<400> SEQUENCE: 26
gtccaaagta ccaaactcga cgt                                      23

<210> SEQ ID NO 27
<211> LENGTH: 24
<212> TYPE: DNA
<213> ORGANISM: Artificial
<220> FEATURE:
<223> OTHER INFORMATION: primer

<400> SEQUENCE: 27
cgtaatctgg aacatcgtat gggt                                     24

<210> SEQ ID NO 28
<211> LENGTH: 30
<212> TYPE: DNA
<213> ORGANISM: Artificial
<220> FEATURE:
<223> OTHER INFORMATION: primer

<400> SEQUENCE: 28
aaatctagag cgcagcgagt cagtgagcga                               30

<210> SEQ ID NO 29
<211> LENGTH: 34
<212> TYPE: DNA
<213> ORGANISM: Artificial
<220> FEATURE:
<223> OTHER INFORMATION: primer

<400> SEQUENCE: 29
aaaactgcag caactgttgg gaagggcgat cggt                          34

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
cagaggtcgc ctgacgcata tacct                                    25

<210> SEQ ID NO 31
<211> LENGTH: 31
<212> TYPE: DNA

<213> ORGANISM: Artificial
<220> FEATURE:
<223> OTHER INFORMATION: primer

<400> SEQUENCE: 31
aagagctcat gtctaggaag ttgtcccacc t                           31

<210> SEQ ID NO 32
<211> LENGTH: 49
<212> TYPE: DNA
<213> ORGANISM: Artificial
<220> FEATURE:
<223> OTHER INFORMATION: primer

<400> SEQUENCE: 32
caaaactaac atgttcagct tgaaagcatc gacggtatcg ataagcttg        49

<210> SEQ ID NO 33
<211> LENGTH: 49
<212> TYPE: DNA
<213> ORGANISM: Artificial
<220> FEATURE:
<223> OTHER INFORMATION: primer

<400> SEQUENCE: 33
gccaaaccaa ccgcattgtt gcccaaatcg ctctagaact agtggatcc        49

<210> SEQ ID NO 34
<211> LENGTH: 49
<212> TYPE: DNA
<213> ORGANISM: Artificial
<220> FEATURE:
<223> OTHER INFORMATION: primer

<400> SEQUENCE: 34
atttaatcca aataaaattc aaacaaaaac caaaactaac atgttcagc        49

<210> SEQ ID NO 35
<211> LENGTH: 49
<212> TYPE: DNA
<213> ORGANISM: Artificial
<220> FEATURE:
<223> OTHER INFORMATION: primer

<400> SEQUENCE: 35
agtaagaaaa gtttagctca aattgctttg gccaaaccaa ccgcattgt        49

<210> SEQ ID NO 36
<211> LENGTH: 30
<212> TYPE: DNA
<213> ORGANISM: Artificial
<220> FEATURE:
<223> OTHER INFORMATION: primer

<400> SEQUENCE: 36
gagaagccta ccacgtaagg gaagaataac                             30

<210> SEQ ID NO 37
<211> LENGTH: 30
<212> TYPE: DNA
<213> ORGANISM: Artificial
<220> FEATURE:
<223> OTHER INFORMATION: primer

<400> SEQUENCE: 37
cccgcatata atgacattat gggcagcagc                             30

<210> SEQ ID NO 38
<211> LENGTH: 49
<212> TYPE: DNA
<213> ORGANISM: Artificial
<220> FEATURE:
<223> OTHER INFORMATION: primer

<400> SEQUENCE: 38
ctaattctaa caagcaaaga tgaagttagc gacggtatcg ataagcttg                49

<210> SEQ ID NO 39
<211> LENGTH: 49
<212> TYPE: DNA
<213> ORGANISM: Artificial
<220> FEATURE:
<223> OTHER INFORMATION: primer

<400> SEQUENCE: 39
ctctcacttg atcaaagatt aaatcggtcg ctctagaact agtggatcc                49

<210> SEQ ID NO 40
<211> LENGTH: 49
<212> TYPE: DNA
<213> ORGANISM: Artificial
<220> FEATURE:
<223> OTHER INFORMATION: primer

<400> SEQUENCE: 40
cttcatcgcc aataaaaaaa caaactaaac ctaattctaa caagcaaag                49

<210> SEQ ID NO 41
<211> LENGTH: 49
<212> TYPE: DNA
<213> ORGANISM: Artificial
<220> FEATURE:
<223> OTHER INFORMATION: primer

<400> SEQUENCE: 41
attaaataat attcaattta tcaagaatat ctctcacttg atcaaagat                49

<210> SEQ ID NO 42
<211> LENGTH: 30
<212> TYPE: DNA
<213> ORGANISM: Artificial
<220> FEATURE:
<223> OTHER INFORMATION: primer

<400> SEQUENCE: 42
gttacgtccc gttatattgg agttcttccc                                     30

<210> SEQ ID NO 43
<211> LENGTH: 30
<212> TYPE: DNA
<213> ORGANISM: Artificial
<220> FEATURE:
<223> OTHER INFORMATION: primer

<400> SEQUENCE: 43
agggactccg acttgtaacc tcgagacgcc                                     30

<210> SEQ ID NO 44
<211> LENGTH: 34
<212> TYPE: DNA
<213> ORGANISM: Artificial
<220> FEATURE:

<223> OTHER INFORMATION: primer

<400> SEQUENCE: 44
gggactagtg gtaactgtca gaccaagttt actc					34

<210> SEQ ID NO 45
<211> LENGTH: 22
<212> TYPE: DNA
<213> ORGANISM: Artificial
<220> FEATURE:
<223> OTHER INFORMATION: primer

<400> SEQUENCE: 45
ccacctgacg tctaagaaac ca					22

<210> SEQ ID NO 46
<211> LENGTH: 32
<212> TYPE: DNA
<213> ORGANISM: Artificial
<220> FEATURE:
<223> OTHER INFORMATION: primer

<400> SEQUENCE: 46
agaaagacgt caaaattcag ggcgcaaggg ct					32

<210> SEQ ID NO 47
<211> LENGTH: 33
<212> TYPE: DNA
<213> ORGANISM: Artificial
<220> FEATURE:
<223> OTHER INFORMATION: primer

<400> SEQUENCE: 47
aggactagtc agaagaactc gtcaagaagg cga					33

<210> SEQ ID NO 48
<211> LENGTH: 1140
<212> TYPE: DNA
<213> ORGANISM: Artificial
<220> FEATURE:
<223> OTHER INFORMATION: fusion protein alpha factor-bla

<400> SEQUENCE: 48
atgagatttc cttcaatttt tactgcagtt ttattcgcag catcctccgc attagctgct					60 ccagtcaaca ctacaacaga agatgaaacg gcacaaattc cggctgaagc tgtcatcggt					120 tactcagatt tagaagggga tttcgatgtt gctgttttgc cattttccaa cagcacaaat					180 aacgggttat tgtttataaa tactactatt gccagcattg ctgctaaaga agaaggggta					240 tctctcgaga aaagagaggc tgaagcttac gtagaattca tgagtattca acatttccgt					300 gtcgcccttt ttccttttt tgcggcattt tgccttcctg tttttgctca cccagaaacg					360 ctggtgaaag taaagatgc tgaagatcag ttgggtgcac gagtgggtta catcgaactg					420 gatctcaaca gcggtaagat ccttgagagt tttcgccccg aagaacgttt tccaatgatg					480 agcacttta aagttctgct atgtggcgcg gtattatccc gtattgacgc cgggcaagag					540 caactcggtc gccgcataca ctattctcag aatgacttgg ttgagtactc accagtcaca					600 gaaaagcatc ttacggatgg catgacagta agagaattat gcagtgctgc cataaccatg					660 agtgataaca ctgcggccaa cttacttctg acaacgatcg gaggaccgaa ggagctaacc					720 gcttttttgc acaacatggg ggatcatgta actcgccttg atcgttggga accggagctg					780 aatgaagcca taccaaacga cgagcgtgac accacgatgc ctgtagcaat ggcaacaacg					840

```
ttgcgcaaac tattaactgg cgaactactt actctagctt cccggcaaca attaatagac    900
tggatggagg cggataaagt tgcaggacca cttctgcgct cggcccttcc ggctggctgg    960
tttattgctg ataaatctgg agccggtgag cgtgggtctc gcggtatcat tgcagcactg   1020
gggccagatg gtaagccctc ccgtatcgta gttatctaca cgacggggag tcaggcaact   1080
atggatgaac gaaatagaca gatcgctgag ataggtgcct cactgattaa gcattggtaa   1140
```

<210> SEQ ID NO 49
<211> LENGTH: 30
<212> TYPE: DNA
<213> ORGANISM: Artificial
<220> FEATURE:
<223> OTHER INFORMATION: primer

<400> SEQUENCE: 49
gtttgttaac cgctgggcca ttctcatgaa                    30

<210> SEQ ID NO 50
<211> LENGTH: 30
<212> TYPE: DNA
<213> ORGANISM: Artificial
<220> FEATURE:
<223> OTHER INFORMATION: primer

<400> SEQUENCE: 50
gtttgacgtc caactgcatg gagatgagtc                    30

<210> SEQ ID NO 51
<211> LENGTH: 27
<212> TYPE: DNA
<213> ORGANISM: Artificial
<220> FEATURE:
<223> OTHER INFORMATION: primer

<400> SEQUENCE: 51
gtttgagctc atgcaataca aaaagac                       27

<210> SEQ ID NO 52
<211> LENGTH: 29
<212> TYPE: DNA
<213> ORGANISM: Artificial
<220> FEATURE:
<223> OTHER INFORMATION: primer

<400> SEQUENCE: 52
gtttcccggg cttgtcatcg tcatccttg                     29

<210> SEQ ID NO 53
<211> LENGTH: 28
<212> TYPE: DNA
<213> ORGANISM: Artificial
<220> FEATURE:
<223> OTHER INFORMATION: primer

<400> SEQUENCE: 53
gtttcccggg gcgaccttgg attcgtgg                      28

<210> SEQ ID NO 54
<211> LENGTH: 28
<212> TYPE: DNA
<213> ORGANISM: Artificial
<220> FEATURE:
<223> OTHER INFORMATION: primer

<400> SEQUENCE: 54
gttttctaga ctaccgccag gtgtcggt                                              28

<210> SEQ ID NO 55
<211> LENGTH: 28
<212> TYPE: DNA
<213> ORGANISM: Artificial
<220> FEATURE:
<223> OTHER INFORMATION: primer

<400> SEQUENCE: 55
aaagcggccg cagcgagtca gtgagcga                                              28

<210> SEQ ID NO 56
<211> LENGTH: 34
<212> TYPE: DNA
<213> ORGANISM: Artificial
<220> FEATURE:
<223> OTHER INFORMATION: primer

<400> SEQUENCE: 56
tttactagta tgatgtggtc tctacaggat ctga                                       34

<210> SEQ ID NO 57
<211> LENGTH: 1170
<212> TYPE: DNA
<213> ORGANISM: Artificial
<220> FEATURE:
<223> OTHER INFORMATION: fusion protein alpha factor-G9null

<400> SEQUENCE: 57

```
atgagatttc cttcaattt tactgcagtt ttattcgcag catcctccgc attagctgct      60
ccagtcaaca ctacaacaga agatgaaacg gcacaaattc cggctgaagc tgtcatcggt     120
tactcagatt tagaagggga tttcgatgtt gctgttttgc cattttccaa cagcacaaat     180
aacggggttat tgtttataaa tactactatt gccagcattg ctgctaaaga agaaggggta     240
tctctcgaga aaagagaggc tgaagcttac gtagaattca tggccttcag cggttcccag     300
gctccctacc tgagtccagc tgtccccttt tctggggacta ttcaaggagg tctccaggac     360
ggacttcaga tcactgtcaa tgggaccgtt ctcagctcca gtggaaccag gtttgctgtg     420
aactttcaga ctggcttcag tggaaatgac attgccttcc acttcaaccc tcggtttgaa     480
gatggagggt acgtggtgtg caacacgagg cagaacggaa gctggggcc gaggagagg      540
aagacacaca tgccttttcca gaaggggatg ccctttgacc tctgcttcct ggtgcagagc     600
tcagatttca aggtgatggt gaacgggatc ctcttcgtgc agtacttcca ccgcgtgccc     660
ttccaccgtg tggacaccat ctccgtcaat ggctctgtgc agctgtccta catcagcttc     720
cagcatatga ctcccgccat cccacctatg atgtaccccc accccgccta tccgatgcct     780
ttcatcacca ccattctggg agggctgtac ccatccaagt ccatcctcct gtcaggcact     840
gtcctgccca gtgctcagag gttccacatc aacctgtgct ctgggaacca catcgccttc     900
cacctgaacc ccgttttga tgagaatgct gtggtccgca cacccagat cgacaactcc     960
tggggggtctg aggagcgaag tctgccccga aaaatgccct tcgtccgtgg ccagagcttc    1020
tcagtgtgga tcttgtgtga agctcactgc ctcaaggtgg ccgtggatgg tcagcacctg    1080
tttgaatact accatcgcct gaggaacctg cccaccatca acagactgga agtgggggc    1140
gacatccagc tgacccatgt gcagacatag                                      1170
```

-continued

<210> SEQ ID NO 58
<211> LENGTH: 29
<212> TYPE: DNA
<213> ORGANISM: Saccharomyces cerevisiae

<400> SEQUENCE: 58
caaaactaac atgttcagct tgaaagcat                                29

<210> SEQ ID NO 59
<211> LENGTH: 29
<212> TYPE: DNA
<213> ORGANISM: Saccharomyces cerevisiae

<400> SEQUENCE: 59
gatttgggca acaatgcggt tggtttggc                                29

<210> SEQ ID NO 60
<211> LENGTH: 59
<212> TYPE: DNA
<213> ORGANISM: Saccharomyces cerevisiae

<400> SEQUENCE: 60
atttaatcca ataaaattc aaacaaaaac caaaactaac atgttcagct tgaaagcat   59

<210> SEQ ID NO 61
<211> LENGTH: 59
<212> TYPE: DNA
<213> ORGANISM: Saccharomyces cerevisiae

<400> SEQUENCE: 61
gatttgggca acaatgcggt tggtttggcc aaagcaattt gagctaaact tttcttact   59

<210> SEQ ID NO 62
<211> LENGTH: 29
<212> TYPE: DNA
<213> ORGANISM: Saccharomyces cerevisiae

<400> SEQUENCE: 62
ctaattctaa caagcaaaga tgaagttag                                29

<210> SEQ ID NO 63
<211> LENGTH: 29
<212> TYPE: DNA
<213> ORGANISM: Saccharomyces cerevisiae

<400> SEQUENCE: 63
gaccgattta atctttgatc aagtgagag                                29

<210> SEQ ID NO 64
<211> LENGTH: 59
<212> TYPE: DNA
<213> ORGANISM: Saccharomyces cerevisiae

<400> SEQUENCE: 64
cttcatcgcc aataaaaaaa caaactaaac ctaattctaa caagcaaaga tgaagttag   59

<210> SEQ ID NO 65
<211> LENGTH: 59
<212> TYPE: DNA
<213> ORGANISM: Saccharomyces cerevisiae

<400> SEQUENCE: 65
gaccgattta atctttgatc aagtgagaga tattcttgat aaattgaata ttatttaat   59

SUGAR-CHAIN MODIFIED YEAST AND METHOD FOR PRODUCING GLYCOPROTEIN USING THE SAME

BACKGROUND OF THE INVENTION

Field of the Invention

Techniques for adding sugar chains to a recombinant protein are extremely important for the development and production of proteins serving as medical raw materials. The demand for glycoprotein drugs as many therapeutic agents for diseases such as antibody drugs is expanding. However, conventional methods for producing glycoprotein drugs using cultured animal cells are problematic in that: the methods take much time for the establishment of target strains; a high-level culture facility is required; serum component safety must be ensured; and sugar chains cannot be freely added. Hence, instead of animal cells, the development of alternative hosts capable of safely and inexpensively supplying high-quality glycoproteins as raw materials for pharmaceutical products has been desired. To meet this social need, many groups around the world are attempting to develop hosts capable of producing glycoproteins. For example, GlycoFi, ASPEX, and others in the U.S. are developing glycoprotein production systems using yeast as a host.

Sugar chains exhibit species-specific structures. When a pharmaceutical product for humans is produced using a glycoprotein production system wherein a non-human host is used, a sugar chain should be converted into a human-type sugar chain. However, procedures for the conversion require the genetic modification of the host, and such modification lowers the productivity and growth ability of the host. This is the same barrier as that for development of an alternative host.

Addition of O-linked sugar chains induces damaged conformation or secretion of the thus produced protein. Hence, suppressed O-glycosylation leads to high-quality and high-yield glycoprotein production. However, such sugar chain control is very difficult. Currently, N-linked sugar chain modification is under intensive study, and O-linked sugar chain modification is merely carried out. Tanner et al., have disclosed a method for reducing the binding of O-linked sugar chains in a recombinant protein by deleting PMT1 and PMT2 genes involved in O-glycosylation in host cells (U.S. Pat. No. 5,714,377). However, the PMT1 and PMT2 genes are important for the growth ability of host cells, such that only the lack of either one significantly reduces the growth ability of the host. Therefore, with the method, in general, the level of the addition of O-linked sugar chains to a protein can be reduced, but the production of a target protein in a sufficient amount is difficult. Accordingly a method for producing a recombinant protein while reducing the level of O-linked glycosylation with the use of a PMT inhibitor has been developed (WO2007/061631). However, the method requires the adjustment of conditions for treatment with the PMT inhibitor in order to make it possible to reduce the level of O-linked glycosylation, while ensuring growth ability. Therefore, the method should be further improved for effective protein production.

The present inventors have already developed a YAB100 yeast strain ($Man_8GlcNAc_2$ sugar chain-producing strain) (JP Patent Publication (Kokai) No. 2008-220172 A) that is capable of efficiently producing a human-type glycoprotein and has good growth ability and protein production ability. This was achieved through the use of a human-type glycoprotein-producing yeast (TIY20 strain) as a parent strain that had been modified by disrupting an enzyme gene (e.g., an α-1,6-mannosyltransferase gene) involved in outer sugar chain synthesis, so as to suppress outer sugar chain production unique to yeast and to produce the $Man_8GlcNAc_2$ sugar chain. However, the development of a strain for suppression of O-glycosylation has not proceeded.

Therefore, the development of an alternative host that can synthesize human-type N-linked sugar chains, inhibit O-glycosylation reactions, and maintain sufficient growth ability is still desired.

SUMMARY OF THE INVENTION

An object of the present invention is to provide yeast that can suppress O-linked sugar chain production while maintaining sufficient growth ability and can synthesize a human-type N-linked sugar chain $Man_5GlcNAc_2$.

As a result of intensive studies to achieve the above object, the present inventors have discovered a yeast strain with good growth ability, which is derived from yeast that: has an α-1,2-mannosidase I gene that has been introduced thereinto; is functionally deficient in a protein-O-mannosyltransferase gene; and is also functionally deficient in a gene (OCH1) encoding α-1,6 mannosyltransferase for carrying out an initial sugar chain elongation/addition reaction, a gene (MNN1) encoding an α-1,3 mannosyltransferase for adding mannose to a non-reduced sugar chain end, and a gene (MNN4) for regulating the addition of mannose-1-phosphate, from among genes involved in biosynthesis of an outer sugar chain specific to yeast. Thus, they have completed the present invention.

The present invention encompasses the following [1] to [15].

[1] A mutant yeast which has an ability to produce N-linked sugar chains of $Man_5GlcNAc_2$ and a decreased ability to produce O-linked sugar chains, wherein the yeast is functionally deficient in a protein-O-mannosyltransferase gene, an α-1,6-mannosyltransferase gene, an α-1,3 mannosyltransferase gene and a mannose-1-phosphorylation regulating gene; and an α-1,2-mannosidase I gene is introduced.

[2] The mutant yeast according to [1] above, which is functionally deficient in at least one of protein-O-mannosyltransferase genes PMT1 and PMT2.

[3] The mutant yeast according to [2] above, wherein a decrease in the growth ability due to disruption of the protein-O-mannosyltransferase gene is suppressed.

[4] The mutant yeast according to [1] to [3] above, wherein an α-1,2-mannosidase I gene is re-introduced, thereby increasing the ability to produce N-linked sugar chains of $Man_5GlcNAc_2$.

[5] The mutant yeast according to [1] to [4] above, wherein the yeast is further functionally deficient in a protease gene.

[6] The mutant yeast according to [5] above, which is functionally deficient in at least one of protease genes PEP4 and PRB1.

[7] The mutant yeast according to [1] to [3] above, which is specified with accession number FERM BP-11469 or FERM BP-11470.

[8] The mutant yeast according to [4] above, which is specified with accession number FERM BP-11474.

[9] The mutant yeast according to [5] or [6] above, which is specified with accession number FERM BP-11472 or FERM BP-11473.

[10] A mutant yeast which has an ability to produce N-linked sugar chains of $Man_5GlcNAc_2$ and further has an ability to produce N-linked sugar chains of $GlcNAc_1Man_5GlcNAc_2$, wherein the yeast is functionally deficient in an α-1,6-mannosyltransferase gene, an α-1,3 mannosyltransferase gene and a mannose-1-phosphorylation regulating gene; and an N-acetylglucosaminetransferase I gene and an α-1,2-mannosidase I gene are introduced.

[11] The mutant yeast according to [10] above, which is specified with accession number FERM BP-11471.

[12] A mutant yeast which has an ability to produce N-linked sugar chains of Man$_5$GlcNAc$_2$, wherein the yeast is functionally deficient in an α-1,6-mannosyltransferase gene, an α-1,3 mannosyltransferase gene and a mannose-1-phosphorylation regulating gene; an α-1,2-mannosidase I gene is introduced; and the ability to produce and secrete proteins is increased.

[13] The mutant yeast according to [12] above, wherein the yeast is further functionally deficient in a protease gene.

[14] The mutant yeast according to [12] or [13] above, which is specified with accession number FERM BP-11475.

[15] A method for producing a glycoprotein, comprising introducing DNA encoding the amino acid sequence of a glycoprotein of interest into the mutant yeast of [1] to [14] above to produce a transformed yeast, and then expressing a recombinant protein; and use of the mutant yeast according to [1] to [14] above for production of a glycoprotein.

A mammalian-type N-linked glycosylated protein can be efficiently produced with the use of the present invention, while suppressing O-glycosylation.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 2A shows the results for the YAB100 strain and FIG. 2B shows the results for the YFY20 strain.

FIG. 4A shows the growth state of cells cultured at 30° C., FIG. 4B shows the same cultured at 35° C., and FIG. 4C shows the same cultured at 37° C. Furthermore, FIG. 4D shows the growth state of cells cultured in medium containing hygromycin B (3 μg/ml) and FIG. 4E shows the same cultured in medium containing Calcofluor white (CFW).

FIG. 6A shows the results for the YFY20 strain and FIG. 6B shows the results for the YKT1 strain.

FIG. 7A shows the results for the YFY24 strain and FIG. 2B shows the results for the YKT4 strain.

FIG. 10A shows the results for a non-transformed YFY20 strain and FIG. 10B shows the results for the YFY20-1 strain transformed with pYF048 and pYF053 via introduction thereof.

DETAILED DESCRIPTION OF THE PREFERRED EMBODIMENTS

The present invention will be described in more detail as follows.

1. Modification of Sugar Chain Structure

The present invention relates to mutant yeast which has an ability to produce an N-linked sugar chain (the sugar chain added to an asparagine residue of a protein) having the same structure as sugar chains produced by mammalian cells and has sufficient growth ability. The present invention also relates to a method for using the mutant yeast for sugar chain and glycoprotein production.

Sugar chains added to glycoproteins are broadly classified into N-linked (Asn-linked), mucin-type, O-linked (O-GlcNAc-type), GPI-anchor-type, and proteoglycan-type sugar chains (Makoto Takeuchi, Glycobiology series 5, Glycotechnology, Ed., Akira Kobata, Senichiro Hakomori, and Katsutaka Nagai, Kodansha Scientific Ltd., 191-208 (1994)), each of which has its unique biosynthesis pathway and is responsible for individual physiologic functions.

Through biosynthesis of an N-linked sugar chain, firstly, an M8 high-mannose-type sugar chain (Man$_8$GlcNAc$_2$) comprising 8 mannose (Man) residues and 2 N-acetylglucosamine (GlcNAc) residues is synthesized in a form binding to an asparagine residue (Asn) of a protein. Such a protein containing the high-mannose-type sugar chain is transported to the Golgi body so as to be subjected to various modifications. Such modifications in the Golgi body differ significantly between yeast and mammals (Gemmill, T. R. and Trimble, R. B., Biochim. Biophys. Acta., 1426, 227 (1999)).

In many cases in mammalian cells, α-mannosidase I acts on the M8 high-mannose-type sugar chain to cleave several mannose residues, so that a high-mannose-type sugar chain such as $Man_5GlcNAc_2$ is generated. N-acetylglucosaminetransferase I (GnT-I) acts on an M5 high-mannose-type sugar chain ($Man_5GlcNAc_2$) resulting from cleavage of 3 mannose residues, so that one residue of N-acetylglucosamine is transferred and a sugar chain of $GlcNAc_1Man_5GlcNAc_2$ is generated. The thus generated sugar chain is referred to as a hybrid-type sugar chain. Furthermore, α-mannosidase II and GnT-II act on the hybrid type sugar chain, so that a sugar chain having a complex-type sugar chain structure, which is of $GlcNAc_2Man_3GlcNAc_2$, is generated. Nearly a dozen types of glycosyltransferase groups act on the resulting sugar chain, so that various mammalian sugar chains are generated.

Figure 1:
FIG. 1 schematically shows a typical example of modification of a yeast sugar chain structure, wherein "Man" indicates a mannose residue, "P" indicates a phosphate group, "GlcNAc" indicates an N-acetylglucosamine residue, "Asn" indicates an aspartic acid residue in a polypeptide, and "Ser/Thr" indicates a serine residue or a threonine residue in a polypeptide.

Meanwhile, in yeast, a sugar chain (outer sugar chain) containing several to at least 100 mannose residues are added to the M8 high-mannose-type sugar chain (FIG. 1A). Biosynthesis of an outer sugar chain in yeast is as follows. First, α-1,6 mannosyltransferase (OCH1 gene product; Och1) acts to cause an elongation initiation reaction (whereby mannose residues are added at α-1,6 linkage) in the M8 high-mannose-type sugar chain (Nakayama et al., EMBO J., 11, 2511-2519 (1992)). Furthermore, α-1,6 mannosyltransferase causes reactions by which mannose residues are consecutively elongated via α-1,6 linkage, so that the backbone of an outer sugar chain is formed. Moreover, in yeast, α-1,3 mannosyltransferase (MNN1 gene product; Mnn1) acts to add an α-1,3-linked mannose residue to the terminal mannose residue of an M8 high-mannose-type sugar chain (Nakanishi-Shindo et al., J. Biol. Chem., 268, 26338-26345 (1993)). Also in yeast, it is known that mannose-1-phosphate is added to a high-mannose-type sugar chain portion and an outer sugar chain portion (generation of acidic sugar chains). In this reaction, mannosephosphatetransferase (MNN6 gene product; Mnn6) and a positive regulator of mannosephosphatetransferase (MNN4 gene product; Mnn4) are involved (Wang et al., J. Biol. Chem., 272, 18117-18124 (1997); Odani et al., Glycobiology, 6, 805-810 (1996); Odani et al., FEBS letters, 420, 186-190 (1997)). In many cases, such an outer sugar chain unique to yeast is problematic in that it not only impairs the homogeneity of protein products, makes protein purification difficult, and decreases specific activity, but also exhibits strong immunogenicity in mammals, for example.

Furthermore, in yeast, protein-O-mannosyltransferase (gene products of PMT1 to 7) acts to add an O-linked sugar chain to Ser/Thr residues of a protein (FIG. 1B). As described above, an O-linked sugar chain also causes inconvenience when it is added to a protein upon recombination production of a mammalian glycoprotein.

Hence, in the present invention, for the production of a mammalian sugar chain-bound protein using yeast, functional deficiency (in general, gene disruption or some mutagenesis) is induced in an α-1,6 mannosyltransferase gene (typically, OCH1 gene), an α-1,3 mannosyltransferase gene (typically, MNN1 gene), and a mannose-1-phosphorylation regulating gene (typically, MNN4 gene) of yeast, so as to inhibit the addition of outer sugar chains. Moreover, an α-1,2-mannosidase I gene is introduced, so as to inhibit α-1,2 linkage of mannose residues. Thus, $Man_5GlcNAc_2$ sugar chain production is accelerated (FIG. 1D). Simultaneously, functional deficiency is induced in a protein-O-mannosyltransferase gene, so as to reduce the level of the addition of O-linked sugar chains (FIG. 1E).

Also in another embodiment of the present invention for production of a mammalian-type sugar chain-bound protein using yeast, functional deficiency (in general, gene disruption or some mutagenesis) is induced in an α-1,6 mannosyltransferase gene (typically, OCH1 gene), an α-1,3 mannosyltransferase gene (typically, MNN1 gene), and a mannose-1-phosphorylation regulating gene, typically, MNN4 gene, of yeast, so as to inhibit the addition of outer sugar chains. An α-1,2-mannosidase I gene is further introduced, so as to inhibit α-1,2 linkage of mannose residues. Furthermore, an N-acetylglucosaminetransferase I gene is introduced, so as to induce the transfer of N-acetylglucosamine (GlcNAc) to the terminal mannose residue. Thus, the production of the sugar chain of $GlcNAc_1Man_5GlcNAc_2$ is accelerated (FIG. 1F).

2. Preparation of Sugar-Chain Modified Yeast Strain

The present invention provides mutant yeast which has an ability to produce N-linked sugar chains of $Man_5GlcNAc_2$, but has a decreased ability to produce O-linked sugar chains, wherein the yeast has functional deficiency (i.e., gene disruption or some mutagenesis into the gene) in a protein-O-mannosyltransferase gene, an α-1,6-mannosyltransferase gene, an α-1,3 mannosyltransferase gene, and a mannose-1-phosphorylation regulating gene, and an α-1,2-mannosidase I gene is introduced.

Examples of "yeast" in the present invention include, but are not limited to, yeast belonging to the family Saccharomycetaceae and yeast belonging to the family Schizosaccharomycetaceae. "Yeast" in the present invention is preferably yeast belonging to the genus *Saccharomyces*. For example, budding yeast (*Saccharomyces cerevisiae*), fission yeast (*Schizosaccharomyces pombe*), and the like are more preferable.

The term "mutant yeast" in the specification refers to yeast wherein one or more endogenous genes are mutated or deleted compared with wild-type yeast, or, yeast wherein one or more foreign genes are introduced.

A protein-O-mannosyltransferase gene that is caused to be functionally deficient in the mutant yeast according to the present invention is an endogenous protein-O-mannosyltransferase gene existing in a host yeast genome. The protein-O-mannosyltransferase gene may be at least one gene selected from the group consisting of a PMT1 gene (in budding yeast, the ORF sequence ranges from positions 287059 to 289512 in the sequence under GenBank Accession No. NC_001136), a PMT2 gene (in budding yeast, the ORF sequence ranges from positions 106273 to 108552 in the sequence of NC_001133), a PMT3 gene (the ORF sequence ranges from positions 37 to 2298 in the sequence of X83797), a PMT4 gene (the ORF sequence ranges from positions 101 to 2389 in the sequence of X83798), a PMT5 gene (the ORF sequence ranges from positions 182 to 2413 in the sequence of X92759), a PMT6 gene (NM_001181328 (ORF sequence); encoded amino acid sequence: NP_011715), and a PMT7 gene (encoded amino acid sequence: Q06644), for example. Of these examples, at least one of PMT1 to PMT4 and PMT6 genes is preferable. Functional deficiency is more preferably caused in either the PMT1 gene or the PMT2 gene. Functional deficiency is even more preferably caused in both the PMT1 gene and the PMT2 gene.

The α-1,6 mannosyltransferase gene that is caused to be functionally deficient in the mutant yeast according the present invention is an endogenous α-1,6 mannosyltransferase gene, and it is preferably an OCH1 gene existing in a host yeast genome.

The mutant yeast according to the present invention further has functional deficiency in genes involved in biosynthesis of sugar chain structures unique to yeast, including an α-1,3-mannosyltransferase gene (preferably, the MNN1 gene) encoding an enzyme that adds mannose to a nonreducing end of a sugar chain and a mannose-1-phosphorylation regulating gene (preferably, the MNN4 gene) encoding an enzyme that regulates (i.e., accelerates) the addition of a mannose-1-phosphate group.

Such mutant yeast according to the present invention does not generate any outer sugar chain because of its functional deficiency in the α-1,6-mannosyltransferase gene, but can generate the sugar chain of Man$_5$GlcNAc$_2$ since the α-1,2 linkage of mannose residues is cleaved by the functions of the introduced α-1,2-mannosidase I gene (FIG. 1D). In the mutant yeast according to the present invention, its functional deficiency in the α-1,3-mannosyltransferase gene (preferably, MNN1 gene) and the mannose-1-phosphorylation regulating gene (preferably, MNN4 gene) suppresses the addition of an α-1,3-linked mannose residue to a sugar chain end and the generation of an acidic sugar chain. Furthermore, in the mutant yeast according to the present invention, its functional deficiency in the protein-O-mannosyltransferase gene reduces the level of the generation of O-linked sugar chains. Specifically, the yeast has decreased ability to produce O-linked sugar chains. Confirmation of such a modified sugar chain structure can be carried out by pyridylaminating a sugar chain sample obtained via cleavage of a mannoprotein extracted from cultured cells and then subjecting it to HPLC analysis, for example.

The mutant yeast according to the present invention further preferably has functional deficiency in other genes involved in biosynthesis of sugar chain structures unique to yeast. Examples of such a gene include mannose-1-phosphate group transferase genes (e.g., MNN6) for α-1,3-linked mannose residues of a high-mannose-type sugar chain and an outer sugar chain, other genes (e.g., MNN7, MNN8, MNN9, and MNN10) encoding enzymes involved in biosynthesis of outer sugar chains, and mannosetransferase genes (e.g., KRE2) responsible for an elongation reaction of O-linked sugar chains. The mutant yeast according to the present invention may further have functional deficiency in other endogenous genes not involved in sugar chain biosynthesis.

The term "functional deficiency (or functionally deficient) in a gene" in the present invention refers to the absence of the relevant gene encoding an active protein. Yeast strains that are functionally deficient in genes include not only gene-disrupted strains (gene-deleted strains), but also mutant strains in which genes have been mutated to encode proteins (inactive proteins) or polypeptides losing their activity as a result of nucleotide insertion into ORF, frame shift due to deletion mutation, amino acid substitution at the active center, or the like. When the gene is disrupted in a genome, this is also included in "functional deficiency" in a gene, even if a portion of the gene (e.g., transmembrane region-encoding sequence) is present in the genome or the like of host yeast, unless the portion encodes a partial protein retaining activity (e.g., enzyme activity).

Functional deficiency in a gene in a genome can be induced by a conventional method. As an example, gene disruption can be typically induced by a method using homologous recombination. For example, a plasmid is constructed so that a marker gene is inserted between the 5' side sequence and the 3' side sequence of a gene to be disrupted. The plasmid is introduced into host yeast cells and then host yeast cells are cultured. Thus, homologous recombination is induced between the gene to be disrupted in the host genome and the introduced plasmid, so that the marker gene is inserted into the gene. As a result, the gene is disrupted. For a gene disruption method based on homologous recombination, various arbitrary methods can be employed. For example, according to the method of Alani et al., (Alani. et al., Genetics, 116, 541-545 (1987)), a plasmid having a hisG-URA3-hisG expression cassette (marker gene) and the 5' side sequence and the 3' side sequence of a gene to be disrupted, which have been inserted to both sides of the cassette, is introduced into host cells. The hisG-URA3-hisG expression cassette is inserted into the genome via homologous recombination with the gene. Therefore, a gene-disrupted strain in which the gene has been disrupted can be obtained and the URA3 marker can be used for screening therefor. In addition, the sequences of various protein-O-mannosyltransferase genes, the α-1,6 mannosyltransferase gene (OCH1), the α-1,3-mannosyltransferase gene (MNN1), and the mannose-1-phosphorylation regulating gene (MNN4) are known in various organisms.

Introduction of a mutation into a gene to induce functional deficiency can be carried out by modification with the use of a mutagenesis method such as site-directed mutagenesis. Specifically, as site-directed mutagenesis, known techniques such as a Kunkel method and a Gapped duplex method or a method according thereto can be employed herein. Persons skilled in the art can easily carry out such mutagenesis using commercial site-directed mutagenesis kits (e.g., QuikChange$^{(R)}$ Site-Directed Mutagenesis Kit (Stratagene), Mutan$^{(R)}$-K (TAKARA BIO INC.), Mutan$^{(R)}$-Super Express Km (TAKARA BIO INC.), and PrimeSTAR$^{(R)}$ Mutagenesis Basal Kit (TAKARA BIO INC.)), for example.

An α-1,2-mannosidase I gene to be introduced into the mutant yeast according to the present invention may be derived from any organism and is not limited. The α-1,2-mannosidase I gene is preferably a fungal α-1,2-mannosidase I gene. The sequences of the α-1,2-mannosidase I genes of various organisms are known. Examples of a fungal α-1,2-mannosidase I gene include that of the genus *Aspergillus*, that of the genus *Saccharomyces*, that of the genus *Candida*, and that of the genus *Schizosaccharomyces*. In particular, the α-1,2-mannosidase I gene (msdS) of *Aspergillus saitoi* can be preferably used. Such an α-1,2-mannosidase I gene is preferably incorporated into a host genome, but this is not limited thereto.

An α-1,2-mannosidase I gene is also preferably introduced as a fusion gene that is prepared by fusing it to a site downstream of a sequence encoding a transmembrane region of a host yeast protein. In this case, the α-1,2-mannosidase I gene preferably lacks its natural N-terminus (e.g., transmembrane region). Thus, α-1,2-mannosidase I can be anchored onto yeast Golgi body. An original protein from which a transmembrane region to be fused is derived is preferably, a host yeast's natural transmembrane-type glycoprotein. Examples thereof include an OCH1 gene, MNN1, MNN4, MNN6, MNN7, MNN8, MNN9, and MNN10 genes, and a KRE2 gene. Such an original protein from which a transmembrane region to be fused is derived may be encoded by a functionally deficient gene in host yeast.

An α-1,2-mannosidase I gene may also be introduced into host yeast in a form further fused to any tag sequence such as an HA tag.

In general, a gene can be introduced by introducing a yeast expression vector (into which the relevant gene has been incorporated) into host yeast and then obtaining a transformant of host yeast. However, the method for gene introduction is not limited thereto. Examples of a yeast expression vector include a yeast episome plasmid abbreviated as YEp and a yeast replicating plasmid abbreviated as YRp. Such a yeast episome plasmid vector contains the sequence of a yeast's original 2μ plasmid, which is constructed so as to be able to replicate within host yeast cells with the use of the replication origin. Preferably the yeast episome expression vector contains at least an ARS sequence of the 2μ plasmid sequence of yeast, and can grow extrachromosomally within host yeast cells. Specific examples of a plasmid include YEp51, pYES2, YEp351, YEp352, and pREP. Moreover, a chromosomal integration vector YIp and an YCp vector having both an autonomous replication region (ARS: autonomously replicating sequence) and a centromere region (CEN) can be used herein. The above yeast expression vector is preferably a shuttle vector capable of growing within *Escherichia coli* so as to be able to carry out subcloning within recombinant *Escherichia coli* and is further preferably a vector containing a selection marker gene such as an ampicillin resistance gene. Also, the expression vector contains a marker gene with which a yeast clone can be selected based on auxotrophy or drug resistance when recombinant yeast is prepared. Examples of a marker gene include HIS3, TRP1, LEU2, URA3, ADE2, CAN1, SUC2, LYS2, and CUP1 (Edited and written by Yasuji Oshima, Biochemical Experimental Method 39, Yeast Molecular Genetics Experimental Method, 119-144 (1996)). These are merely examples and such a marker gene may be appropriately selected according to the genotype of a yeast strain to be used as a host for gene introduction. A person skilled in the art can appropriately carry out a series of techniques concerning the construction of the above fusion gene expression plasmid with reference to the Examples described below or conventional methods.

To an expression vector, a promoter, an enhancer, a splicing signal, poly A addition signal, a selection marker, SV40 replication origin, tag-encoding DNA, and the like may be added. Also an expression vector may be a fusion protein expression vector. Examples of a commercial fusion protein expression vector include pGEX series (Amersham Pharmacia Biotech), pET CBD Fusion System 34b-38b (Novagen), pET Dsb Fusion Systems 39b and 40b (Novagen), and pET GST Fusion System 41 and 42 (Novagen).

For transformation of host yeast, a generally employed gene introduction method, such as a calcium phosphate method, electroporation, lipofection, a particle gun method, a polyethylene glycol (PEG) method, an *Agrobacterium* method, or a protoplast fusion method may be employed. A transformant can be selected according to a conventional method. In general, a transformant can be selected using a selection marker or the like incorporated into a vector used herein.

In the mutant yeast according to the present invention, particularly preferably a decrease in growth ability due to functional deficiency in a protein-O-mannosyltransferase gene is suppressed. The mutant yeast according to the present invention has growth ability accounting for 70% or more (the level of a decrease in growth ability: 30% or less), preferably 75% or more (the level of a decrease in growth ability: 25% or less), more preferably 80% or more (the level of a decrease in growth ability: 20% or less), further more preferably 85% or more (the level of a decrease in growth ability: 15% or less), and particularly preferably 88% or more (the level of a decrease in growth ability: 12% or less) of that of a yeast strain having the same genotype other than functional deficiency in the protein-O-mannosyltransferase gene. Such a level of a decrease in growth ability can be evaluated on the basis of the highest cell concentration reached as observed by serial measurement when cells are cultured at 30° C.

In the mutant yeast according to the present invention, a decrease in stress resistance induced by functional deficiency in a protein-O-mannosyltransferase gene is also preferably suppressed. Specifically, for example, in the mutant yeast according to the present invention, a decrease in high-temperature stress resistance (e.g., resistance to culture at 30° C. or higher, more preferably at 35° C. or higher, or at 37° C. or higher) due to functional deficiency in a protein-O-mannosyltransferase gene is also preferably suppressed. In the mutant yeast according to the present invention, furthermore, a decrease in drug stress resistance (e.g., resistance to culture in the presence of antibiotics such as hygromycin or Calcofluor white (CFW) known to have activity of inhibiting yeast growth) due to functional deficiency in the protein-O-mannosyltransferase gene is also preferably suppressed.

The mutant yeast according to the present invention in which such a decrease in growth ability and a decrease in stress resistance are suppressed can be prepared from yeast (sugar-chain-modified yeast strain) modified by causing functional deficiency in or introducing a gene involved in sugar chain biosynthesis as described above. Such a yeast strain can be prepared by further introducing a mutation into the genome. A mutagenesis method therefor is preferably, but is not limited to, a disparity mutagenesis method (Abe H. et al., Glycobiology, vol. 19, no. 4, pp. 428-436 (2009), Patent Document 3, International Patent Publication WO 2009/150848), for example.

The disparity mutagenesis method is a method for introducing a mutation by regulating the correcting function of DNA polymerase. Specifically, the method involves introducing a plasmid containing a mutant enzyme-encoding gene (e.g., mutant polymerase δ) that is deficient in DNA polymerase's function of correcting replication errors (this function is exhibited during chromosomal DNA replication) into host yeast cells, causing the expression of polymerase lacking the correcting function, maintaining a mutation introduced into the yeast genome due to a replication error without subjecting it to correction by the mutant enzyme, and thus efficiently accumulating mutations. A mutant polymerase-encoding gene is preferably expressed from a plasmid without incorporation thereof into a host genome. However, the example is not limited thereto. Examples of the mutant polymerase-encoding gene that can be preferably used herein include, but are not limited to, a gene encoding a mutant pol3 protein (a catalytic subunit of mutant polymerase δ) comprising the amino acid sequence of SEQ ID NO: 25 such as a gene (DNA) having an ORF sequence comprising the nucleotide sequence shown in SEQ ID NO: 24. For the disparity mutagenesis method, a mutant pol3 gene expression vector YCplac33/NML mut II (International Patent Publication WO 2009/150848) can be preferably used for mutating budding yeast, for example.

Particularly preferable specific examples of the thus obtained mutant yeast according to the present invention include budding yeast (*Saccharomyces cerevisiae*) YFY22 strain and YFY24 strain. The YFY22 strain and the YFY24 strain were internationally deposited under the Budapest Treaty on Nov. 30, 2010 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11469 and accession number FERM BP-11470, respectively. In addition, these deposited strains had been transferred from domestic deposition (original deposition) to international deposition under the Budapest Treaty. In these mutant yeast strains, a decrease in growth ability due to functional deficiency in a protein-O-mannosyltransferase gene is significantly suppressed, as described above. Furthermore, a decrease in high-temperature stress resistance and a decrease in drug stress resistance are also suppressed. Therefore, when these mutant yeast strains are used as hosts for recombinant protein production, for example, efficient protein production becomes possible.

In a further embodiment of the present invention, in addition to functional deficiency (gene disruption or some mutagenesis) in a protein-O-mannosyltransferase gene, an α-1,6-mannosyltransferase gene, an α-1,3 mannosyltransferase gene, and a mannose-1-phosphorylation regulating gene and introduction of an α-1,2-mannosidase I gene in yeast, an α-1,2-mannosidase I gene may be re-introduced (re-introduction, that is, the introduction of a $2^{nd}$ copy of or more copies of the gene). The re-introduction is particularly preferable when the production amount of the M5 sugar chain (the N-linked sugar chain of $Man_5GlcNAc_2$) of mutant yeast is decreased and the production amount of the M8 sugar chain (the N-linked sugar chain of $Man_8GlcNAc_2$) of mutant yeast is increased by mutagenesis such as the disparity mutagenesis method. The above mutant yeast to which the α-1,2-mannosidase I gene has been re-introduced has at least two copies of the α-1,2-mannosidase I gene. In the present invention, the ability to produce the M5 sugar chain (the N-linked sugar chain of $Man_5GlcNAc_2$) can be increased by re-introduction of the α-1,2-mannosidase I gene. The ability to produce sugar chains in mutant yeast can be evaluated by measuring or comparing the production amounts of sugar chains under controlled conditions, as described in procedures for sugar chain structural analysis in the following Examples.

The production amount of the M8 sugar chain (the N-linked sugar chain of $Man_8GlcNAc_2$) is not increased by re-introduction of the α-1,2-mannosidase I gene. Therefore, in a preferred embodiment of the mutant yeast according to the present invention, the ratio of the production amount of the M5 sugar chain to the same of the M8 sugar chain is significantly increased by the re-introduction of the α-1,2-mannosidase I gene. In particular, as a result of re-introduction of the α-1,2-mannosidase I gene, mutant yeast is preferably modified so as to have increased ability to produce the M5 sugar chain such that the production amount of the M5 sugar chain is significantly higher than the same of the M8 sugar chain. Such a mutant yeast strain is a strain capable of highly efficiently producing the M5 N-linked sugar chain, such that it can exhibit the production amount of the M5 sugar chain preferably 1.1 times or more, more preferably 1.5 times or more, further preferably 2 times or more, and even more preferably 3 times or more than that of the M8 sugar chain.

Here, the α-1,2-mannosidase I gene to be re-introduced is similar to the above and may have the same nucleotide sequence as that of the initially introduced α-1,2-mannosidase I gene. The re-introduction of the α-1,2-mannosidase I gene can also be carried out by a method similar to that for the above initial introduction of the α-1,2-mannosidase I gene.

In these mutant yeast strains, the binding amount of O-linked sugar chains is preferably significantly decreased compared with the above mutant yeast before re-introduction of the α-1,2-mannosidase I gene. In the mutant yeast, the length of O-linked sugar chains to be added to a protein is preferably shortened.

A preferable specific example of the mutant yeast according to the present invention is a budding yeast (*Saccharomyces cerevisiae*) YKT4 strain. The YKT4 strain was internationally deposited under the Budapest Treaty on Nov. 8, 2011 at the International Patent Organism Depositary (IPOD), National Institute of Technology and Evaluation (KITE), #120, 2-5-8 Kazusakamatari, Kisarazu-shi, Chiba 292-0818, Japan, under accession number FERM BP-11474. In addition, the deposited strain had been transferred from domestic deposition (original deposition) to international deposition under the Budapest Treaty.

In an embodiment of the present invention, the above mutant yeast is further preferably caused to be functionally deficient in a protease gene. Specifically, the above-mentioned mutant yeast, for example, a mutant yeast which has an ability to produce N-linked sugar chains of $Man_5GlcNAc_2$, but has a decreased ability to produce O-linked sugar chains, wherein the yeast is functionally deficient in a protein-O-mannosyltransferase gene, an α-1,6-mannosyltransferase gene, an α-1,3 mannosyltransferase gene and a mannose-1-phosphorylation control gene; and an α-1,2-mannosidase I gene is introduced, may be further preferably subjected to the re-introduction of an α-1,2-mannosidase I gene, and may be further caused to be functionally deficient in a protease gene. Such mutant yeast is also included within the scope of the present invention.

A protease gene that is a functionally deficient gene in the mutant yeast according to the present invention may be any endogenous one, two or more protease genes in host yeast. Examples thereof include a PEP4 gene (in budding yeast, the ORF/CDS sequence ranges from positions 728 to 1945 in the sequence of GenBank Accession No. M13358), a PRB1 gene (in budding yeast, the ORF/CDS sequence ranges from positions 1944 to 3851 in the sequence of GenBank Accession No. M18097), an YPS1 gene (the ORF/CDS sequence ranges from positions 386511 to 388220 (complementary strand) in the sequence of GenBank Accession No. BK006945), and a KEX2 gene (the ORF/CDS sequence ranges from positions 495 to 2939 in the sequence of GenBank Accession No. Z71514). Functional deficiency in both the PEP4 gene and the PRB1 gene is particularly preferable.

The thus obtained mutant yeast according to the present invention that is further caused to be functionally deficient in a protease gene preferably has high ability to produce and secrete proteins. The mutant yeast has the ability to produce and secrete recombinant proteins from the introduced foreign gene, which is increased to a level preferably 1.1 times or more, more preferably 2 times or more, further preferably 4 times or more, and even more preferably 10 times or more than that of a case in which the same foreign gene is introduced into the mutant yeast before it is caused to be functionally deficient in the protease gene. The ability to produce and secrete a recombinant protein of the mutant yeast can be evaluated by measuring the amount of the recombinant protein secreted in a culture supernatant of the mutant yeast. The ability to produce and secrete a recombinant protein in yeast can be evaluated by introducing a galectin 9 gene expression vector into the yeast (preferably, introduced into the genome), and then measuring the amount of galectin 9 in the culture supernatant (e.g., the culture supernatant after 72 hours of culture at 30° C.), for example. This can be carried out according to the method described in Example 10, for example. The thus obtained mutant yeast is advantageous such that it can significantly increase protein production efficiency when a glycoprotein is produced via recombination. These mutant yeast strains are preferably strains having an ability to highly efficiently produce the M5 N-linked sugar chain, which can exhibit the production amount of the M5 sugar chain at a level preferably 1.1 times or more, more preferably 1.5 times or more, further preferably 2 times or more, and even more preferably 3 times or more than that of the M8 sugar chain, in a manner similar to that for the parent strain. Preferable specific examples of such mutant yeast according to the present invention include budding yeast (*Saccharomyces cerevisiae*) YIT3 strain and YIT4 strain. The YIT3 strain and the YIT4 were internationally deposited under the Budapest Treaty on Nov. 8, 2011 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11472 and provisional accession number FERM BP-11473, respectively. In addition, the deposited strains had been transferred from domestic deposition (original deposition) to international deposition under the Budapest Treaty.

Meanwhile, in another embodiment of the present invention, mutant yeast which has an ability to produce N-linked sugar chains of $Man_5GlcNAc_2$ and further has an ability to produce N-linked sugar chains of $GlcNAc_1Man_5GlcNAc_2$ is also provided, wherein the yeast is functionally deficient in an α-1,6-mannosyltransferase gene, an α-1,3 mannosyltransferase gene, and a mannose-1-phosphorylation regulating gene, and an N-acetylglucosaminetransferase I gene and an α-1,2-mannosidase I gene are introduced. The α-1,2-mannosidase I gene is preferably incorporated into a host genome.

The functional deficiency in the α-1,6-mannosyltransferase gene, the α-1,3 mannosyltransferase gene, and the mannose-1-phosphorylation regulating gene, and the introduction of the α-1,2-mannosidase I gene are similar to those in the above modified yeast, wherein the yeast is functionally deficient in the protein-O-mannosyltransferase gene, the α-1,6-mannosyltransferase gene, the α-1,3 mannosyltransferase gene, and the mannose-1-phosphorylation regulating gene, and the α-1,2-mannosidase I gene is introduced.

In this embodiment, the N-acetylglucosaminetransferase I gene (typically, GnT-I gene) to be introduced into host yeast may be derived from any organism, such that the gene may be a plant N-acetylglucosaminetransferase I gene, for example. The sequences of the N-acetylglucosaminetransferase I genes of various organisms are known. The N-acetylglucosaminetransferase I gene to be introduced into host yeast is preferably an N-acetylglucosaminetransferase I gene of a plant of the family Gramineae and is more preferably a rice N-acetylglucosaminetransferase I gene.

The modified yeast can generate a complex sugar chain intermediate ($GlcNAc_1Man_5GlcNAc_2$) seen in mammals by the addition of an N-acetylglucosamine residue to a terminal mannose residue of the N-linked sugar chain of $Man_5GlcNAc_2$ via introduction of the N-acetylglucosaminetransferase I gene. The modified yeast further retains the ability to produce the N-linked sugar chain of $Man_5GlcNAc_2$.

A particularly preferable specific example of such mutant yeast according to the present invention is a budding yeast (*Saccharomyces cerevisiae*) YKT1 strain. The YKT1 strain was internationally deposited under the Budapest Treaty on Nov. 30, 2010 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11471. In addition, the deposited strain had been transferred from domestic deposition (original deposition) to international deposition under the Budapest Treaty.

In another embodiment according to the present invention, mutant yeast which has an ability to produce N-linked sugar chains of $Man_5GlcNAc_2$ (M5 sugar chain) and further has an ability to produce N-linked sugar chains of $Man_8GlcNAc_2$ (M8 sugar chain) is also provided, wherein an α-1,6-mannosyltransferase gene, an α-1,3 mannosyltransferase gene, and a mannose-1-phosphorylation regulating gene is functionally deficient, and 1 copy or 2 or more copies of an α-1,2-mannosidase I gene are introduced, and the ability to produce and secrete proteins is further increased. In the mutant yeast, the ability to produce and secrete a recombinant protein from the introduced foreign gene is increased to a level preferably 1.1 times or more, more preferably 2 times or more, further preferably 4 times or more, and even more preferably 10 times or more than that of a case in which the same foreign gene is introduced into yeast before enhancement of the ability to produce and secrete proteins. The ability to produce and secrete a recombinant protein of mutant yeast can be evaluated in a manner similar to the above by measuring the amount of the recombinant protein secreted in a culture supernatant of the mutant yeast. In the mutant yeast, preferably not only the ability to produce and secrete a recombinant protein but also the ability to produce and secrete an endogenous protein is significantly increased.

The mutant yeast can be prepared from mutant yeast which has an ability to produce N-linked sugar chains of $Man_5GlcNAc_2$ (M5 sugar chain) and further has an ability to produce N-linked sugar chains of $Man_8GlcNAc_2$ (M8 sugar chain), wherein an α-1,6-mannosyltransferase gene, an α-1,3 mannosyltransferase gene, and a mannose-1-phosphorylation regulating gene is functionally deficient, and an α-1,2-mannosidase I gene is introduced. Such a yeast strain can be prepared by further introducing a mutation that increases the ability to produce and secrete proteins into the genome. An example of a mutagenesis method is, but is not limited to, preferably a disparity mutagenesis method (Abe H. et al., Glycobiology, vol. 19, no. 4, pp. 428-436 (2009), Patent Document 3, International Patent Publication WO 2009/150848).

The thus obtained mutant yeast has high ability to produce and secrete proteins. A preferable specific example of the mutant yeast according to the present invention is a budding yeast (*Saccharomyces cerevisiae*) YFY25 strain.

In an embodiment of the present invention, such mutant yeast is further preferably caused to be functionally deficient in a protease gene. Mutant yeast obtained by further causing the above mutant yeast such as the YFY25 strain to be functionally deficient in a protease gene is also included within the scope of the present invention.

A protease gene that is caused to be functionally deficient gene in mutant yeast according to the present invention may be any one, two or more endogenous protease genes of host yeast. Examples of such a protease gene include a PEP4 gene (in budding yeast, the ORF/CDS sequence ranges from positions 728 to 1945 in the sequence of GenBank Accession No. M13358), a PRB1 gene (in budding yeast, the ORF/CDS sequence ranges from positions 1944 to 3851 in the sequence of GenBank Accession No. M18097), a YPS1 gene (the ORF/CDS sequence ranges from positions 386511 to 388220 (complementary strand) in the sequence of GenBank Accession No. BK006945), and a KEX2 gene (the ORF/CDS sequence ranges from positions 495 to 2939 in the sequence of GenBank Accession No. Z71514).

The mutant yeast according to the present invention further caused to be functionally deficient in a protease gene as described above has preferably particularly high ability to produce and secrete proteins. In the mutant yeast according to present invention, not only the ability to produce and secrete the recombinant protein that is expressed from an introduced foreign gene, but also the ability to produce and secrete an endogenous protein is increased. In the mutant yeast, for example, the ability to produce and secrete the recombinant protein from an introduced foreign gene is increased to a level preferably 1.1 times or more, more preferably 2 times or more, further preferably 4 times or more, and even more preferably 10 times or more than that of a case in which the same foreign gene has been introduced into the mutant yeast before caused to be functionally deficient in a protease gene. The ability of secretory production of a recombinant protein of mutant yeast can be evaluated by measuring the amount of the recombinant protein secreted in a culture supernatant of the mutant yeast. The ability of secretory production of a recombinant protein in yeast can be evaluated by, for example, introducing a galectin 9 gene expression vector into the yeast (preferably into the genome) and then measuring the amount of galectin 9 in the culture supernatant (e.g., the culture supernatant after 72 hours of culture at 30° C.). For example, this can be carried out according to the method described in Example 10. The thus obtained mutant yeast is advantageous in that it can significantly increase protein production efficiency when a glycoprotein is produced via recombination. A preferable specific example of such mutant yeast according to the present invention is a budding yeast (*Saccharomyces cerevisiae*) YFY26 strain. The YFY26 strain was internationally deposited under the Budapest Treaty on Dec. 5, 2011 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11475. In addition, the deposited strain had been transferred from domestic deposition (original deposition) to international deposition under the Budapest Treaty. Such mutant yeast according to the present invention is advantageous in that it can increase high protein production efficiency when a glycoprotein is produced via recombination.

The present invention provides, as described above, mutant yeast that is capable of producing the N-linked sugar chain of $Man_5GlcNAc_2$, wherein:

the ability to produce secretory proteins is increased due to functional deficiency in an α-1,6-mannosyltransferase gene, an α-1,3 mannosyltransferase gene, and a mannose-1-phosphorylation regulating gene, and introduction of an α-1,2-mannosidase I gene; or the ability to produce secretory proteins is increased due to functional deficiency in a protease gene, or mutagenesis and functional deficiency in a protease gene. Specific examples of such mutant yeast include the above YIT3 strain, YIT4 strain, and YFY26 strain.

Figure 13:
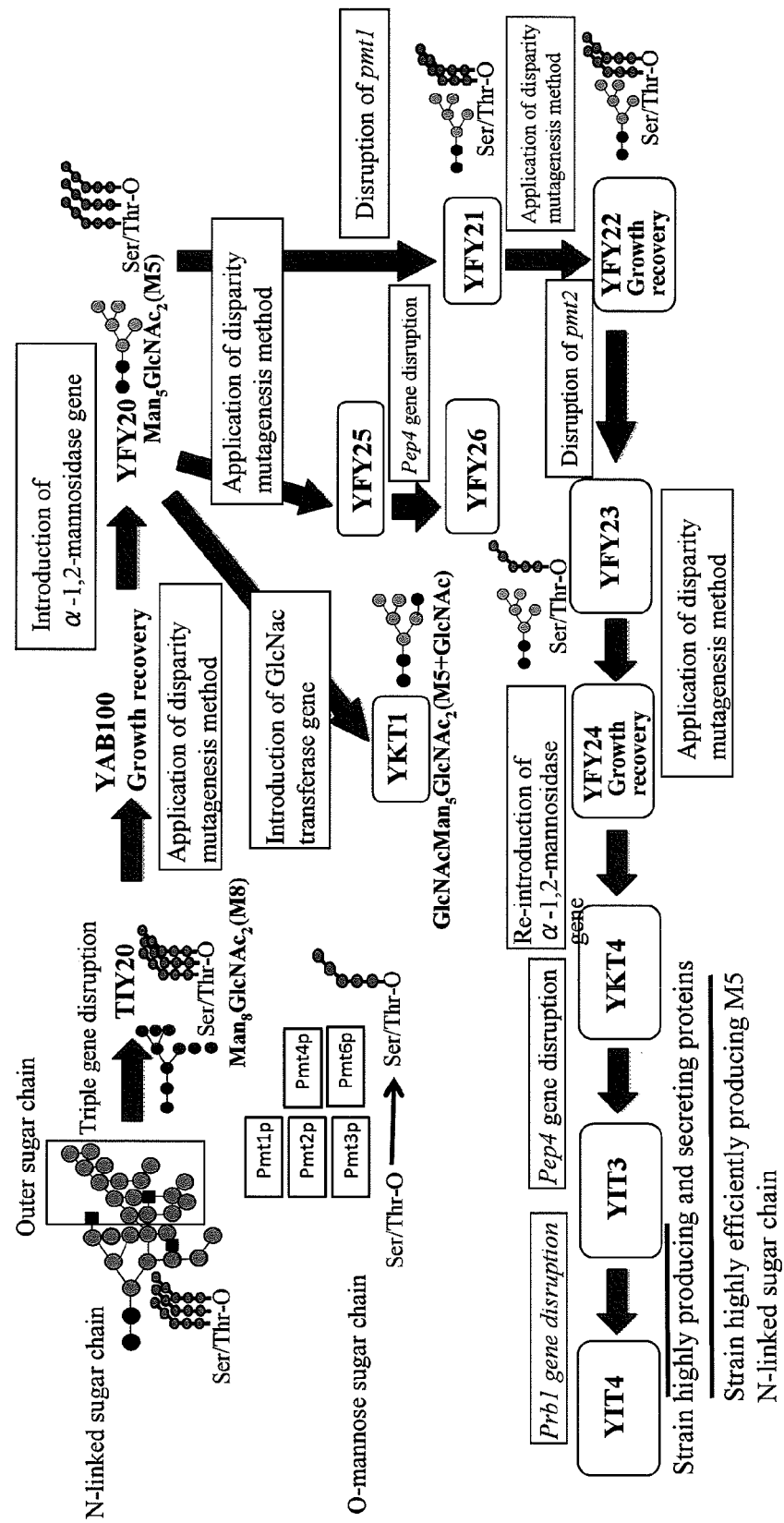
FIG. 13 schematically shows the outline for preparation of sugar-chain modified yeast in the present invention.

The above described preparation of the sugar-chain modified yeast in the present invention is summarized in FIG. 13.

3. Use for Glycoprotein Production

In the present invention, glycoprotein production can be carried out using the above-described sugar-chain modified yeast. According to the method for producing glycoprotein, a protein to which a mammalian-type sugar chain is added can be produced. Therefore, the present invention provides use of the above mutant yeast for producing a glycoprotein with a mammalian-type sugar chain or such a sugar chain, and a method for producing a glycoprotein or a sugar chain using the above mutant yeast.

Examples of a glycoprotein appropriate for production by the method for producing a glycoprotein according to the present invention using mutant yeast that is capable of producing the N-linked sugar chain of $Man_5GlcNAc_2$ and has decreased ability to produce an O-linked sugar chain, wherein the yeast has functional deficiency in a protein-O-mannosyltransferase gene, an α-1,3 mannosyltransferase gene, a mannose-1-phosphorylation regulating gene, and a α-1,6-mannosyltransferase gene, and an α-1,2-mannosidase I gene is introduced, include, but are not limited to, erythropoietin, interferon-γ, interferon-β, lactoferrin, transferrin, α-galactosidase, α-glucosidase, α-L-iduronidase, arylsulfatase, N-acetylgalactosamine-6-sulfatase, β-galactosidase, β-glucosidase, iduronate 2-sulfatase, ceramidase, galacto-cerebrosidase, β-glucuronidase, heparanN-sulfatase, N-acetyl-α-gluco saminidase, acetylCoA-α-gluco saminideN-acetyltransferase, N-acetyl-glucosamine-6sulfatase, galactose 6-sulfatase, arylsulfataseA, B, and C, arylsulfataseAcerebroside, ganglioside, acidic β-galactosidase, $G_{M1}$ ganglioside, acidic β-galactosidase, hexosaminidaseA, hexosaminidaseB, α-fucosidase, α-N-acetylgalacto-saminidase, glycoprotein neuraminidase, aspartyiglucosamine amidase, acidic lipase, acidic ceramidase, and lysosomesphingomyelinase.

Examples of a glycoprotein appropriate for production by the method for producing a glycoprotein according to the present invention using mutant yeast that is capable of producing the N-linked sugar chain of $Man_5GlcNAc_2$ and is further capable of producing the N-linked sugar chain of $GlcNAc_1Man_5GlcNAc_2$, wherein the yeast has functional deficiency in an α-1,6-mannosyltransferase gene, an α-1,3 mannosyltransferase gene, and a mannose-1-phosphorylation regulating gene, and an N-acetylglucosaminetransferase I gene and an α-1,2-mannosidase I gene are introduced include, but are not limited to, erythropoietin, interferon-γ, interferon-β, lactoferrin, transferrin, α-galactosidase, α-glucosidase, α-L-iduronidase, arylsulfatase, N-acetylgalactosamine-6-sulfatase, β-galactosidase, β-glucosidase, iduronate 2-sulfatase, ceramidase, galacto-cerebrosidase, β-glucuronidase, heparanN-sulfatase, N-acetyl-α-gluco saminidase, acetylCoA-α-gluco saminideN-acetyltransferase, N-acetyl-glucosamine-6sulfatase, galactose 6-sulfatase, arylsulfataseA, B, and C, arylsulfataseAcerebroside, ganglioside, acidic β-galactosidase, $G_{M1}$ ganglioside, acidic β-galactosidase, hexosaminidaseA, hexosaminidaseB, α-fucosidase, α-N-acetylgalacto-saminidase, glycoprotein neuraminidase, aspartyiglucosamine amidase, acidic lipase, acidic ceramidase, and lysosomesphingomyelinase.

Examples of a glycoprotein appropriate for production by the method for producing a glycoprotein according to the present invention using other strains of sugar-chain modified yeast according to the present invention are similar to those listed above.

According to the method, a target sugar chain is added to a recombinant protein produced in the above sugar-chain-modified yeast transformed with a target glycoprotein gene. Therefore, transformed yeast is prepared by introducing DNA encoding the amino acid sequence of a target glycoprotein into the above sugar-chain modified yeast according to the present invention. The recombinant protein is expressed from the DNA, so that the target glycoprotein can be produced. Typically, DNA encoding the amino acid sequence of a target glycoprotein is incorporated under control of a promoter in a nucleic acid construct such as an expression vector that can be replicated within yeast or an expression cassette that can be incorporated into a yeast genome, and then the resultant is introduced into the above sugar-chain-modified yeast. A promoter to be used herein may be a constitutive or an inducible promoter, as long as it can function in yeast. Furthermore, a promoter to be used herein may be a transient or tissue- or cell-specific promoter. Examples of such a promoter include, but are not limited to, a glyceraldehyde3phosphatedehydrogenase (GAPDH) promoter, an ADH1 promoter, a TEF1 promoter, a GAL-L1 promoter, a copper inducible promoter (CUP1 promoter). A transformed yeast strain can be selected based on a selection marker or the expression of a reporter gene contained in the nucleic acid construct, for example. In a preferred example, glycoprotein production using the above sugar-chain modified yeast can be carried out by introducing an expression vector (constructed by incorporating DNA encoding the amino acid sequence of a target glycoprotein under control of preferably a promoter) into the sugar-chain modified yeast as host cells for transformation, culturing the thus obtained transformed yeast, and then inducing the expression of the recombinant protein. The expression of a recombinant protein can be induced according to genetic engineering techniques known by persons skilled in the art. For example, when an inducible promoter is used, the expression of a recombinant protein can be induced by adding an inducer capable of inducing promoter activity to the medium and culturing the cells. When a constitutive promoter is used, the expression of a recombinant protein can be induced by culturing the yeast without adding any inducer, for example.

Transformed yeast can be cultured according to a method generally employed for culturing yeast. A medium that may be used herein comprises carbon sources, nitrogen sources, inorganic salts, and the like assimilable by yeast and such a medium enables efficient culture of the transformant. Specific examples of a medium that can be appropriately used herein include YPD medium, YPG medium, YPDG medium, YPAD medium, glucose synthesis minimum medium (SD), minimum medium supplemented with iodine (SMM), Hartwell's complete medium (HC), GAL fermentation test medium, and sporulation medium. A medium may be supplemented with KCl, sorbitol, or the like. A medium is preferably adjusted to pH6 to 8 and then used. Culture can be carried out according to a conventional method while appropriately performing aeration or agitation at 28° C. to 37° C., preferably at 29° C. to 35° C., and more preferably at 30° C. for an appropriate period (e.g., overnight to 1 month, preferably 1 day (24 hours) to 14 days, and more preferably 2 days (48 hours) to 7 days).

The thus obtained glycoprotein lacks a mammalian sugar chain such as an outer sugar chain, but has the N-linked sugar chain of $Man_5GlcNAc_2$. When mutant yeast that is caused to be functionally deficient in a protein-O-mannosyltransferase gene is used, a glycoprotein with a significantly decreased binding amount of an O-linked sugar chain can be produced according to the method of the present invention. When mutant yeast, into which an N-acetylglucosaminetransferase I gene has been introduced, is used, a glycoprotein with the N-linked sugar chain of $GlcNAc_1Man_5GlcNAc_2$ binding thereto can also be produced.

Alternatively, host yeast's natural glycoprotein with a mammalian sugar chain added thereto can also be produced. In this case, the above sugar-chain modified yeast is cultured under conditions for inducing the expression of a target glycoprotein, so that a yeast protein with a mammalian sugar chain added thereto can be produced.

Furthermore, in an embodiment of the production of a glycoprotein using the sugar-chain modified yeast according to the present invention, the use of mutant yeast that is capable of producing the N-linked sugar chain of $Man_5GlcNAc_2$, wherein the yeast is functionally deficient in an α-1,6-mannosyltransferase gene, an α-1,3 mannosyltransferase gene, and a mannose-1-phosphorylation regulating gene, an α-1,2-mannosidase I gene is introduced, and the yeast is further functionally deficient in a protease gene so as to have increased ability to produce and secrete proteins is advantageous, since a glycoprotein (preferably a foreign gene-derived recombinant glycoprotein) can be secreted in the culture supernatant with high efficiency and high yield.

The thus produced glycoprotein having a mammalian sugar chain or a sugar chain added to the protein can be obtained by a general method for extracting a glycoprotein from mutant yeast cells or the culture supernatant thereof or by isolation and purification techniques. For example, after completion of culture, cells are collected by centrifugation and then suspended in aqueous buffer. Subsequently, cells are disrupted appropriately using an autoclave, an ultrasonic disintegrator, a French press, a homogenizer, a dyno mill, or the like. The thus obtained cell extract is centrifuged to obtain a supernatant. The glycoprotein can then be collected from the supernatant by appropriately combining solvent extraction, a salting-out method using ammonium sulfate or the like, precipitation using an organic solvent, anion exchange chromatography using a resin such as diethylaminoethyl-sepharose, and affinity chromatography. In the case of a protein produced and secreted in a culture supernatant, the protein can be purified from the culture supernatant by appropriately combining a salting-out method using ammonium sulfate or the like, precipitation using an organic solvent, anion exchange chromatography using a resin such as diethylaminoethyl-sepharose, and affinity chromatography. A method that can be used for isolation of a sugar chain from a glycoprotein comprises treating the thus collected glycoprotein with hydrazine, glycopeptidase (e.g., glycopeptidaseF), or the like, performing extraction using an organic solvent, and then collecting an aqueous layer.

EXAMPLES

The present invention is further illustrated with reference to the following examples. However, these examples do not limit the technical scope of the present invention.

Reference Example 1

Preparation of Sugar-Chain Modified Yeast Strain Having Recovered its Growth Ability According to the method for preparing a sugar-chain modified yeast strain that has recovered its growth ability as described in JP Patent Publication (Kokai) No. 2008-220172 A, a sugar-chain modified yeast strain YAB100 having an ability to produce $Man_8GluNAc_2$ sugar chains, efficiently producing a human-type glycoprotein, and being excellent in growth ability and protein-producing capability was prepared.

Briefly, a budding yeast sugar-chain modified strain, TIY20 strain (matα, och1::hisG, mnn1::hisG, mnn4::hisG), producing a modified sugar chain having the same structure as that of the sugar-chain modified yeast strain TIY19, was obtained by tetrad analysis from the same clone as that of the TIY19 having OCH1 gene disruption (Δoch1), MNN1 gene disruption (Δmnn1), and MNN4 gene disruption (Δmnn4). TIY19 was disclosed in International Patent Publication WO01/014522. A pol3 gene mutant (SEQ ID NO: 1) was introduced into the budding yeast sugar-chain modified strain TIY20 to obtain a transformant. The transformant was cultured in an SD-U synthetic medium for budding yeast (6.7 g of Yeast nitrogen base without amino acids (Difco laboratories), 20 g of glucose, 0.77 g of CMS-URA (Sunrise Science Products) (liquid)) and then seeded onto SD-U solid medium and cultured at 37° C. for 3 days for obtaining a high temperature-resistant strain. The thus generated colonies were collected, streaked over YPAD complete medium (10 g of yeast extract (Difco laboratories), 20 g of peptone (Difco), 0.2 g of adenine sulfate (Sigma), 20 g of glucose/1 L) and then cultured. Single colonies were collected and then colonies that had been unable to grow on SD-U medium were obtained. A yeast strain of the thus obtained colonies was confirmed to generate an N-linked sugar chain having the same sugar chain length as that in the case of TIY20 as the parent strain. Efficiency of the growth recovery of the yeast strain was examined in YPAD. It was confirmed that the yeast strain recovered its growth ability that had been decreased in the TIY20 strain compared with a wild-type strain. It was also confirmed by sugar chain structural analysis that the thus obtained yeast strain produced $Man_8GluNAc_2$ sugar chains corresponding to so-called a mammalian-type sugar chain. It was further demonstrated by chitinase analysis that the efficiency of protein secretion from the thus obtained yeast strain had been recovered from the decreased efficiency of protein secretion in the TIY20 strain compared with a wild-type strain to a level equivalent to that of a wild-type. The thus obtained sugar-chain modified yeast strain, YAB100 strain, producing the mammalian-type sugar chain $Man_8GluNAc_2$, which had recovered its growth ability and protein secretion efficiency, was used for the following Examples. The YAB100 strain was internationally deposited under the Budapest Treaty on Jul. 11, 2006 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11122.

Example 1

Generation of YFY20 Strain (1) Construction of Genome Integration Vector pRS304-OCH1-msdS with α-1,2-Mannosidase I Gene (msdS) from *A. saitoi*

A DNA fragment encoding the transmembrane region (61 amino acids from initiation methionine Met; SEQ ID NO: 2) of the budding yeast OCH1 gene (OCH1 gene sequence: GenBank Accession No. NM_001180903; full-length Och1 amino acid sequence: NCBI database Accession No. NP_011477) was obtained by a PCR method using genomic DNA extracted from budding yeast (*Saccharomyces cerevisiae*) as a template. Primers used for PCR were designed based on a known OCH1 gene sequence and then synthesized by a conventional method.

Furthermore, a DNA fragment encoding an N-terminal-truncated msdS protein (SEQ ID NO: 3) prepared by removing 37 amino acids from the N-terminus, which was from *Aspergillus saitoi* (*A. saitoi*) α-1,2-mannosidase I gene (msdS) (msdS gene sequence: GenBank Accession No. D49827; full-length msdS amino acid sequence: NCBI database Accession No. BAA08634) was obtained by a PCR method using genomic DNA extracted from *A. saitoi* as a template. Primers used for PCR were designed based on a known msdS gene sequence and then synthesized by a conventional method.

The thus obtained both DNA fragments were linked to construct a fusion gene. The fusion gene was cloned into the EcoR I-Sal I site of a budding yeast expression vector YEp352GAP-II (Nakayama K. et al., Glycobiology, vol. 13, pp. 673-680 (2003)) to construct pAB103. The OCH1-msdS DNA fragment containing a GAPDH promoter and a terminator (Kainuma et al., Glycobiology, vol. 9, pp. 133-141 (1999)) from the vector as well as the fusion gene (insert) was amplified by PCR using the pAB103 as a template. For PCR, a forward primer GAPF-Not1 5'-CCCCCGCGGCCGCG-GAACAACAAGAAGTTTAATGACGCGAGGCC-3' (SEQ ID NO: 4) and a reverse primer GAPR-Kpn1 5'-GGGGGGGTACCGAATCGAAAATGTCAT-TAAAATAGTATATAAATTG-3' (SEQ ID NO: 5) were used. A PCR solution was prepared with the following composition.

Composition of PCR Solution

| | |
|---|---|
| 10 x reaction buffer | 5.0 μl |
| Template DNA | 20 ng |
| 100 μM forward primer | 0.2 μl |

-continued

| | |
|---|---|
| 100 μM reverse primer | 0.2 μl |
| DNA polymerase Expand High Fidelity (Roche) | 1 μl |
| Sterilized milliQ water (added to a total volume of 50 μl) | |
| Total | 50 μl |

PCR conditions were 1 cycle (94° C. for 2 minutes) of template denaturation, followed by 30 cycles for PCR synthesis (94° C. for 15 seconds, 55° C. for 30 seconds, and 72° C. for 2 minutes and 30 seconds (the time for reaction at 72° C. in each cycle was prolonged by 5 seconds in the 11 cycle and the following cycles)), and 1 cycle (72° C. for 7 minutes).

The thus obtained amplification fragment was cloned into a TA cloning site of a TA cloning vector pCR2.1TOPO (Invitrogen). The vector was digested with restriction enzymes, Not I and Kpn I. The thus obtained DNA fragment GAPDH-OCH1-msdS was cloned into the Not I-Kpn I site of a genome integration vector pRS304. The thus obtained recombinant vector was designated as pRS304-OCH1-msdS.

(2) Preparation of YFY20 Strain (OCH1-msdS-Expressing Strain)

pRS304-OCH1-msdS was cleaved with a restriction enzyme EcoR V for linearization. The linear vector was introduced into the above sugar-chain modified yeast strain YAB100 prepared in Reference example 1 for transformation.

Yeast cells were transformed as follows. First, the sugar-chain modified yeast strain YAB100 was cultured with shake for 15 hours in 5 ml of liquid medium YPAD+KCl (10 g of yeast extract (Difco), 20 g of peptone (Difco), 20 g of glucose, 0.2 g of adenine sulfate (Wako Pure Chemical Industries, Ltd.), 22.37 g of KCl/1 L). All yeast cells were collected after culture and then washed with 1 ml of sterilized milliQ water. The thus obtained cell pellet was suspended in 1 ml of DTT buffer (10 mM dithiothreitol, 0.6 M sorbitol, 10 mM Tris-Cl, pH 7.5), left to stand at room temperature for 30 minutes, and then washed 3 times with 1 ml of ice-cold 1 M sorbitol. The cell pellet was suspended in 100 μl of 1 M sorbitol and then 3 μg of the above linear vector was added. The resultant was gently stirred and then left to stand on ice for 5 minutes. The suspension was transferred to an electroporation cuvette (2-mm gap), electrified (1.5 kV, 1 pulse) using an electroporator (BIO-RAD MicroPulser), collected, plated on an SD-W plate (6.7 g of Yeast nitrogen base w/o amino acid (Difco), 20 g of glucose, 0.2 g of adenine sulfate (Wako Pure Chemical Industries, Ltd.), 0.74 g of --Trp DO Supplement (Clontech), 22.37 g of KCl, 20 g of agar/1 L), and then cultured at 30° C. Thus, tryptophan-positive colonies were obtained. Strains in which the OCH1-msdS DNA fragment had been incorporated into the genome were selected and obtained with a colony PCR method from the thus obtained plurality of transformants. For colony PCR, a forward primer Man1-3F 5'-CGAAGAACCTCGCCG-3' (SEQ ID NO: 6) and a reverse primer Man1-Sal1 5'-GGGCCCGTCGACTTATGTAC-TACTCACCCGCACTGGATGTGCCTCGG-3' (SEQ ID NO: 7) for specific amplification of the msdS gene were used. The PCR solution was prepared with the following composition.

Composition of PCR Solution

| | |
|---|---|
| 10 x reaction buffer | 1.0 μl |
| 0.1% BSA | 1.7 μl |
| Yeast cells | (adequate amount) |
| 100 μM forward primer | 0.1 μl |

| | |
|---|---|
| 100 μM reverse primer | 0.1 μl |
| DNA polymerase Ex Taq | 0.25 μl |
| Sterilized milliQ water (added to a total volume of 10 μl) | |
| Total | 10 μl |

Reaction conditions were 1 cycle (94° C. for 5 minutes) of cell disruption, followed by 40 cycles for PCR synthesis (92° C. for 30 seconds, 49° C. for 30 seconds, and 72° C. for 1 minute), and 1 cycle (72° C. for 7 minutes). The thus obtained amplification product (4 μl) was applied to 1.0% agarose gel, subjected to electrophoresis at 100 V for 20 minutes (electrophoresis buffer: 24.2 g of Tris base, 5.71 ml of acetic acid, EDTA.2Na (2H$_2$O) 1.86 g/500 ml), and thus strains (expressing msdS) for which bands specific to the msdS gene had been detected were selected. Furthermore, the expression of the OCH1-msdS fusion gene in the selected strains was confirmed by an RT-PCR method. The thus obtained OCH1-msdS-expressing strain and the YAB100 strain obtained in Reference example 1 were each cultured with shake in 10 ml of YPAD liquid medium at 30° C. for 15 hours. These cells were separately collected and then washed with sterile water. Sepasol (200 μl, NACALAI TESQUE, INC.) and glass beads were added and then cells were disrupted by vigorous vortexing. A cell disruption solution was transferred to a new tube and then 800 μl of Sepasol was added. The solution was stirred and then left to stand at room temperature for 5 minutes. Chloroform (200 μl) was added and then the tube was turned upside down for mixing. After left to stand at room temperature for 3 minutes, the solution was centrifuged at 4° C. and 12000 g for 15 minutes. An aqueous phase was transferred to another tube, 500 μl of isopropanol was added, the mixture was mixed and left to stand at room temperature for 10 minutes. Centrifugation was carried out at 4° C. and 12000 g for 5 minutes, so as to remove the supernatant. 75% ethanol was added to the thus obtained pellet. After washing, ethanol was discarded, the resultant was sufficiently dried, and then the resultant was dissolved in 200 μl of DEPEC-treated water. Furthermore, phenol, chloroform, and isoamyl alcohol (=50:48:2) were added in the same amount as that of the solution. After mixing, the mixture was centrifuged at 12000 g and room temperature for 5 minutes. An aqueous phase was transferred to a new tube, 100% ethanol was added in an amount 2.5 times the aqueous phase and 3 M LiCl was added in an amount 1/10 the aqueous phase. The solution was left to stand at −80° C. for 30 minutes and then centrifuged at 4° C. and 12000 g for 15 minutes. The supernatant was discarded. The pellet was washed with 70% ethanol, dried well, and then dissolved in 100 μl of sterilized milliQ water, thereby preparing an RNA sample. To prevent the contamination with genomic DNA, 5 μl of DNase I reaction buffer (Invitrogen, deoxyribonuclease I, Amplification Grade) and 2 μl of DNase I (Amp grade; Invitrogen), and 13 μl of milliQ water were added to 30 of the above-obtained RNA sample. The resultant was left to stand at 23° C. for 15 minutes, so as to denature DNA. To the denatured DNA, 4 μl of 25 mM EDTA was added. After 10 minutes of heating at 65° C., phenol, chloroform, and isoamyl alcohol (=50:48:2) were added in the same amount as that of the resultant. After mixing, centrifugation was carried out at 12000 g at room temperature for 5 minutes. An aqueous phase was transferred to a new tube. 100% ethanol was added in an amount 2.5 times the aqueous phase and 3M LiCl was added in an amount 1/10 the aqueous phase were added to the tube. The resultant was left to stand at −80° C. for 30 minutes, and then centrifuged at 4° C. and 12000 g for 15 minutes. The supernatant was discarded. The pellet was washed with 70% ethanol, dried well, and then dissolved in 30 μl of sterilized milliQ water.

RT-PCR (reverse transcription PCR) was carried out using the thus obtained total RNA as a template. A forward primer Man1-3F 5'-CGAAGAACCTCGCCG-3' (SEQ ID NO: 8) and a reverse primer Man1-RX 5'-GTCAAGTGTTGC-GAGCTC-3' (SEQ ID NO: 9) were used for RT-PCR. The reaction solution for RT-PCR was prepared with the following composition.

Composition of RT-PCR Solution

| | |
|---|---|
| 2 x reaction buffer | 6.25 μl |
| Template RNA | 1 μg |
| 10 μM forward primer | 0.25 μl |
| 10 μM reverse primer | 0.25 μl |
| Reverse transcriptase RT/Platinum Taq Mix | 0.25 μl |
| Sterilized milliQ water (added to a total volume of 12.5 μl) | |
| Total | 12.5 μl |

PCR conditions were 1 cycle (50° C. for 30 minutes and 94° C. for 2 minutes) of cDNA synthesis, followed by 25 cycles for PCR synthesis (94° C. for 15 seconds, 55° C. for 30 seconds, and 72° C. for 1 minute), and 1 cycle (72° C. for 10 minutes). The thus obtained amplification product (6 μl) was applied to 2.0% agarose gel and then subjected to electrophoresis in the same manner as described above. Thus, it was confirmed that msdS-specific bands were detected. The thus obtained OCH1-msdS-expression strain was designated as an YFY20 strain.

(3) Sugar Chain Structural Analysis of YFY20 Strain a. Extraction of Mannoprotein The prepared YFY20 strain and the sugar-chain modified yeast strain, YAB100 strain (see JP Patent Publication (Kokai) No. 2008-220172 A and corresponding U.S. Patent Application Publication No. US 2008/0038778 A1), were each cultured in 25 ml of YPAD medium (containing 300 mM KCl) at 30° C. and 180 rpm for 72 hours. At 24, 36, 48, and 60 hours after the initiation of culture, glucose with a final concentration of 2% was added. After completion of culture, centrifugation was carried out at 1200 g for 2 minutes, and thus cells were collected. Cells were washed with PBS and then suspended again in 10 ml of 100 mM citrate buffer (pH 7). Subsequently, for mannoprotein extraction, the resultant was heated with an autoclave at 121° C. for 2 hours. After completion of heating, the resultant was centrifuged at 10000 g for 10 minutes, 9 ml of the supernatant was collected, 27 ml of 100% ethanol was added, and then the resultant was left to stand at −30° C. for 1 hour. Subsequently, centrifugation was carried out at 10000 g for 10 minutes, so as to collect the precipitate. The precipitate was washed with 80% ethanol and then with 100% ethanol, ethanol was removed by volatilization, and thus the protein was collected.

b. Excision and Crude Purification of N-Linked Sugar Chain Via Treatment with Glycopeptidase F The collected protein was suspended in 0.3 ml of solubilizing buffer (500 mM Tris-HCl, 0.5% SDS, 0.75% 2-mercaptoethanol, pH 8.6), followed by 3 minutes of treatment at 100° C. Subsequently, centrifugation was carried out at 20000 g for 10 minutes, so that the supernatant was collected. 20 μl of the supernatant was sampled and then transferred to a new tube. Furthermore, 20 p. 1 of 5% Nonidet P-40, 56 μl of DDW (double distilled water) and 4 μl of 0.5 mU/μl glycopeptidase F (Takara Bio Inc.) were added to the tube, followed by 20 hours of reaction at 37° C. After completion of the reaction, phenol, chloroform, and isoamyl alcohol (25/24/1) were added. The resultant was stirred well and then centrifuged, so that an aqueous layer was collected. Chloroform and isoamyl alcohol (24/1) were added to the aqueous layer, the mixture was stirred well, centrifugation was carried out, and thus an aqueous layer was collected again. Finally, the aqueous layer was completely dried using a centrifugal thickener. The thus obtained crudely purified dry sample contained sugar chains.

c. Pyridylamination and HPLC Analysis of Sugar Chain

The pyridylamination (PAmination) and purification of the sugar chain obtained in "b" above were carried out using a Pyridylamination Manual Kit (Takara Bio Inc.) according to the instructions included with the kit. This is briefly explained as follows. A coupling reagent was added to the dry sugar chain sample to perform 1.5 hours of reaction at 80° C. A reducing reagent was further added to the reaction solution to perform 1 hour of reaction at 80° C. Thus, 2-aminopyridine was bound to the reduced terminal residue of the sugar chain by reductive amination reaction, and then derivatization (pyridylamination) of the sugar chain to a stable fluorescent derivative was carried out. Subsequently, the sample solution was injected into a cellulose cartridge cylinder, the solution was washed with solvent 1 (butanol:ethanol:water:acetic acid=4:1:0.97:0.03 (volume ratio)). Solvent 2 (ethanol:75 mM ammonium bicarbonate=1:2 (volume ratio)) was injected so as to elute the sugar chain, and thus column chromatography purification was carried out. The thus purified and dried pyridylaminated sugar chain was dissolved in 100 µl of DDW, insoluble matter was removed using ultrafree-MC (Millipore), and then HPLC analysis was conducted. HPLC analysis is as described in detail below.

Figure 2:
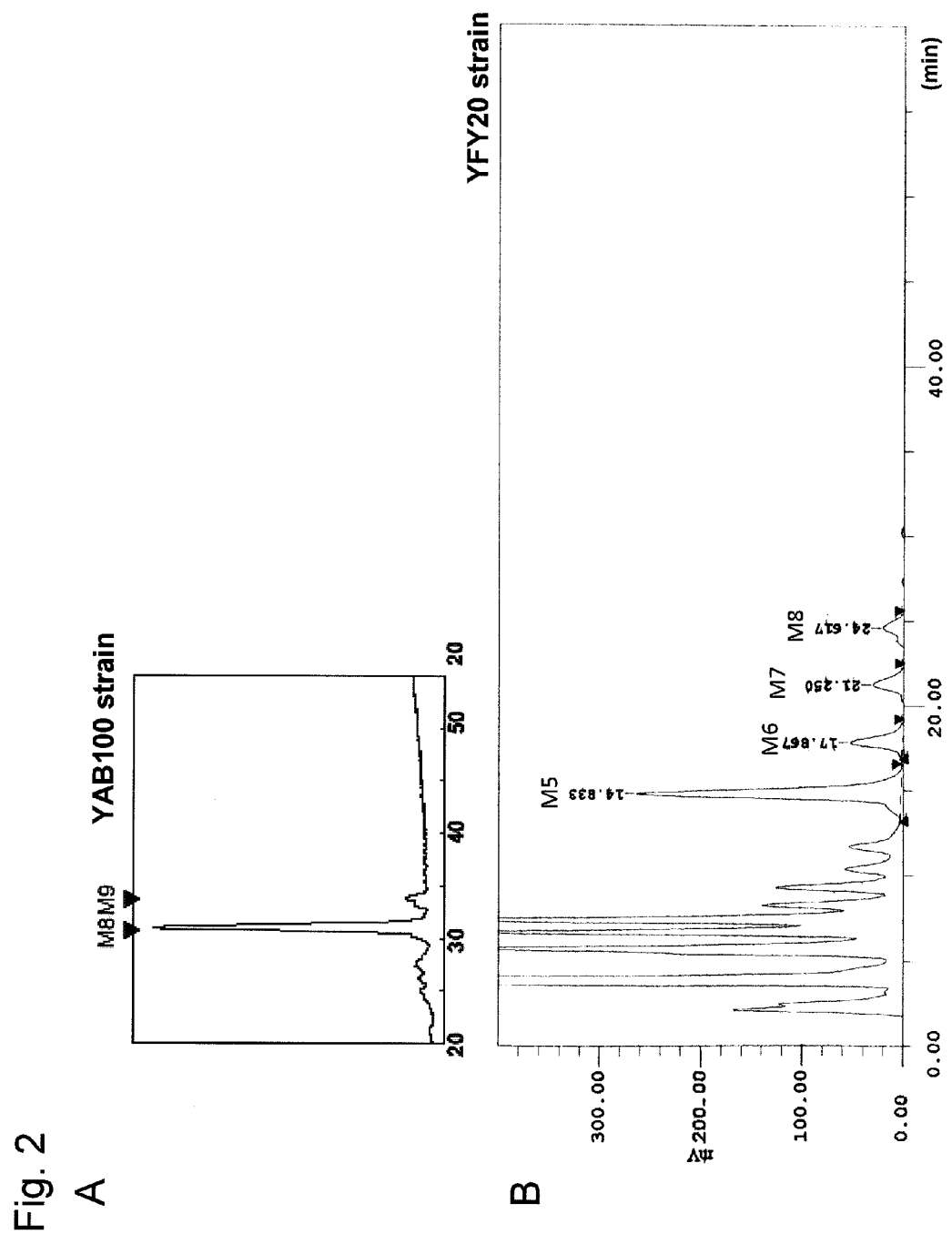
FIG. 2 shows the results of the sugar chain structural analysis by HPLC of mannan sugar chains produced by YAB100 and YFY20 strains.

HPLC: ultra high speed liquid chromatograph prominence UFLC (Shimadzu Corporation)
Column: TSK gel Amide-80 3 µm (4.6 mm I.D.×15 cm) (TOSOH Corporation)
Solvent: acetonitrile/200 mM triethylamine acetate (7/3) (solvent A) acetonitrile/200 mM triethylamine acetate (3/7) (solvent B)
Time for analysis: 60 minutes
Gradient: linear gradient from "solvent A 100%•solvent B 0%" to "solvent A 50%•solvent B 50%" within 50 minutes from the initiation of separation. After 50 minutes, "solvent A 50%•solvent B 50%" was maintained.
Flow rate: 1 ml/min.
Excitation wavelength: 310 nm
Fluorescence wavelength: 380 nm As a result of the HPLC analysis, as shown in FIG. 2, in the YFY20 strain, the sugar chain containing 8 mannose residues (M8) seen in the YAB100 strain disappeared (FIG. 1C, FIG. 2A) and substituted with the sugar chain containing 5 mannose residues (M5) (FIG. 1D, and FIG. 2B). It was thus demonstrated that in the sugar chains produced by the YFY20 strain, a sugar chain portion consisting of 8 mannose residues was converted into the M5 sugar chain consisting of 5 mannose residues by trimming with the introduced α-1,2-mannosidase.

Example 2

Generation of YFY22 Strain and YFY24 Strain (1) Construction of Plasmid for Disruption of PMT1 Gene and PMT2 Gene To inhibit O-linked sugar chain production in a sugar-chain modified yeast strain, a yeast strain in which protein-O-mannosyltransferase genes PMT1 and PMT2 were further disrupted was prepared using the YFY20 strain obtained in Example 1. For disruption of the PMT1 and PMT2 genes, a system (Alani E. et al, Genetics, 116: 541-545 (1987); International Patent Publication WO01/14522) capable of repeatedly using an URA3 auxotrophic marker, through the use of a hisG gene encoding *S. typhimurium* (*Salmonella Typhimurium*)-derived ATP phosphoribosyltransferase, was used. This system involves disrupting a target gene in a genome by homologous recombination and specifically, by substitution with a fragment containing an URA3 gene (resulting in non-auxotrophy for uracil) flanked by hisG genes, using an uracil auxotrophic marker for selection of the disrupted strain, inducing, after selection, homologous recombination between hisG on both ends through the addition of 5-fluoro-orotic acid (5-FOA) that exhibits toxicity because of uracil, so as to delete URA3, and enabling the repeated use of an URA3 marker.

A plasmid for disruption of the PMT1 gene was constructed as follows. A pSP73HUH plasmid was constructed by inserting a hisG-URA3-hisG (HUH) fragment (Alani E., et al., Genetics 116: 541-545, 1987) into a BamH I site of a plasmid pSP73 (purchased from Promega). A PMT1 (ORF1 to 2454)+2454 to 2756 fragment was inserted into a Sph1-Pvu II site of the pSP73HUH plasmid and a −2 to −290 fragment into a Pvu II-Xho I site of the same to construct pSP73-pmt1::HUH. pSP73-pmt2::HUH was constructed as a plasmid for disruption of the PMT2 gene by inserting a hisG-URA3-hisG (HUH) fragment into the BamH I site of pSP73, a PMT1 (ORF1 to 2280)+2260 to 2583 fragment into the Sph 1-Pvu II site, and a +3 to −319 fragment into the Pvu II-Xho I site. The regional locations indicated for the above insert fragments are based on, the PMT1 gene sequence (PMT1ORF; positions 287059 to 289512 in NC_001136 sequence) on the full-length sequence of chromosome IV of a budding yeast S288c strain (GenBank Accession No. NC_001136), and the PMT2 gene sequence (PMT2 ORF; positions 106273 to 108552 in NC_001133 sequence) on the full-length sequence of chromosome I of the same (GenBank Accession No. NC_001133). Each of the thus obtained plasmids for gene disruption was linearized by cleavage with a restriction enzyme Pvu II.

(2) Generation of YFY21 Strain

The linear plasmids obtained in (1) were introduced into the YFY20 strain prepared in Example 1 for transformation. From among the thus obtained transformants, a pmt1::HUH strain (the PMT1 gene in the genome was substituted by homologous recombination with the 5' end-containing fragment of PMT1+HUH+the 3' end-containing fragment of PMT1) was selected and obtained with a colony PCR method. For colony PCR, a forward primer URA-CF: 5'-GGTA-GAGGGTGAACGTTAC3-' (SEQ ID NO: 10) and a reverse primer PMT1-R3: 5'-TGATCTTACACACCTGC-3' (SEQ ID NO: 11) were used. The composition for the reaction solution was the same as that used for colony PCR upon the above selection of the YFY20 strain. PCR conditions were 1 cycle (94° C. for 5 minutes) of cell disruption, followed by 40 cycles for PCR synthesis (92° C. for 30 seconds, 50° C. for 30 seconds, and 72° C. for 2 minutes), and 1 cycle (72° C. for 7 minutes). Four (4) µl of the thus obtained amplification product was subjected to electrophoresis using 1.0% agarose gel as described above, and then bands were detected. Strains, for which bands specific to the pmt1::HUH strain had been detected, were selected.

To remove the introduced marker gene URA3 from the genome of the pmt1::HUH strain, the strain was plated onto a fluoroorotic acid (hereinafter, 5-FOA) medium (6.7 g of Yeast nitrogen base w/o amino acid (Difco), 20 g of glucose, 0.2 g of adenine sulfate (Wako Pure Chemical Industries, Ltd.), 50 mg of uracil (NACALAI TESQUE, INC.), 0.77 g of -Ura DO Supplement (Clontech), 1 g of 5-FOA (Wako Pure Chemical Industries, Ltd.)/1 L). 5-FOA is converted into a toxic substance by a protein encoded by URA3, so that only an URA3-deficient strain or only an URA3 mutant strain can survive even if it incorporates 5-FOA. Hence, a plurality of strains forming colonies on 5-FOA medium were collected as strains from which URA3 had been deleted. The thus collected strains were confirmed by a PCR method for deletion of URA3. PCR was carried out using genomic DNA extracted from a target yeast strain as a template, a forward primer PMT1-F: 5'-GACACGTGTCGAAGAAGAG-3' (SEQ ID NO: 12; binding to the 5' end sequence of PMT1) and a reverse primer PMT1-R3: 5'-TGATCTTACACACCTGC-3' (SEQ ID NO: 13; binding to the 3' end sequence of PMT1) (genome PCR). The solution for genome PCR was prepared with the following composition.

Composition of Genome PCR Solution

| | |
|---|---|
| 10 x reaction buffer: | 1 µl |
| Template genomic DNA: | 1 µg |
| 50 µM forward primer: | 0.2 µl |
| 50 µM reverse primer: | 0.2 µl |
| DNA polymerase Ex Taq: | 0.04 µl |
| Sterilized milliQ water: (added to a total volume of 10 µl) | |
| | Total 10 µl |

Reaction conditions were 1 cycle (94° C. for 2 minutes) of template denaturation, followed by 30 cycles for PCR synthesis (94° C. for 15 seconds, 50° C. for 30 seconds, and 72° C. for 3 minutes), and 1 cycle (72° C. for 7 minutes). Deletion of the URA3 gene from the genome was confirmed on the basis of detected band lengths. The thus obtained strain (from among the pmt1::HUH strains in which PMT1 had been disrupted), for which deletion of the URA3 gene had been confirmed, was designated as an YFY21 strain.

(3) Generation of YFY22 Strain

To obtain strains that had recovered their growth ability and the like through application of a disparity mutagenesis method to the above obtained YFY21 strain, a budding yeast mutation vector YCplac33/NML mut II (International Patent Publication WO 2009/150848) containing a mutant pol3 gene having the ORF (open reading frame) sequence of SEQ ID NO: 25 and causing recombinant expression thereof was introduced by a method similar to the above for transformation, and then the transformant was cultured by the following method. The thus obtained transformant was cultured in SD-U+KCl liquid medium (6.7 g of Yeast nitrogen base w/o amino acid (Difco), 20 g of glucose, 0.2 g of adenine sulfate (Wako Pure Chemical Industries, Ltd.), 0.77 g of -Ura DO Supplement (Clontech), 22.37 g of KCl/1 L). Subculture thereof was repeated 10 times to accumulate mutations. After subculture, cells were spread over SD-U+KCl solid medium and then cultured at 30° C. for 3 days. The strain that had formed the largest colony was picked up. To eliminate YCplac33/NML mut II from the thus obtained strain, cells were streaked over complete medium YPAD+KCl (10 g of yeast extract (Difco), 20 g of peptone (Difco), 20 g of glucose, 0.2 g of adenine sulfate (Wako Pure Chemical Industries, Ltd.), 22.37 g of KCl/1 L) and then cultured. A plurality of single colonies were collected. Of these colonies, strains that had recovered uracil auxotrophy due to plasmid elimination (that is, a strain unable to grow in SD-U+KCl medium) were selected. The thus selected strains were designated as YFY22 strains. The YFY22 strains recovered growth ability (proliferation ability) that had been decreased in the YFY21 strain. Budding yeast Saccharomyces cerevisiae YFY22 was internationally deposited under the Budapest Treaty on Nov. 30, 2010, at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11469.

(4) Generation of YFY23 Strain

The plasmid pSP73-pmt2::HUH linearized with restriction enzyme Pvu II as prepared in (1) above was introduced by the above method into the YFY22 strain obtained as described in (3) above for transformation. From among the thus obtained transformants, pmt2::HUH strain, in which the PMT2 gene in the genome was substituted by homologous recombination with the 5' end-containing fragment of PMT2+HUH+the 3' end-containing fragment of PMT2, was selected and obtained with a colony PCR method. For colony PCR, a forward primer URA-CF: 5'-GGTAGAGGGTGAACGTTAC-3' (SEQ ID NO: 14) and a reverse primer PMT2-R: 5'-CGAATAACACGAGTACGG-3' (SEQ ID NO: 15) were used. The composition of the colony PCR solution was the same as that used for colony PCR upon the above selection of the YFY20 strain. PCR conditions were 1 cycle (94° C. for 5 minutes) of cell disruption, followed by 40 cycles for PCR synthesis (92° C. for 30 seconds, 53° C. for 30 seconds, and 72° C. for 2 minutes), and 1 cycle (72° C. for 7 minutes). 4 µl of the thus obtained amplification product was subjected to electrophoresis using 1.0% agarose gel as described above and then bands were detected. A strain, for which a band specific to pmt2::HUH had been detected, was selected.

To remove the introduced marker gene URA3 from the pmt2::HUH strain, positive selection was carried out using 5-FOA medium in a manner similar to the above. A plurality of strains that had formed colonies on 5-FOA medium were obtained. These strains were confirmed by a PCR method for deletion of URA3 from genomic DNA. PCR was carried out using genomic DNA extracted from the target yeast strain as a template, a forward primer PMT2-F: 5'-GATCCGTTTCGTGTACTG-3' (SEQ ID NO: 16; binding to the 5' end sequence of PMT2), and a reverse primer PMT2-R: 5'-CGAATAACACGAGTACGG-3' (SEQ ID NO: 17; binding to the 3' end sequence of PMT2). The composition of the reaction solution was similar to that used for the above genome PCR. The reaction conditions were 1 cycle (94° C. for 2 minutes) of template denaturation, followed by 30 cycles for PCR synthesis (94° C. for 15 seconds, 53° C. for 30 seconds, and 72° C. for 3 minutes), and 1 cycle (72° C. for 7 minutes). The deletion of the URA3 gene from the genome was confirmed on the basis of detected band lengths. The thus obtained strain, for which the deletion of the URA3 gene had been confirmed, was designated as a YFY23 strain. In the YFY23 strain, both PMT1 gene and PMT2 gene were disrupted.

(5) Generation of YFY24 Strain

The above vector YCplac33/NML mut II was introduced into the YFY23 strain obtained as described above by a method similar to the above for transformation. The thus obtained transformant was cultured in SD-U+KCl liquid medium and then subculture thereof was repeated 10 times to accumulate mutations. Cells after subculture were spread over SD-U+KCL solid medium and then cultured at 30° C. for 5 days. A strain that had formed the largest colony was picked up. To eliminate YCplac33/NML mut II from the thus obtained strain, cells were streaked over complete medium (YPAD solid medium) and then a plurality of single colonies were collected. Of these colonies, strains that had recovered uracil auxotrophy due to plasmid elimination were selected in a manner similar to the above. The thus selected strain was designated as a YFY24 strain. The YFY24 strain recovered growth ability (proliferation ability) that had been decreased in the YFY23 strain. Budding yeast *Saccharomyces cerevisiae* YFY24 was internationally deposited under the Budapest Treaty on Nov. 30, 2010 at the International Patent Organism Depositary (IPOD), the National Institute of Technology and Evaluation (NITE), #120, 2-5-8 Kazusakamatari, Kisarazu-shi, Chiba 292-0818, Japan, under accession number FERM BP-11470.

Example 3

Phenotype Analysis of Sugar-Chain Modified Yeast Strain (1) Evaluation of Growth Ability Eight strains of the sugar-chain modified yeast strains YFY20, YFY21, YFY22, YFY23, and YFY24 prepared in Examples 1 and 2, as well as the TIY20 and YAB100 strains (JP Patent Publication (Kokai) No. 2008-220172 A), and wild-type strain W303-1B (mata, leu2-3, 112trp1-1, can1-100, ura3-1, ade2-1, his3-11, 15; Thomas B J and Rothstein R., (1989) Cell, 56: 619-630), were compared for growth ability as described below.

Figure 3:
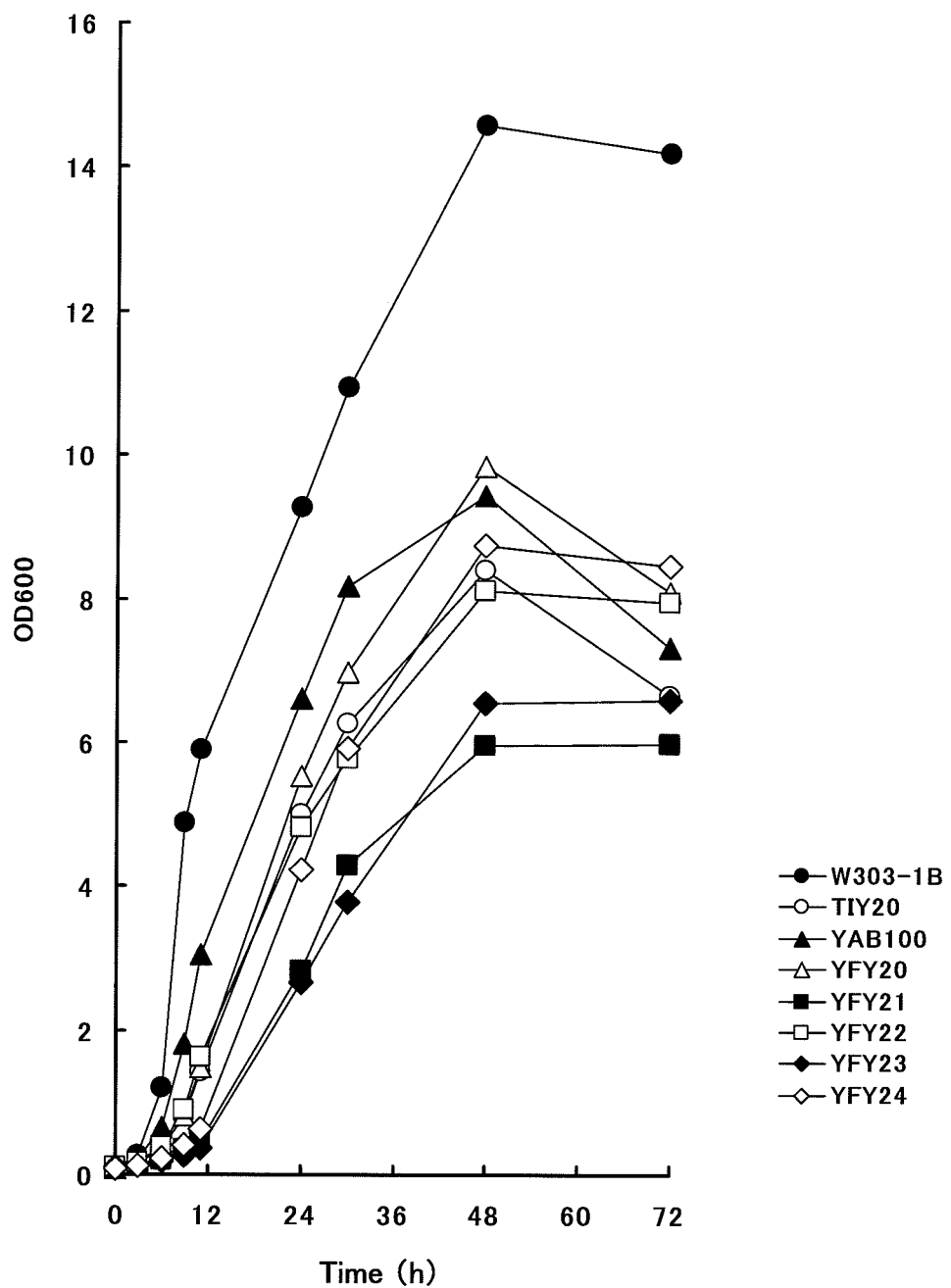
FIG. 3 shows the results of examining the growth ability of 8 yeast strains, including sugar-chain modified yeast strains. Black circles indicate a W303-1B strain, white circles indicate a TIY20 strain, black triangles indicate the YAB100 strain, white triangles indicate the YFY20 strains, black squares indicate a YFY21 strain, white squares indicate a YFY22 strain, black rhomboids indicate a YFY23 strain, and white rhomboids indicate a YFY24 strain.

These yeast strains were pre-cultured in 5 ml of YPAD+KCl liquid medium (30° C.). Each pre-culture solution was inoculated in 20 ml of YPAD liquid medium, so that the cell concentration was $OD_{600}$=0.1. These cells were cultured with shake at 30° C. Turbidity at $OD_{600}$ was measured with time until 72 hours after the initiation of culture. Measurement results are shown in FIG. 3.

In the case of the YFY20 strain (in FIG. 3, white triangles) into which the α-1,2-mannosidase I gene had been introduced, the growth rate was somewhat reduced compared with that of the sugar-chain modified strain YAB100 (in FIG. 3, black triangles) equivalent to the parent strain, but the highest cell concentration reached was almost equivalent to that of the same. In the case of the YFY21 strain (in FIG. 3, black squares) that had been prepared by disruption of the PMT1 gene of the YFY20 strain, the growth rate was significantly decreased and the highest cell concentration reached was decreased to the level of about 60% of that of the YFY20 strain as the parent strain. Meanwhile, in the case of the YFY21-derived YFY22 strain that had recovered growth ability (in FIG. 3, white squares), the growth rate was recovered and the highest cell concentration reached was also recovered to the level of about 82% of that of the YFY20 strain. In the case of YFY23 prepared by further disruption of the PMT2 gene of the YFY22 strain (in FIG. 3, black rhomboids), the growth rate was decreased again and the highest cell concentration reached was decreased to the same level as that of the YFY21 strain. Furthermore, in the case of the YFY24 strain derived from the YFY23 strain, which had recovered growth ability (in FIG. 3, white rhomboids), the growth rate was recovered and the highest cell concentration reached was recovered to the level of about 89% of that of the YFY20 strain (FIG. 3).

(2) Evaluation of Stress Resistance

Eight strains in total, the YFY20 strain, the YFY21 strain, the YFY22 strain, the YFY23 strain, the YFY24 strain, the TIY20 strain, the YAB100 strain, and the W303-1B strain were pre-cultured in 5 ml of YPAD+KCl liquid medium (30° C.). These pre-culture solutions were each serially diluted with sterile water so as to realize the turbidity at $OD_{600}$=1.0, 0.1, 0.01, 0.001, and 0.0001. Five (5) ml each thereof was added dropwise to YPAD solid medium. Static culture was carried out at 30° C., 35° C., or 37° C. and thus high-temperature resistance was evaluated.

Meanwhile, the above cells were similarly added dropwise to YPAD solid medium containing 3 mg/ml hygromycin B (Sigma) or 4 mg/ml Calcofluor white (Sigma) and then subjected to static culture at 30° C. Thus, drug resistance was evaluated.

Figure 4:
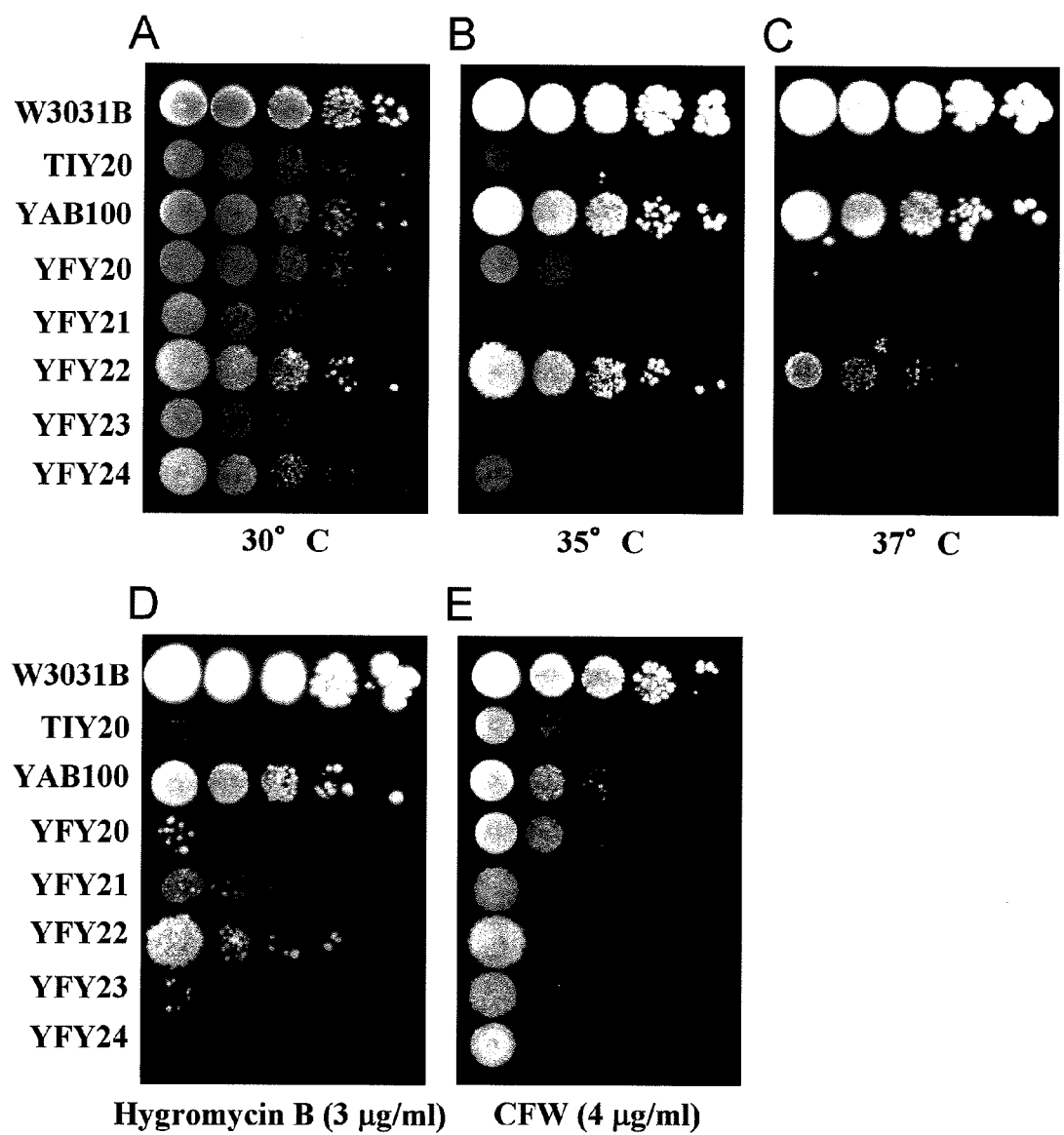
FIG. 4 shows photographs showing the results of a test for resistance to high-temperature stress and drug stress.

As shown in FIG. 4, in the case of the YFY20 strain, resistance to high-temperature stress or drug stress is decreased, compared with the YAB100 strain equivalent to the parent strain. In the case of the YFY21 strain, a growth level under general temperatures was further suppressed compared with the YFY20 strain, demonstrating that resistance to high-temperature stress and resistance to drug stress (against Calcofluor white) were also decreased. On the other hand, in the case of the YFY22 strain, resistance to high-temperature stress and resistance to drug stress were significantly increased, and particularly resistance to high-temperatures and resistance to hygromycin B were enhanced to levels higher than those in the YFY20 strain. In the case of the YFY23 strain, resistance to high-temperature stress and resistance to drug stress were decreased again. The YFY23 strain exhibited significantly high stress sensitivity. However, in the case of the YFY24 strain, a tendency of recovering resistance to high-temperature stress and resistance to drug stress was observed (FIG. 4).

(3) Analysis of O-Linked Sugar Chain Length

To analyze the generation of O-linked sugar chains of sugar-chain modified yeast strains, measurement was carried out as follows using as an index the binding amount of O-linked sugar chains in chitinase that is a secretory protein of yeast.

The YFY20 strain, the YFY22 strain, the YFY24 strain, the TIY20 strain, YAB100 strain, and the W303-1B strain were each cultured in 25 ml of YPAD medium (containing 300 mM KCl) at 30° C. and 180 rpm for 72 hours and then centrifuged for 2 minutes at 1500×g, so that a culture supernatant was collected. Forty (40) mg of wet chitin (wet chitin; crab shell-derived crudely purified chitin (Sigma Aldrich) had been treated with 1% SDS and 1% 2-mercaptoethanol at 100° C. for 10 minutes and then washed 10 times with DDW) was added to the culture supernatant. The mixture was then slowly stirred at 4° C. for 24 hours. After completion of stirring, the resultant was left to stand for a while to remove the culture supernatant, and then chitin was collected. This was washed 3 times with PBS, 80 μl of 2×SDS-PAGE sample buffer was added for suspension, and then the resultant was treated at 100° C. for 10 minutes. Subsequently, the supernatant was collected, and then 5 μl thereof was separated on SDS-PAGE (5%-20%). Detection was carried out by lectin staining using concanavalin A (ConA) that is mannose-binding lectin.

Figure 5:
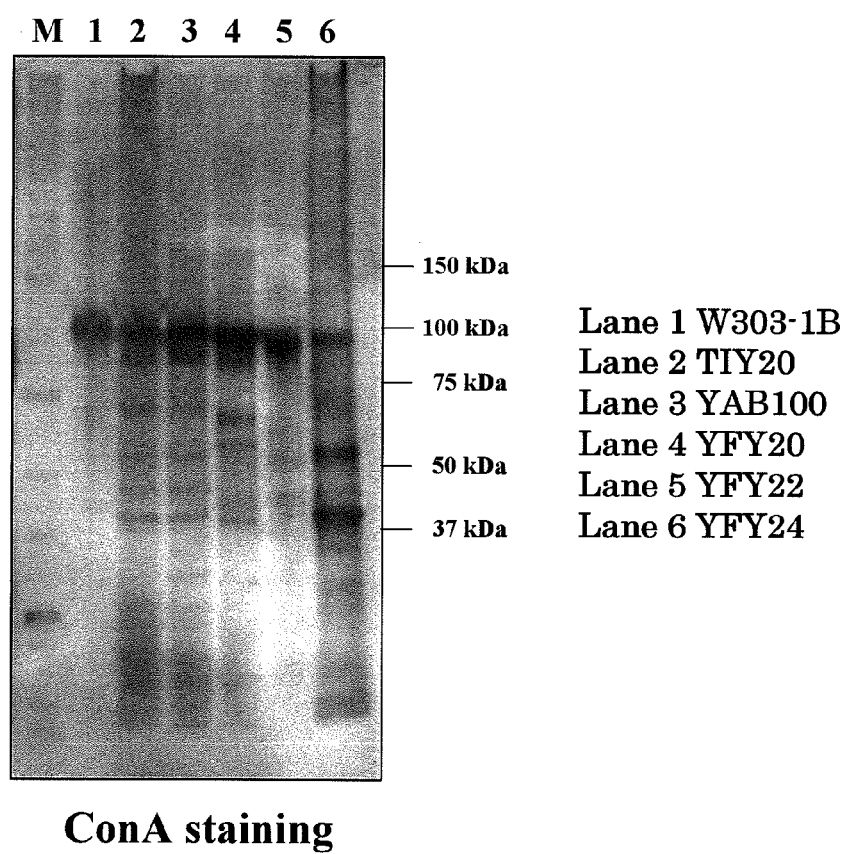
FIG. 5 shows the results of examining the addition of O-linked sugar chains to a chitinase protein produced by 6 yeast strains including sugar-chain modified yeast strains by lectin staining. Lane 1 indicates the W303-1B strain, lane 2 indicates the TIY20 strain, lane 3 indicates the YAB100 strain, lane 4 indicates the YFY20 strain, lane 5 indicates the YFY22 strain, and lane 6 indicates the YFY24 strain.

As shown in FIG. 5, the molecular weight of chitinase in the case of the YFY22 strain and the YFY24 strain shifted to the side of a molecular weight lower than those of the W303-1B strain, the TIY20 strain, the YAB100 strain, and the YFY20 strain. That is, the binding amounts of O-linked sugar chains in chitinase were significantly decreased. These results demonstrate that the disruption of the protein-O-mannosyl-transferase (PMT1, PMT2) genes resulted in significantly decreased amounts of O-linked sugar chains added to the proteins in the YFY22 strain and the YFY24 strain.

Example 4

Generation of YKT1 Strain (1) Preparation of pAUR101-HA-MNN9TMD-OsGnTI Plasmid A fusion gene was constructed by fusing a sequence encoding a transmembrane region (MNN9TMD; amino acid positions 1 to 40; SEQ ID NO: 19) of glycosyltransferase MNN9 (MNN9 gene sequence: GenBank Accession No. NM_001183864, MNN9 full-length amino acid sequence: NCBI database Accession No. NP_015275) of budding yeast to the sequence encoding a transmembrane region-deleted fragment (the sequence of amino acid positions 35 to 442 of NCBI database Accession No. NP_001048631; SEQ ID NO: 18) of the rice-derived GnT-I gene (OsGnTI; N-acetylglucosaminetransferase I) (GenBank Accession No. NM_001055166). Here, the fusion of OsGnTI to the transmembrane region of a yeast protein was intended to allow OsGnTI expressed within yeast cells to be anchored onto yeast Golgi body. Furthermore, an HA tag was also added in order to enable easy confirmation of OsGnTI expression.

Next, the fusion gene HA-MNN9TMD-OsGnTI was amplified from the vector using a forward primer Sac I+fM-HA-MNN9TD F-primer: 5'-AAAAGAGCTCATGCCAT-ACCCATACGATGTTCCAGATTACGCTAT-GTCACTTTCTC TTGTATCGTACCGCCTAAGA-3' (SEQ ID NO: 20), and a reverse primer Xba I+OsGnTI R-primer: 5'-AAAATCTAGACTATACCCTAAGCTGACT-GAGGGAATCCGGA-3' (SEQ ID NO: 21). The product was cloned into the Xba I-Sac I site of yeast expression vector YEp352GAPII to construct an expression vector YEp352GAPII-HA-MNN9TMD-OsGnTI.

Furthermore, for cloning of the fusion gene as a GAPDH expression unit, amplification was carried out by a PCR method using a forward primer Sph I+GAPDHP F-primer: 5'-AAAGCATGCGCAGCGAGTCAGTGAGCGA-3' (SEQ ID NO: 22) and a reverse primer GAPDHT R-primer: 5'-TGTTGGGAAGGGCGATCGGT-3' (SEQ ID NO: 23). The thus obtained amplification fragment (GAP-HA-MNN9TMD-OsGnTI) was cloned into the Sma I-Sph I-HF site of pAUR101 (Takara Bio Inc.) to construct an expression vector pAUR101-HA-MNN9TMD-OsGnTI.

(2) Construction of YKT1 Strain Through Insertion of HA-MNN9TMD-OsGnTI Fragment into Genome DNA of YFY20 Strain The above-constructed pAUR101-HA-MNN9TMD-OsGnTI was linearized via cleavage with BstE II (New England Biolabs), and then the resultant was introduced into the YFY20 strain for transformation. The thus transformed yeast was spread over an YPAD plate containing 0.25 µg/ml Aureobasidin A (Takara Bio Inc.) and 300 mM KCl and then cultured at 30° C. pAUR101 carried resistance gene AUR1-C against an anti-fungal agent, Aureobasidin A. The vector was linearized via cleavage at the restriction enzyme site (BstE II) existing within AUR1-C and then the resultant was introduced into yeast, so that a recombinant(s) became resistant to Aureobasidin A. Thus, the recombinant was selected by culture in Aureobasidin A-containing medium.

The thus formed colonies were transplanted onto similar YPAD plates and then cultured again at 30° C. A small amount of yeast that had grown was scraped off, genomic DNA was extracted using a DNA extraction kit Gen-torukun™ (for yeast) (Takara Bio Inc.), and then the resultant was dissolved in 100 µl of DDW. PCR was carried out using the genomic DNA as a template, a forward primer ScChXI F-primer: 5'-GTCCAAAGTACCAAACTCGACGT-3' (SEQ ID NO: 26), and a reverse primer HA R-primer: 5'-CG-TAATCTGGAACATCGTATGGGT-3' (SEQ ID NO: 27). Strains for which an about 5-kbp band corresponding to the amplification fragment of interest had been confirmed was designated as a YKT1 strain. In addition, the ScChXI F-primer was designed for a sequence on yeast chromosome 11 in the vicinity of the vector insertion site and the HA R-primer was designed for the sequence for the HA tag.

(3) Structural Analysis of Mannan Sugar Chain of YKT1 Strain

It was considered that in the YKT1 strain into which OsGnTI had been introduced, GlcNAc (N-acetylglucosamine) is added to a mannose residue of a mannan sugar chain (sugar chain composed mainly of mannose). Hence, sugar chain structural analysis was conducted for YKT1 in order to examine whether GlcNAc was bound to mannan sugar chains produced by YKT1.

The YKT1 strain and the YFY20 strain were cultured in 20 ml of YPAD medium at 30° C. for 72 hours, and then cells were collected. During culture, glucose was added at 24 hours after culture so that the final concentration was 2%, and then glucose was similarly added every 12 hours. The thus collected cells were subjected to mannoprotein extraction, treatment with glycopeptidase F, and pyridylamination of sugar chains in a manner similar to that in Example 1-(3), and then subjected to HPLC.

Figure 6:
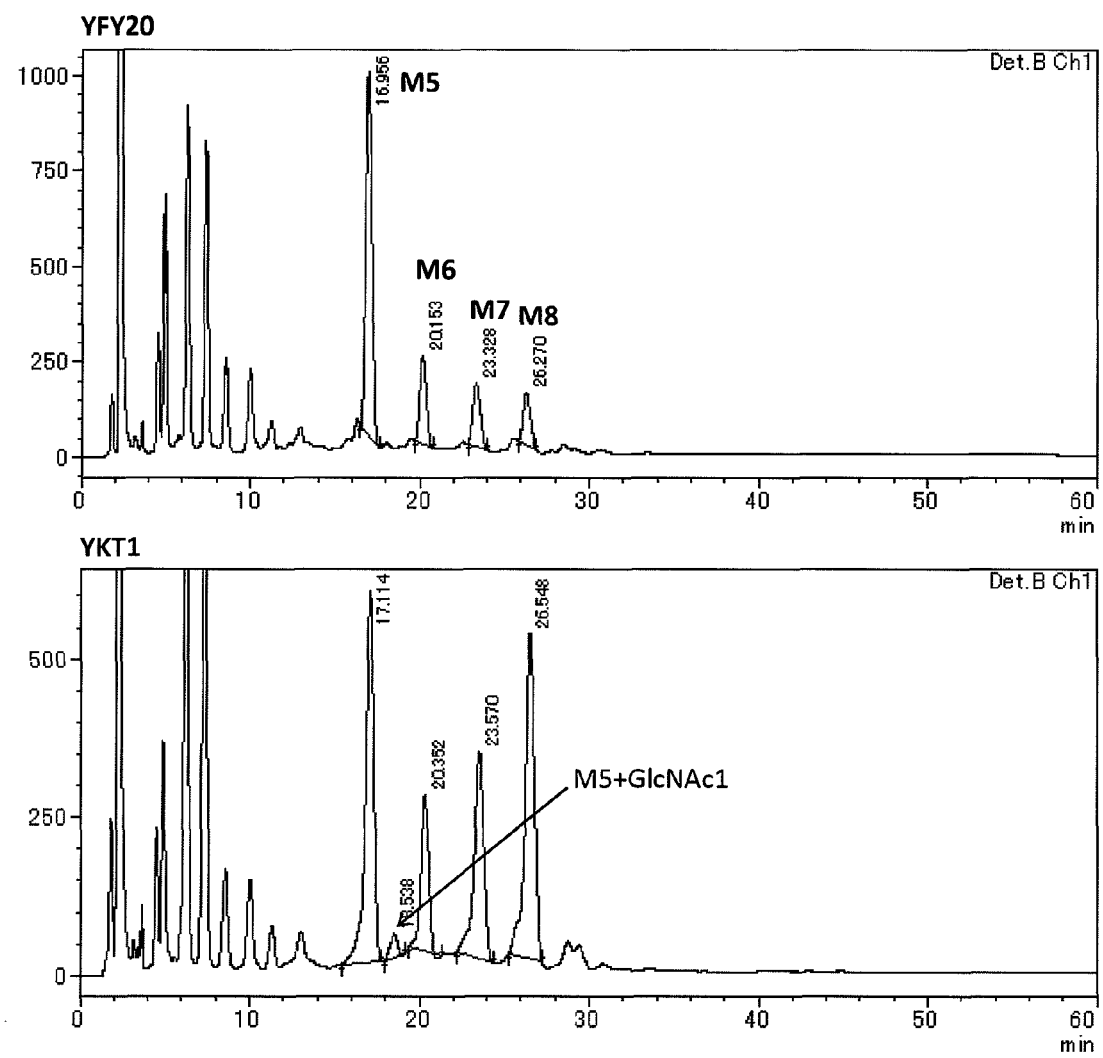
FIG. 6 shows the results of sugar chain structural analysis by HPLC of mannan sugar chains produced by the YFY20 strain and a YKT1 strain.

As shown in FIG. 6, in addition to a peak of the sugar chain of 5 mannose residues as shown in the YFY20 strain, a peak of the sugar chain of 5 mannose residues (M5) to which GlcNAc had been added was observed in the case of the YKT1 strain. These results demonstrated that the YKT1 strain is a strain capable of producing the GlcNAc$_1$Man$_5$GlcNAc$_2$ sugar chain. Budding yeast *Saccharomyces cerevisiae* YKT1 strain was internationally deposited under the Budapest Treaty on Nov. 30, 2010 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11471.

Example 5

Generation of YKT4 Strain

Sugar chains produced by the YFY24 strain prepared in the above Example were analyzed. As a result, regarding the N-linked sugar chains, the amount of M8 was higher than that of M5. Specifically, among N-linked sugar chains, the productivity of the M5 sugar chain was decreased, but the productivity of the M8 sugar chain was increased. This is because a mutation that increases the ability to produce the M8 sugar chain leading to higher growth ability was introduced into the YFY24 strain through application of the disparity mutagenesis method. Therefore, to prepare a double disruption strain having disrupted pmt1 and pmt2 genes and having high productivity of the M5 sugar chain, the *A. saitoi*-derived α-1,2-mannosidase I gene (msdS) used in Example 1 was re-introduced (that is, the second copy of the gene was introduced) into the YFY24 strain as described below.

(1) Construction of Re-Genome-Integration Vector pRS305-OCH1-msdS for *A. Saitoi*-Derived α-1,2-Mannosidase I Gene (msdS)

An OCH1-msdS fragment to which a GAPDH promoter and terminator had been added was amplified by PCR using pRS304-OCH1-msdS prepared in Example 1 as a template. A forward primer Xba I+GAPDHP-F (5'-AAATCTAGAGCG-CAGCGAGTCAGTGAGCGA-3'; SEQ ID NO: 28) and a reverse primer Pst I+GAPDHT-R (5'-AAAACTGCAG-CAACTGTTGGGAAGGGCGATCGGT-3'; SEQ ID NO: 29) were used for PCR. The composition of the PCR solution is as follows.

Composition of Reaction Solution

| | |
|---|---|
| 0.5 ng/µl template DNA solution | 1 µl |
| 10 pmol/µl forward primer | 1.5 µl |
| 10 pmol/µl reverse primer | 1.5 µl |
| 10 mM dNTPs | 1 µl |
| 10 x reaction buffer | 5 µl |
| 5 U/µl Pfx50 DNA polymerase (Invitrogen) | 0.5 µl |
| DDW | 39.5 µl |
| Total | 50 µl |

The reaction conditions were 1 cycle (94° C. for 2 minutes) of initial denaturation, followed by 35 cycles of PCR (94° C. for 15 seconds, 60° C. for 20 seconds, and 68° C. for 2 minutes and 30 seconds), and 1 cycle (68° C. for 3 minutes) of final extension. The thus obtained amplification product was cloned into the Xba I-Pst I site of a genome integration vector pRS305 (GenBank Accession No. U03437.1) for budding yeast. The thus obtained recombinant vector was designated as pRS305-OCH1-msdS.

(2) Preparation of YKT4 Strain

The above-obtained pRS305-OCH1-msdS was linearized via cleavage with a restriction enzyme BstE II, and then introduced into the YFY24 strain for transformation. Transformation of yeast was carried out as described below. First, the YFY24 strain was spread over an SD-L plate (6.7 g of Yeast nitrogen base w/o amino acid (Difco), 20 g of glucose, 0.2 g of adenine sulfate (Wako Pure Chemical Industries, Ltd.), 0.74 g of Leu DO Supplement (Clontech), 22.37 g of KCl, 20 g of agar/1 L) and then cultured at 30° C. for 3 days, so that screening based on leucine auxotrophy was carried out. The thus formed colonies were streaked again over an SD-L plate and then cultured 30° C. for 1 day. A portion of budding yeast that had grown was scraped off and then genomic DNA was extracted using Gen-toru-kun™ (Takara Bio Inc.). A clone in which pRS305-OCH1-msdS had been incorporated into genomic DNA was confirmed by PCR using the genomic DNA as a template. A forward primer ScChIII-F (5'-CAGAGGTCGCCTGACGCATATACCT-3'; SEQ ID NO: 30) and a reverse primer SacI+OCH1TD-F (5'-AAGAGCTCATGTCTAGGAAGTTGTCCCACCT-3; SEQ ID NO: 31) were used for PCR. The PCR solution is as follows.

Composition of Reaction Solution

| | |
|---|---|
| 10 ng/µl template DNA solution | 1 µl |
| 10 pmol/µl forward primer | 0.3 µl |
| 10 pmol/µl reverse primer | 0.3 µl |
| EmeraldAmp (registered trademark) PCR Master Mix (Takara Bio Inc.) | 5 µl |
| DDW | 3.4 µl |
| Total | 10 µl |

The reaction conditions were 1 cycle (94° C. for 5 minutes) of initial denaturation, followed by 35 cycles of PCR (94° C. for 20 seconds, 55° C. for 20 seconds, and 72° C. for 6 minutes), and 1 cycle (72° C. for 3 minutes) of final extension. The amplification product was separated by agarose electrophoresis and then ethidium bromide staining was carried out. A clone, for which amplification from the genomic DNA had been observed, was designated as a YKT4 strain.

(3) Sugar Chain Structural Analysis of YKT4 Strain

The N-linked sugar chains of the YFY24 strain were mainly composed of the sugar chain type of M8, such that M5 accounted for 16% and M8 accounted for about 60% thereof. The N-linked sugar chain structures in the YKT4 strain into which the α-1,2-mannosidase I gene had been introduced again were analyzed to examine the percentages accounted for by M5 and M8. First, the YKT4 strain and the YFY24 strain were cultured in 20 ml of YPAD medium at 30° C. for 72 hours, and then cells were collected. During culture, glucose was added at 24 hours after culture to a final concentration of 2%, and then glucose was similarly added every 12 hours. The thus collected cells were subjected to mannoprotein extraction, treatment with glycopeptidase F, and pyridylamination of sugar chains in a manner similar to that in Example 1-(3), and then they were subjected to HPLC. The results are shown in FIG. 7.

Figure 7:
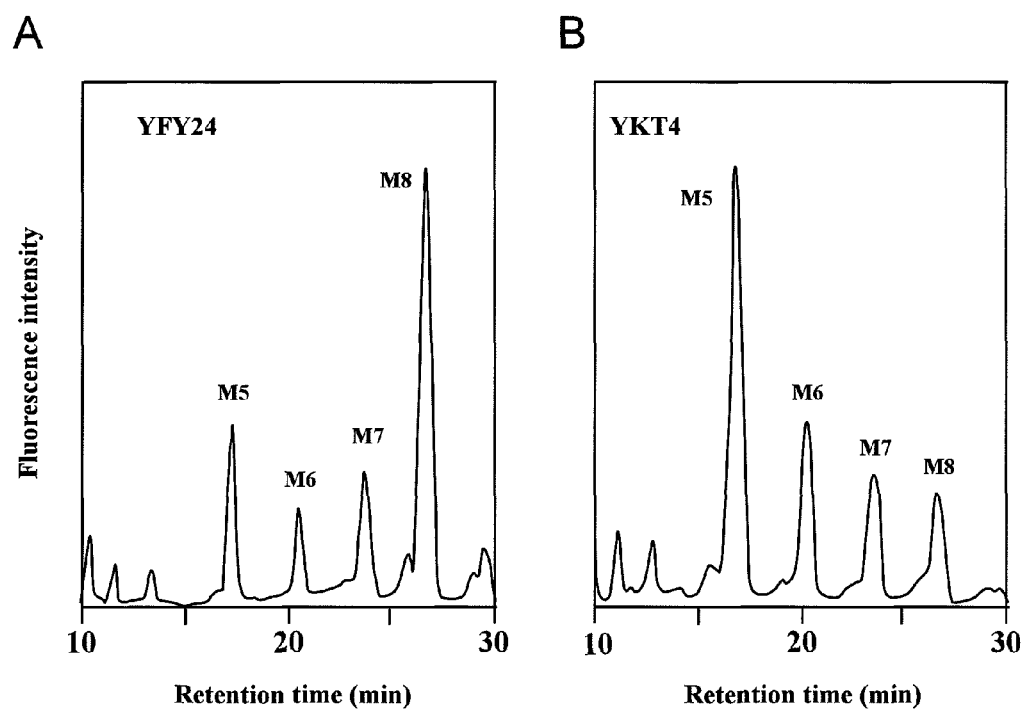
FIG. 7 shows the results of sugar chain structural analysis by HPLC of mannan sugar chains produced in the YFY24 strain and a YKT4 strain.

As shown in FIG. 7, in the case of the YFY24 strain, M8 exhibited the main peak (FIG. 7A), however, in the case of YKT4, the peak of the sugar chain (M5) composed of 5 mannose residues was observed as the main peak (FIG. 7B). It was demonstrated by the results that the YKT4 strain can efficiently produce the M5 sugar chain structure.

The budding yeast *Saccharomyces cerevisiae* YKT4 strain was internationally deposited under the Budapest Treaty on Nov. 8, 2011 at the International Patent Organism Depositary (IPOD), National Institute of Technology and Evaluation (KITE), #120, 2-5-8 Kazusakamatari, Kisarazu-shi, Chiba 292-0818, Japan, under accession number FERM BP-11474.

(4) Analysis of O-Linked Sugar Chain Length

To analyze the addition of O-linked sugar chains in the YKT4 strain, measurement was carried out as follows using as an index the binding amount of O-linked sugar chains on chitinase that is a secretory protein of yeast.

The YKT4 strain and the YFY24 strain were each cultured in 25 ml of YPAD medium (containing 300 mM KCl) at 30° C. and 180 rpm for 72 hours and then centrifuged at 1500×g for 2 minutes, so that a culture supernatant was collected. Furthermore, chitinase samples were prepared by a method similar to that in Example 3-(3). After SDS-PAGE, a chitinase-specific band was detected.

Figure 8:
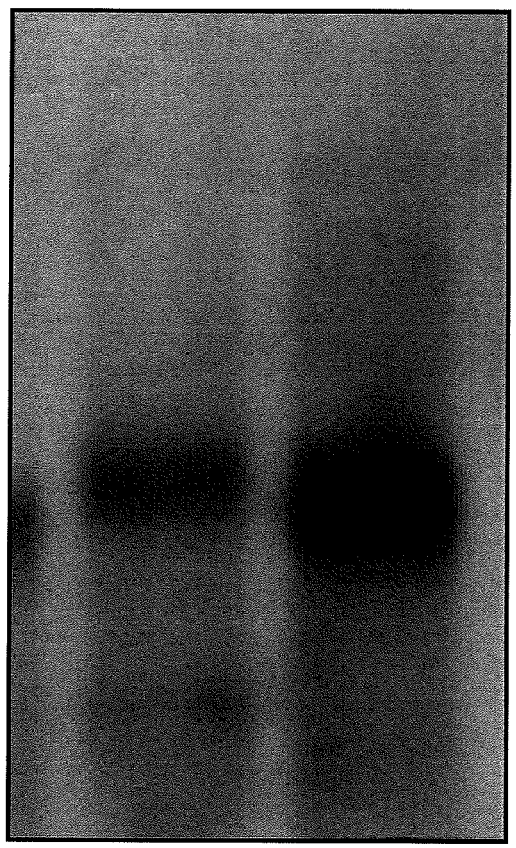
FIG. 8 shows an electrophoretic photograph showing the results of analyzing O-linked sugar chain lengths in glycoproteins (chitinase) produced in the YFY24 strain and the YKT4 strain.

As shown in FIG. 8, the molecular weight of chitinase from the YKT4 strain shifted to the side of a molecular weight lower than that of the YFY24 strain and the binding amount of O-linked sugar chains was decreased in chitinase. In the case of a wild-type strain, mannose was α-1,3-linked to the termini of O-linked sugar chains by an α-1,3-mannosetransferases containing the Mnn1 protein. In YKT4, the MNN1 gene encoding α-1,3-mannosetransferase had been disrupted, so that mannose was transferred via α-1,2 linkage to the termini of many O-linked sugar chains. These results indicate that α-1,2 mannose bound to the termini of O-linked sugar chains in the YKT4 strain was degraded by re-introduction of the α-1,2-mannosidase I gene and thus the O-linked sugar chain lengths were shortened.

Example 6

Generation of YIT3 Strain

For highly efficient production of a recombinant protein in sugar-chain modified yeast, yeast's own protease activity may be decreased. Hence, the PEP4 gene encoding budding yeast's own protease was disrupted in the YKT4 strain obtained in the above example.

(1) Preparation of DNA Fragment for Disruption of PEP4 Gene

A pBSIISK (+)-HUH plasmid was constructed by excising an HUH fragment from pSP73HUH as described in Example 2 (1) using restriction enzymes EcoR I and Pvu II and then introducing the fragment into EcoR I and Sma I sites of pBSIISK (+) (Stratagene). With the use of a PCR method using the thus constructed plasmid pBSIISK (+)-HUH as a template, a forward primer PEP4-DF: 5'-CAAAACTAA-CATGTTCAGCTTGAAAGCATCGACGG-TATCGATAAGCTTG-3' (SEQ ID NO: 32), and a reverse primer PEP4-DR: 5'-GCCAAACCAACCGCATTGTTGC-CCAAATCGCTCTAGAACTAGTGGATCC-3' (SEQ ID NO: 33), a primary amplification fragment was prepared. The primary amplification fragment contains the −10 to +19 region (SEQ ID NO: 58) of the PEP4 gene (GenBank Accession No. M13358) added to the 5' end side of the hisG-URA3-hisG (HUH) fragment and the +1177 to +1205 region (SEQ ID NO: 59) of the PEP4 gene added to the 3' end side of the same. In this state, the PEP4 region contained was too short and insufficient for homologous recombination. Hence, for extension of the PEP4 region, secondary PCR was carried out using the primary amplification fragment as a template, a forward primer PEP4-ELF: 5'-ATTTAATCCAAATAAAAT-TCAAACAAAAACCAAAACTAACATGTTCAGC-3' (SEQ ID NO: 34), and a reverse primer PEP4-ELR: 5'-AG-TAAGAAAAGTTTAGCTCAAATTGCTTTG-GCCAAACCAACCGCATTGT-3' (SEQ ID NO: 35). An amplification fragment was obtained by this reaction, in which the −40 to +19 region (SEQ ID NO: 60) of the PEP4 gene was added to the 5' end side of the HUH fragment and the +1177 to +1235 region (SEQ ID NO: 61) of the PEP4 gene was added to the 3' end side of the same. The thus obtained DNA fragment was designated as a fragment for disruption of the PEP4 gene.

The reaction solution with the following composition was prepared for both primary PCR and secondary PCR.

Composition of PCR Solution

| | |
|---|---|
| 10 x reaction buffer | 5 μl |
| 2.5 mM dNTPs | 4 μl |
| Template DNA | 20 ng equivalent |
| 100 μM forward primer | 1.0 μl |
| 100 μM reverse primer | 1.0 μl |
| DNA polymerase Ex Taq | 0.2 μl |
| Sterilized milliQ water (added to a total amount of 50 μl) | |
| | Total 50 μl |

The reaction conditions employed for both primary PCR and secondary PCR were 1 cycle (98° C. for 2 minutes) of DNA denaturation, followed by 30 cycles for PCR synthesis (98° C. for 10 seconds, 60° C. for 30 seconds, and 72° C. for 4 minutes), and 1 cycle (72° C. for 7 minutes).

(2) Transformation to YKT4 Strain and Confirmation of Disruption of PEP4 Gene With the use of the thus obtained fragment for disruption, the above-obtained YKT4 strain was transformed according to the above method. From among the thus obtained transformants, a pep4::HUH strain (the PEP4 gene in the genome was substituted by homologous recombination with the 5' end-containing fragment of PEP4+HUH+the 3' end-containing fragment of PEP4) was selected and obtained with a colony PCR method. For the colony PCR, a forward primer PEP4-F: 5'-GAGAAGCCTACCACGTAAGGGAAGAATAAC-3' (SEQ ID NO: 36) and a reverse primer PEP4-R: 5'-CCCG-CATATAATGACATTATGGGCAGCAGC-3' (SEQ ID NO: 37) were used. The PCR solution was prepared with the following composition.

Composition of PCR Solution

| | |
|---|---|
| 2 x Emeraldamp PCR master mix | 5.0 μl |
| 0.1% BSA | 1.7 μl |
| Yeast cells | (adequate amount) |
| 100 μM forward primer | 0.1 μl |
| 100 μM reverse primer | 0.1 μl |
| Sterilized milliQ water (added to a total amount of 10 μl) | |
| | Total 10 μl |

PCR conditions were 1 cycle (94° C. for 5 minutes) of cell disruption, followed by 40 cycles for PCR synthesis (92° C. for 30 seconds, 60° C. for 30 seconds, and 72° C. for 4 minutes), and 1 cycle (72° C. for 7 minutes). Four (4) μl of the thus obtained amplification product was subjected to electrophoresis as described above using 1.0% agarose gel, and then bands were detected. A strain for which a band specific to the pep4::HUH strain had been detected was selected. To remove the introduced marker gene URA3 from the pep4::HUH strain, the strain was plated onto the above 5-FOA-containing medium and then a plurality of strains that had formed colonies on the 5-FOA medium were determined to be URA3-deletion strains. URA3 deletion was confirmed for these strains by a PCR method. PCR was carried out using genomic DNA extracted from the yeast strain as a template, the above forward primer PEP4-F, and the above reverse primer PEP4-R. The PCR solution was prepared with the following composition.

Composition of Genome PCR Solution

| | |
|---|---|
| 10 x reaction buffer: | 1 μl |
| Template genomic DNA: | 1 μg |
| 20 μM forward primer: | 0.2 μl |
| 20 μM reverse primer: | 0.2 μl |
| DNA polymerase Ex Taq: | 0.04 μl |
| Sterilized milliQ water: (added to a total amount of 10 μl) | |
| | Total 10 μl |

Reaction conditions were 1 cycle (98° C. for 2 minutes) of DNA template denaturation, followed by 30 cycles of PCR synthesis (98° C. for 10 seconds, 60° C. for 30 seconds, and 72° C. for 4 minutes), and 1 cycle (72° C. for 7 minutes). Deletion of the URA3 gene from the genome was confirmed on the basis of detected band lengths. From among the thus obtained pep4::HUH strains having disrupted PEP4, a strain for which deletion of the URA3 gene had been confirmed was designated as a YIT3 strain. The YIT3 strain was internationally deposited under the Budapest Treaty on Nov. 8, 2011 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11472.

Example 7

Generation of YIT4 Strain

Furthermore, the above YIT3 strain was subjected to the disruption of the PRB1 gene encoding protease as follows.

(1) Preparation of DNA Fragment for Disruption of PRB1 Gene

A DNA fragment for disruption of the PRB1 gene was prepared as follows. With the use of a PCR method using pBSIISK (+)-HUH as a template, a forward primer PRB1-DF: 5'-CTAATTCTAACAAGCAAAGATGAAGT-TAGCGACGGTATCGATAAGCTTG-3' (SEQ ID NO: 38), and a reverse primer PRB1-DR: 5'-CTCTCACTTGAT-CAAAGATTAAATCGGTCGCTCTAGAAC-TAGTGGATCC-3' (SEQ ID NO: 39), a primary amplification fragment was prepared, in which the −19 to +10 region (SEQ ID NO: 62) of the PRB1 gene (GenBank Accession No. M18097) was added to the 5' end side of the hisG-URA3-hisG (HUH) fragment and the +1851 to +1879 region (SEQ ID NO: 63) of the PRB1 gene was added to the 3' end side of the same. In this state, the PRB1 region contained was too short and insufficient for homologous recombination. Hence, for extension of the PRB1 region, a secondary PCR was carried out using the primary amplification fragment as a template, a forward primer PRB1-ELF: 5'-CTTCATCGC-CAATAAAAAAACAAACTAAACCTAAT-TCTAACAAGCAAAG-3' (SEQ ID NO: 40), and a reverse primer PRB1-ELR: 5'-ATTAAATAATATTCAATTTAT-CAAGAATATCTCTCACTTGATCAAAGAT-3' (SEQ ID NO: 41). An amplification fragment was obtained by this reaction, in which the −49 to +10 region (SEQ ID NO: 64) of the PRB1 gene was added to the 5' end side of the HUH fragment and the +1851 to +1909 region (SEQ ID NO: 65) was added to the 3' end side. The thus obtained DNA fragment was used below as a fragment for disruption of the PRB1 gene. The solution and conditions for PCR other than primer sequences were the same as those for the primary PCR and the secondary PCR in Example 6-(1).

(2) Transformation to YIT3 Strain and Confirmation of Disruption of PRB 1 Gene

The YIT3 strain was transformed by techniques similar to those in Example 6-(2) using the above-obtained fragment for disruption. The thus obtained strain was confirmed with colony PCR for disruption of the PRB1 gene. For colony PCR, a forward primer PRB1-F: 5'-GTTACGTCCCGT-TATATTGGAGTTCTTCCC-3' (SEQ ID NO: 42) and a reverse primer PRB 1-R: 5'-AGGGACTCCGACTTGTAAC-CTCGAGACGCC-3' (SEQ ID NO: 43) were used. A strain, for which a band specific to the prb1::HUH strain (the PRB1 gene in the genome was substituted by homologous recombination with the 5' end-containing fragment of PRB1+ HUH+the 3' end-containing fragment of PRB1) had been detected, was selected. URA3 was removed from the prb1:: HUH strain using techniques similar to those in Example 6-(2). The thus obtained URA3-deletion strain was confirmed for URA3 deletion by a PCR method using genomic DNA in a manner similar to that in Example 6-(2). The above forward primer PRB1-F and reverse primer PRB1-R were used for PCR. From among the thus obtained prb1::HUH strains having disrupted PRB1, a strain confirmed to have a deletion of the URA3 gene was designated as a YIT4 strain. The YIT4 strain was internationally deposited under the Budapest Treaty on Nov. 8, 2011 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11473.

Example 8

Preparation of YFY25 Strain

To prepare a strain (derivative strain) capable of secreting and producing a protein at a high level from the YFY20 strain prepared in Example 1, a screening method and a disparity mutagenesis method described below were employed.

(1) Construction of Secretory β-Lactamase Expression Plasmid

A YEp352GAP-II fragment containing no β-lactamase gene (bla; GenBank Accession No. NP_052129) that imparts ampicillin resistance to *Escherichia coli* was amplified by PCR using the above YEp352GAP-II as a template. For PCR, a forward primer Spe I+YEp352 (bla-)-F 5'-GGGAC-TAGTGGTAACTGTCAGACCAAGTTTACTC-3' (SEQ ID NO: 44) and a reverse primer Aat II+YEp352 (bla-)-R 5'-CCACCTGACGTCTAAGAAACCA-3' (SEQ ID NO: 45) were used. The composition of the PCR solution is as follows.

Composition of Reaction Solution

| 0.5 ng/μl template DNA solution | 1 μl |
|---|---|
| 10 pmol/μl forward primer | 1.5 μl |
| 10 pmol/μl reverse primer | 1.5 μl |
| 10 mM dNTPs | 1 μl |
| 10 x buffer | 5 μl |
| 5 U/μl Pfx50 DNA polymerase | 0.5 μl |
| DDW | 39.5 μl |
| Total | 50 μl |

The reaction conditions were 1 cycle (94° C. for 2 minutes) of initial denaturation, followed by 35 cycles of PCR (94° C. for 15 seconds, 55° C. for 20 seconds, and 68° C. for 5 minutes), and 1 cycle (68° C. for 3 minutes) of final extension.

An aminoglycoside-3'-O-phosphotransferase gene (aph; GenBank Accession No. YP_788126) that imparts kanamycin resistance to *Escherichia coli* was amplified by PCR using pCR2.1-TOPO (Invitrogen) as a template. For PCR, a forward primer Aat II+aph-F 5'-AGAAAGACGTCAAAAT-TCAGGGCGCAAGGGCT-3' (SEQ ID NO: 46) and a reverse primer Spe I+aph-R 5'-AGGACTAGTCAGAA-GAACTCGTCAAGAAGGCGA-3' (SEQ ID NO: 47) were used. The composition of the PCR solution is as follows.

Composition of Reaction Solution

| 0.5 ng/μl template DNA solution | 1 μl |
|---|---|
| 10 pmol/μl forward primer | 1.5 μl |
| 10 pmol/μl reverse primer | 1.5 μl |
| 10 mM dNTPs | 1 μl |
| 10 x buffer | 5 μl |
| 5 U/μl Pf x 50 DNA polymerase | 0.5 μl |
| DDW | 39.5 μl |
| Total | 50 μl |

The reaction conditions were 1 cycle (94° C. for 2 minutes) of initial denaturation, followed by 35 cycles of PCR (94° C. for 15 seconds, 55° C. for 20 seconds, and 68° C. for 1 minute), and 1 cycle (68° C. for 3 minutes) of final extension.

Both amplification products obtained as described above were mixed and cleaved with Aat II and Spe I, and then ligated. The resultant was introduced into *Escherichia coli*, a plasmid was extracted to construct a vector YEp352GAP-II' with which a transformed host can be selected using kanamycin as a marker.

Furthermore, a fusion gene was constructed by linking an N-terminal 89 amino acids-coding sequence of a budding yeast MF (ALPHA) 1 gene (GenBank Accession No. NM_001184001; the amino acid sequence of the protein is GenPept (NCBI reference No.) NP_015137.1) and the above β-lactamase gene bla. The fusion gene was cloned into the EcoR I-Kpn I site of a YEp352GAP-II vector to construct a vector pAB109. pAB109 was cleaved with EcoR I-Kpn I to excise an α factor-Bla-encoding fragment. The fragment was ligated to YEp352GAP-II' that had been cleaved similarly. The resultant was introduced into *Escherichia coli*. A plasmid was extracted and was designated as a multicopy β-lactamase expression vector YEp352GAP-II' (α factor-bla). This vector enables the expression and secretion of the fusion protein α factor-bla (SEQ ID NO: 48) under control of a GAPDH promoter and terminator in budding yeast. The vector YEp352GAP-IF (α factor-bla) was further modified to a single-copy expression vector via substitution of the region of a replication origin (2 μm ori) with CEN4-ARS1. A CEN4-ARS1 fragment was amplified by PCR using a yeast single-copy expression vector YCpLac111 (GenBank Accession No. X75457) as a template. For PCR, a forward primer CEN4-ARS1-FHpa: 5'-GTTTGTTAACCGCTGGGCCAT-TCTCATGAA-3' (SEQ ID NO: 49) and a reverse primer CEN4-ARS1-RAat: 5'-GTTTGACGTCCAACTGCATG-GAGATGAGTC-3' (SEQ ID NO: 50) were used. The PCR solution for amplification of the CEN4-ARS1 fragment was prepared with the following composition.

Composition of PCR Solution

| | |
|---|---|
| 10 x reaction buffer | 5 μl |
| Template DNA | 25 ng equivalent |
| 2.5 mM dNTPs | 4 μl |
| 100 μM forward primer | 1 μl |
| 100 μM reverse primer | 1 μl |
| Expand high fidelity enzyme (Roche) | 1 μl |
| Sterilized milliQ water (added to a total amount of 50 μl) | |
| | Total 50 μl |

PCR conditions were 1 cycle (94° C. for 2 minutes) of DNA denaturation, followed by 30 cycles for PCR synthesis (94° C. for 30 seconds, 56° C. for 30 seconds, and 72° C. for 2 minutes (the time for each cycle was prolonged by 5 seconds in the 11$^{th}$ cycle and the following cycles)), and 1 cycle (72° C. for 7 minutes).

Deletion of 2 μm ori from YEp352GAP-II' (α factor-bla) was carried out by digesting the vector with restriction enzymes Hpa I and Aat II. The above-obtained CEN4-ARS1 fragment was inserted into the deletion site.

The thus obtained single-copy β-lactamase expression vector was designated as pYF039.

(2) Construction of Budding Yeast Mutation Vector YCplac111/Mut II

A budding yeast mutation vector YCplac33/NML mut II (International Patent Publication WO 2009/150848) was digested with EcoR I and Sal I to excise a mutant DNA polymerase NML mut II fragment and then the fragment was extracted. The NML mut II fragment was inserted into the EcoR I-Sal I site of a budding yeast vector YCplac111. Thus, a budding yeast mutation vector that enables selection with leucine auxotrophy was constructed and designated as YCplac111/mut II.

(3) Generation of YFY20-1 Strain

The YFY20 strain prepared in Example 1 was transformed simultaneously with the pYF039 and YCplac111/mut II vectors by the above method. For transformant selection medium, SD-UL+KCl (6.7 g of Yeast nitrogen base w/o amino acid (Difco), 20 g of glucose, 0.2 g of adenine sulfate (Wako Pure Chemical Industries, Ltd.), 0.67 g of CSM-LEU-URA (MP Biomedicals), 22.37 g of potassium chloride/1 L) plates were used. The thus obtained 10 transformant strains were together inoculated into 5 ml of SD-UL+KCl liquid medium and then cultured with shake overnight at 30° C.

Cultured cells were diluted 500-fold with sterile water, 50 μl each thereof was spread over a SD-UL+KCl plate, cells were subjected to 3 days of static culture at 30° C. Colonies of 170 strains that had grown were picked up. The activity of β-lactamase secreted by each strain was examined by an iodometric staining method. According to the staining method, first, cells of 170 strains picked up were plated to SDS-UL+KCl (6.7 g of Yeast nitrogen base w/o amino acid (Difco), 1 g of glucose, 2 g of solubilized starch (Wako Pure Chemical Industries, Ltd.), 0.2 g of adenine sulfate (Wako Pure Chemical Industries, Ltd.), 0.67 g of CSM-LEU-URA (MP Biomedicals), 22.37 g of potassium chloride/1 L) plates at about 1-cm intervals in a uniform dot pattern. Static culture was carried out at 30° C. for 2 days. Liquid iodine.ampicillin agar was multi-layered onto the plates and then the plates were left to stand at room temperature until Halo regions were formed. The iodine.ampicillin agar was prepared by adding 10 g/l L Bacto agar (Becton, Dickinson and Company) to SDS-UL+KCl liquid medium, thermally dissolving it using a microwave oven, leaving it to be cooled to about 50° C., adding an iodine solution (15 g of potassium iodide (Wako Pure Chemical Industries, Ltd.), 3 g of iodine (Wako Pure Chemical Industries, Ltd.), 0.3 g of ampicillin sodium (NACALAI TESQUE, INC.)/1 L, 1× phosphate buffer (Sigma)) to agar medium at a volume ratio of 4:1.5, and then gently stirring the mixture.

Figure 9:
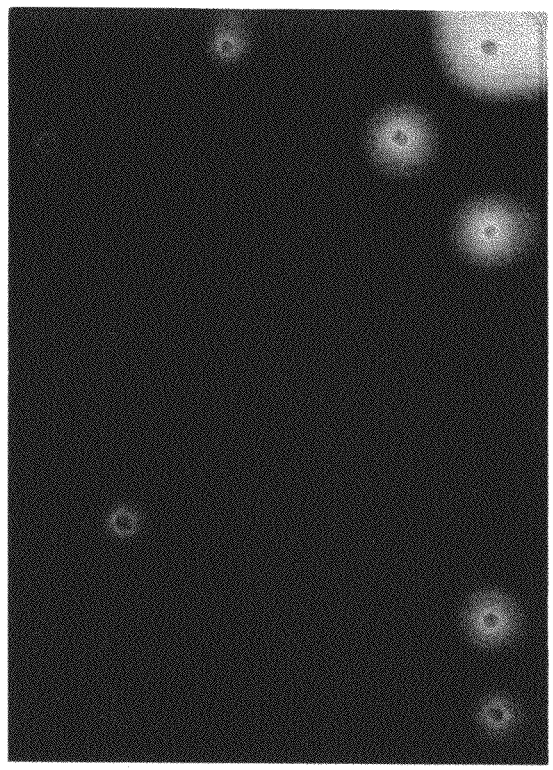
FIG. 9 shows a photograph showing the results of examining the activity of β-lactamase secreted by the YFY20 strain by an iodometric staining method.

The area of the Halo region formed by the staining method is proportional to the activity of β-lactamase secreted by each strain. Hence, 15 strains that had formed the largest Halo regions were selected (FIG. 9). These strains were cultured together in SD-UL+KCl liquid medium and then subculture was repeated 5 times to accumulate mutations. The thus obtained cells in which the mutations had been accumulated were isolated by the above method, and then strains that had secreted β-lactamase at high levels were selected by performing the iodometric staining again. Such accumulation of the mutations and selection of strains secreting the protein at high levels were repeated 3 times in total, so that the finally selected 10 strains were obtained. These strains were further cultured together in SD-L+KCl liquid medium to eliminate pYF039. After subculture was repeated 3 times, cells were streaked over SD-L+KCl plates and then cultured, so that a plurality of single colonies were collected. Of these strains, a strain that had recovered uracil auxotrophy due to elimination of pYF039; that is, a strain incapable of growing in SD-U+KCl medium was selected. The thus selected strain was designated as a YFY20-1 strain.

(4) Construction of α-Amylase Expression Vector pYF048

The −1040 to +1687 region of *Saccharomycopsis fibuligera*-derived α-amylase gene (GenBank Accession No. E01174) was inserted into the EcoR I-Sal I site of budding yeast vector pRS304 to construct a vector pYF020. Subsequently, pYF020 was digested with Sac I and Sal I to excise an α-amylase fragment and the fragment was extracted. The extracted fragment was inserted into the Sac I-Sal I site of a budding yeast vector pRS316. The thus constructed vector was designated as pYF048.

(5) Construction of Glucoamylase Expression Vector pYF053

A PIR2-FLAG fragment was inserted into the Sac I-Sma I site of a budding yeast multicopy expression vector YEP352GAP II to construct a plasmid pYF005. The PIR2-FLAG fragment was amplified by PCR using pAB51 (Abe et al. FEMS YESCT Research4, p 417-425, 2004) as a template, a forward primer PIR2-FSac: 5'-GTTTGAGCTCATG-CAATACAAAAAGAC-3' (SEQ ID NO: 51) and FLAG-RSma: 5'-GTTTCCCGGGCTTGTCATCGTCATCCTTG-3'

(SEQ ID NO: 52). The composition of the PCR solution was the same as that used in PCR upon the above construction of pYF039. PCR conditions were 1 cycle (94° C. for 2 minutes) of DNA denaturation, followed by 30 cycles for PCR synthesis (94° C. for 30 seconds, 46° C. for 30 seconds, and 72° C. for 1 minute and 20 seconds (the time for each cycle was prolonged by 5 seconds in the 11$^{th}$ cycle and the following cycles)), and 1 cycle (72° C. for 7 minutes). Subsequently, *Aspergillus awamori* var. *kawachi*-derived glucoamylase gene fragment (GenBank Accession No. D00427) was inserted into the Sma I-Xba I site of pYF005 to construct pYF025. The glucoamylase gene fragment was amplified by PCR using YEUp-GA I (Goto et al, Applied and Environmental Microbilogy 61, p 3926-3930, 1994) as a template, a forward primer AkGA-FSma: 5'-GTTTCCCGGGGCGAC-CTTGGATTCGTGG-3' (SEQ ID NO: 53), and a reverse primer AkGA-RXba: 5'-GTTTTCTAGACTACCGCCAG-GTGTCGGT-3' (SEQ ID NO: 54). The composition of the PCR solution was the same as that used for PCR upon the above construction of pYF039. PCR conditions were 1 cycle (94° C. for 2 minutes) of DNA denaturation, followed by 30 cycles for PCR synthesis (94° C. for 30 seconds, 58° C. for 30 seconds, and 72° C. for 2 minutes (the time for each cycle was prolonged by 5 seconds in the 11$^{th}$ cycle and the following cycles)), and 1 cycle (72° C. for 7 minutes). Furthermore, pYF025 was digested with Pvu I, so that a region containing a nutritional selection marker URA3 and a replication origin (2 μm ori) was deleted. A fragment, which was obtained via digestion of pRS313 with Pvu I, containing a nutritional selection marker HIS3 and a replication origin CEN6-ARSH4 in a budding yeast single-copy expression vector pRS313 (GenBank Accession No. U03439) was inserted into the region after deletion. The thus constructed vector was designated as pYF053.

(6) Generation of YFY25 Strain

Figure 10:
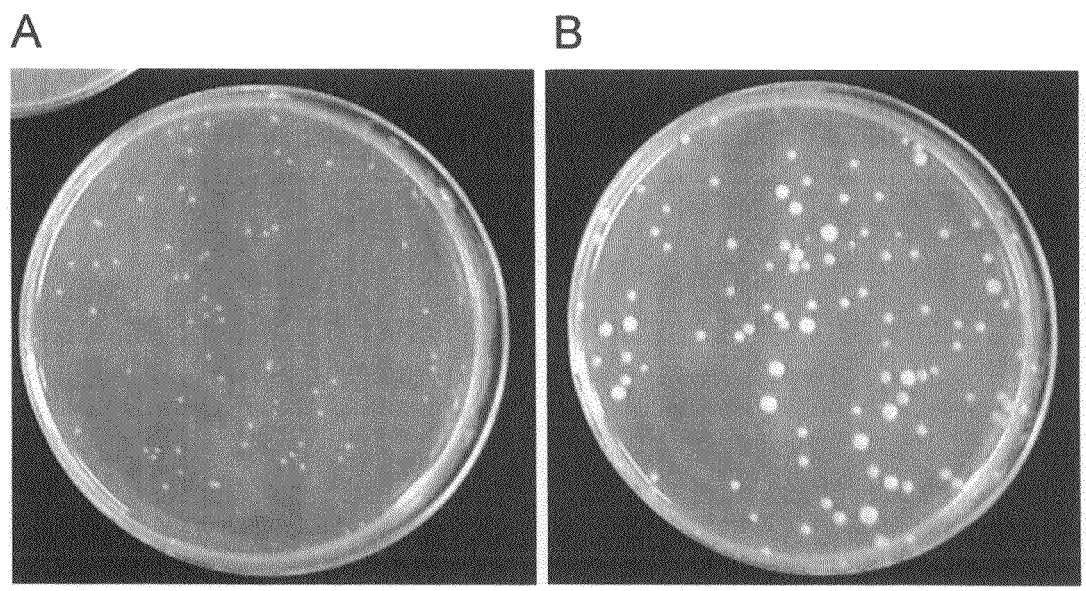
FIG. 10 shows photographs showing the results of growing an YFY20-1 strain, into which a pYF048 α-amylase expression vector and a pYF053 glucoamylase expression vector have been introduced, in SDS-GULH+KCl medium containing starch as a sole carbon source.

The YFY20-1 strain was transformed simultaneously with pYF048 and pYF053 by the above method. For transformant selection medium, SD-ULH+KCl (6.7 g of Yeast nitrogen base w/o amino acid (Difco), 20 g of glucose, 0.2 g of adenine sulfate (Wako Pure Chemical Industries, Ltd.), 0.65 g of -His/-Leu/-Ura DO supplement (Clontech), 22.37 g of potassium chloride/1 L) plates were used. The thus obtained 30 transformant strains were cultured together in SD-UL+KCl liquid medium, diluted 500-fold with sterile water, spread over SDS-GULH+KCl (6.7 g of Yeast nitrogen base w/o amino acid (Difco), 20 g of solubilized starch (Wako Pure Chemical Industries, Ltd.), 0.2 g of adenine sulfate (Wako Pure Chemical Industries, Ltd.), 0.65 g of -His/-Leu/-Ura DO supplement (Clontech), 22.37 g of potassium chloride/1 L) plates, and then cultured for 6 days. Plates on day 6 of culture are shown in FIG. 10. Budding yeast is originally almost unable to grow in SDS-GULH+KCl medium containing starch as a sole carbon source (FIG. 10A). However, when foreign a amylase and glucoamylase were expressed and secreted, the strains became possible to grow in the medium (FIG. 10B).

The growth rate on SDS-GULH+KCl medium may depend on the amount of a amylase and glucoamylase secreted. Hence, 10 strains that had formed the largest colonies on the SDS-GULH+KCl plates were selected and then cultured together in SDS-GULH+KCl liquid medium. Subculture was repeated 10 times to accumulate mutations. Cells in which mutations had been accumulated were spread over SDS-GULH+KCl plates and cultured. 10 strains that had formed the largest colonies were selected. Such accumulation of the mutations and selection of strains secreting the proteins at high levels were repeated 3 times in total, so that the finally selected 10 strains were obtained. These strains were cultured together in SD-L+KCl liquid medium, so as to eliminate pYF048 and pYF053. Subculture was repeated 3 times. Cells were streaked over SD-L+KCl plates and then cultured, so that a plurality of single colonies were collected. Of these strains, a strain that had recovered uracil auxotrophy and histidine auxotrophy because of elimination of pYF048 and pYF053; that is, a strain incapable of growing in either SD-U+KCl medium or SD-H+KCl medium (6.7 g of Yeast nitrogen base w/o amino acid (Difco), 20 g of glucose, 0.2 g of adenine sulfate (Wako Pure Chemical Industries, Ltd.), 0.77 g of -His DO supplement (Becton, Dickinson and Company), 22.37 g of potassium chloride/1 L) was selected. The thus selected strain was designated as a YFY25 strain.

Example 9

Generation of YFY26 Strain

To obtain a strain capable of secreting and producing a protein at a higher level from the YFY25 strain, the PEP4 gene in the YFY25 strain was disrupted by techniques similar to those in Example 6, so that a YFY26 strain was constructed. The YFY26 strain was internationally deposited under the Budapest Treaty on Dec. 5, 2011 at the International Patent Organism Depositary (IPOD), National Institute of Technology and Evaluation (NITE), #120, 2-5-8 Kazusakamatari, Kisarazu-shi, Chiba 292-0818, Japan, under accession number FERM BP-11475. The YFY26 strain was prepared based on the YFY20 strain and was capable of producing the M5 or M8 sugar chain.

Example 10

Evaluation of Ability to Produce Recombinant Protein

Examination of the ability to express a recombinant protein of the thus constructed yeast strains requires introduction of single copy of a gene encoding an appropriate foreign protein into each yeast cell. Hence, a genome integration vector expressing human stable galectin 9 was constructed as described below. A human stable galectin 9 gene was integrated using the vector into the genomic DNA of each yeast strain. The ability to produce a recombinant protein of yeast strains was evaluated as follows based on the amounts of galectin 9 produced and secreted.

(1) Construction of Galectin 9 (G9Null) Expression Vector

A sequence encoding N-terminal 89 amino acids of budding yeast MF (ALPHA) 1 gene (GenBank Accession No. NM_001184001; the amino acid sequence of the protein was GenPept (NCBI reference number) NP_015137.1) and a sequence encoding modified human galectin 9 (G9null) (Nishi et al. FEBS Lett., 579-10, p 2058-2064, 2005) were ligated to form a fusion gene. An α factor-G9null-encoding fragment to which a GAPDH promoter and terminator had been added, was amplified by PCR using a plasmid PAB108 (Abe et al., Glycobioloby, 19-4, p 428-436 (2009)) expressing the fusion gene as a template. For PCR, a forward primer Not I+GAPDHP-F 5'-AAAGCGGCCGCAGCGAGTCAGT-GAGCGA-3' (SEQ ID NO: 55) and a reverse primer Spe I+GAPDHT-R 5'-TTTACTAGTATGATGTGGTCTCTA-CAGGATCTGA-3' (SEQ ID NO: 56) were used. The composition of the PCR solution is as follows.

Composition of Reaction Solution

| | |
|---|---|
| 0.5 ng/µl template DNA solution | 1 µl |
| 10 pmol/µl forward primer | 1.5 µl |
| 10 pmol/µl reverse primer | 1.5 µl |
| 10 mM dNTPs | 1 µl |
| 10 x buffer | 5 µl |
| 5 U/µl Pfx50 DNA polymerase | 0.5 µl |
| DDW | 39.5 µl |

The reaction conditions were 1 cycle (94° C. for 2 minutes) of initial denaturation, 35 cycles of PCR (94° C. for 15 seconds, 60° C. for 20 seconds, and 68° C. for 2 minutes), and 1 cycle (68° C. for 3 minutes) of final extension. The thus obtained amplification product was cloned into the Not I-Spe I site of a budding yeast genome integration vector pRS303 (GenBank Accession No. U03435.1). The thus obtained vector designated as pRS303-α factor-G9null can express and secrete fusion protein α factor-G9null (SEQ ID NO: 57) under control of a GAPDH promoter and terminator in budding yeast.

(2) Isolation of Strain Expressing Human-Derived Galectin 9 (G9Null)

The vector pRS303-α factor-G9null was linearized via cleavage with Nhe I. The YKT4, YIT3, YIT4, YFY26, and YFY20 strains were transformed with the resultant by a method similar to that in Example 5-(2), so that it was integrated into the histidine gene loci of the YKT4, YIT3, YIT4, YFY26, and YFY20 strains. Transformants were spread over SD-H plates (6.7 g of Yeast nitrogen base w/o amino acid (Difco), 20 g of glucose, 0.2 g of adenine sulfate (Wako Pure Chemical Industries, Ltd.), 0.74 g of His DO Supplement (Clontech), 22.37 g of KCl, 20 g of agar/1 L) and then cultured at 30° C. for 3 days. Screening was carried out based on histidine auxotrophy. The thus generated colonies were streaked again over SD-H plates and then cultured at 30° C. for 1 day.

(3) Comparison of α Factor-G9Null Production (Secretion) Amounts

Figure 11:
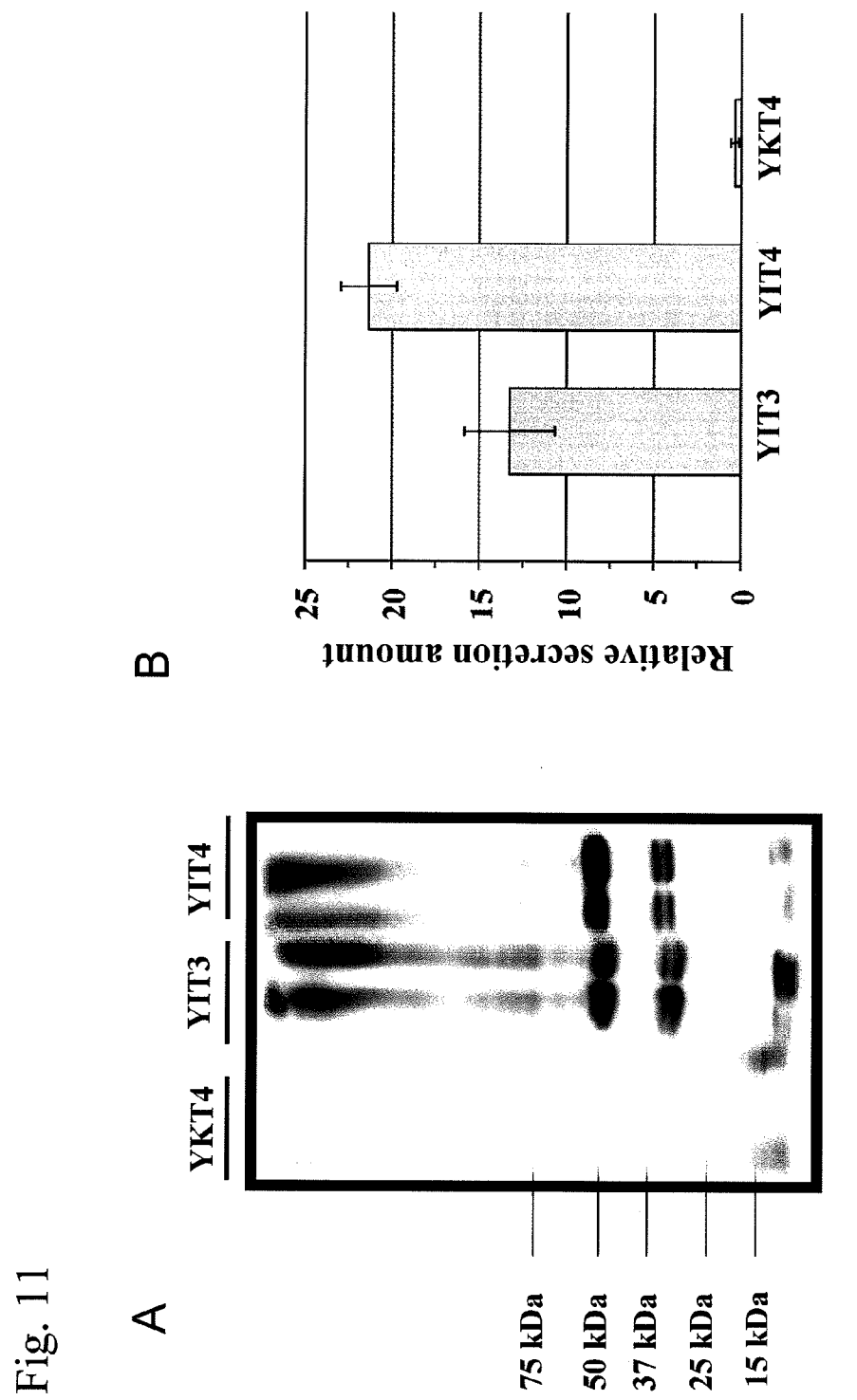
FIG. 11 shows an electrophoretic photograph (FIG. 11A) showing the amounts of galectin 9 (G9null) in the culture supernatants of a YKT4 strain, a YIT3 strain, and a YIT4 strain into which α factor-G9null has been introduced, and a graph (FIG. 11B) showing the relative secretion amounts.

Each strain that had been observed to grow on SD-H plates was cultured with shake in 5 ml of YPADC+KCl (10 g of yeast extract, 20 g of peptone, 50 g of glucose, 0.2 g of adenine sulfate, 20 g of casamino acid (Difco), 22.37 g of KCl/1 L) under conditions of 30° C., 72 hours, and 160 rpm. Yeast after culture was centrifuged at 2,300×g for 1 minute. Two (2) ml of each culture supernatant was collected, 15 µl of Strata-Clean resin (Stratagene) was added, and then the resultant was spun at room temperature and 10 rpm for 15 minutes. Subsequently, centrifugation was carried out at 2,300×g for 1 minute, so as to collect the resin. The resultant was suspended in 15 µA of SDS-PAGE buffer (50 mM Tris-HCl, 1% SDS, 50 mM DTT, 0.01% BPB, 10% glycerol, pH 6.8) and then heated at 100° C. for 3 minutes. The resultant was then subjected to acrylamide gel (SuperSep™ Ace 5%-20% (Wako Pure Chemical Industries, Ltd.)) electrophoresis with a constant current of 30 mA using 1× Tris/glycine/SDS (BIO-RAD). Subsequently, proteins in gels were transferred to PVDF membranes (FluoroTrans (registered trademark) W 0.2 µm (PALL)) using BSN buffer (48 mM Tris-HCl, 39 mM glycine, 20% methanol) and a constant voltage of 10 V for 1 hour. The production amount of human galectin 9 (the amount of the protein produced and secreted) was detected by Western blotting using a rabbit-derived polyclonal antibody against human galectin 9. As shown in FIG. 11A and FIG. 11B, the YIT3 strain exhibited the production amount of G9-null about 12 times and the YIT4 strain exhibited the same about 20 times the production of G9-null in the case of the YKT4 strain. It was demonstrated that the production amounts of G9-null in these strains were significantly high.

(4) Comparison of Human Galectin 9 Expression in YFY26 Strain

The production amounts of galectin 9 from the above-constructed human galectin 9-expressing YFY20 strain, YFY25 strain, and YFY26 strain, into which α factor-G9null had been introduced, were analyzed by a method similar to that in (3) above.

Figure 12:
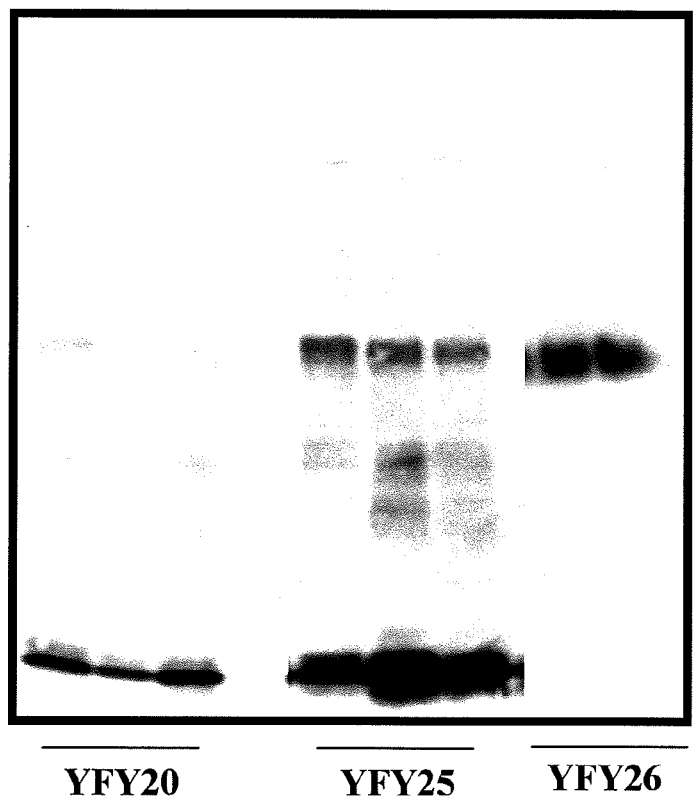
FIG. 12 shows an electrophoretic photograph showing the amounts of galectin 9 (G9null) in the culture supernatants of a YFY20 strain, a YFY25 strain, and a YFY26 strain into which α factor-G9null has been introduced.

The results are shown in FIG. 12. The production amount of G9null from the YFY25 strain was significantly increased compared with that of G9null from the YFY20 strain. Furthermore, even if compared with the production amount of G9null from the YFY25 strain, the production amount of the same from the YFY26 strain was significantly higher. It was demonstrated that the production amount of G9null from the YFY26 strain was about 10 times higher than the production amount of the same from the YFY20 strain.

INDUSTRIAL APPLICABILITY

The present invention can be used for efficiently producing glycoproteins having mammalian-type N-linked sugar chains while reducing the level of the mixing-in of O-linked sugar chains.

All publications, patents, and patent applications cited herein are incorporated herein by reference in their entirety.

What is claimed is:

1. A mutant yeast having an ability to produce N-linked sugar chains of $Man_5GlcNAc_2$, wherein:
   (a) the yeast is functionally deficient in a protein-O-mannosyltransferase gene, an α-1,6-mannosyltransferase gene, an α-1,3 mannosyltransferase gene and a mannose-1-phosphorylation control gene;
   (b) the yeast has a decreased ability to produce O-linked sugar chains relative to a corresponding yeast that is not functionally deficient in a protein-O-mannosyltransferase gene;
   (c) the decreased ability to produce O-linked sugar chains results from the functional deficiency in the protein-O-mannosyltransferase gene;
   (d) an α-1,2-mannosidase I gene has been introduced; and
   (e) the yeast is *Saccharomyces cerevisiae*.

2. The mutant yeast of claim 1, wherein the yeast is functionally deficient in at least one of protein-O-mannosyltransferase genes PMT1 and PMT2.

3. The mutant yeast of claim 1, wherein a decrease in the growth ability due to the functional deficiency of the protein-O-mannosyltransferase gene in the mutant yeast relative to the corresponding yeast that is not functionally deficient in a protein-O-mannosyltransferase gene is suppressed by disparity mutagenesis.

4. The mutant yeast of claim 3, wherein at least one additional copy of an α-1,2-mannosidase I gene further is introduced into the yeast.

5. The mutant yeast of claim 1, wherein the yeast further is functionally deficient in a protease gene.

6. The mutant yeast of claim 5, wherein the yeast is functionally deficient in at least one of protease genes PEP4 and PRB1.

7. The mutant yeast of claim 3, having accession number FERM BP-11469 or FERM BP-11470.

8. The mutant yeast of claim 4, having accession number FERM BP-11474.

9. The mutant yeast of claim 5, having accession number FERM BP-11472 or FERM BP-11473.

10. A mutant yeast having an ability to produce N-linked sugar chains of $Man_5GlcNAc_2$, wherein the yeast is *Saccharomyces cerevisiae* and is functionally deficient in an α-1,6-mannosyltransferase gene, an α-1,3 mannosyltransferase gene and a mannose-1-phosphorylation control gene; and wherein an α-1,2-mannosidase I gene has been introduced.

11. The mutant yeast of claim 10, wherein the yeast further is functionally deficient in a protease gene.

12. The mutant yeast of claim 11, having accession number FERM BP-11475.

13. A method for producing a glycoprotein in a yeast comprising introducing a nucleic acid encoding the amino acid sequence of the glycoprotein into the mutant yeast of claim 1 to produce a transformed yeast, and expressing the glycoprotein in the transformed yeast, wherein the yeast is *Saccharomyces cerevisiae*.

14. A method for producing a glycoprotein in a yeast comprising introducing a nucleic acid encoding the amino acid sequence of the glycoprotein into the mutant yeast of claim 5 to produce a transformed yeast, and expressing the glycoprotein in the transformed yeast, wherein the yeast is *Saccharomyces cerevisiae*.

15. A method for producing a glycoprotein in a yeast, the method comprising introducing a nucleic acid encoding the amino acid sequence of the glycoprotein into the mutant yeast of claim 10 to produce a transformed yeast, and expressing the glycoprotein in the transformed yeast, wherein the yeast is *Saccharomyces cerevisiae*.

* * * * *